US007951555B2

(12) United States Patent
Taylor et al.

(10) Patent No.: US 7,951,555 B2
(45) Date of Patent: May 31, 2011

(54) MEMBRANE BIOREACTOR

(75) Inventors: Anthony Patrick Andrew Taylor, Bundeena (AU); Kim Suzanne Finnie, Chatswood West (AU); John Bartlett, Towradgi (AU); Peter James Holden, Grays Point (AU)

(73) Assignee: Australian Nuclear Science and Technology Organisation, New South Wales (AU)

( * ) Notice: Subject to any disclaimer, the term of this patent is extended or adjusted under 35 U.S.C. 154(b) by 1072 days.

(21) Appl. No.: 11/569,201

(22) PCT Filed: May 18, 2005

(86) PCT No.: PCT/AU2005/000713
§ 371 (c)(1),
(2), (4) Date: Apr. 23, 2007

(87) PCT Pub. No.: WO2005/111193
PCT Pub. Date: Nov. 24, 2005

(65) Prior Publication Data
US 2008/0044850 A1    Feb. 21, 2008

(30) Foreign Application Priority Data

May 18, 2004    (AU) ............................... 2004902629

(51) Int. Cl.
*C12P 1/00* (2006.01)
*C12P 37/00* (2006.01)
*C12P 35/00* (2006.01)
*C12N 11/00* (2006.01)
*C12N 9/00* (2006.01)
*C12N 5/00* (2006.01)
*C12M 1/00* (2006.01)
*C12M 3/00* (2006.01)

(52) U.S. Cl. .............. 435/41; 435/43; 435/47; 435/174; 435/183; 435/325; 435/289.1

(58) Field of Classification Search .................. None
See application file for complete search history.

(56) References Cited

U.S. PATENT DOCUMENTS

| 4,937,196 A * | 6/1990 | Wrasidlo et al. ........... 435/297.2 |
| 4,948,728 A * | 8/1990 | Stephanopoulos et al. ..... 435/41 |
| 6,379,922 B1 * | 4/2002 | Lee ................................ 435/41 |

FOREIGN PATENT DOCUMENTS

| CN | 2132750 Y | 5/1993 |
| CN | 1161862 A | 10/1997 |
| CN | 1263097 A | 8/2000 |
| JP | 2005-34069 | 7/2003 |
| WO | WO 89/00188 | 1/1989 |
| WO | WO 02/094979 A2 | 11/2002 |

OTHER PUBLICATIONS

K. Brindle et al., "Nitrification in a Bubbleless Oxygen Mass Transfer Membrane Bioreactor", Wat. Sci. Tech. vol. 34, No. 9, 1996, pp. 261-267.
Keith Brindle et al., "Enhanced Biological Treatment of High Oxygen Demanding Wastewaters by a Membrane Bioreactor Capable of Bulleless Oxygen Mass Transfer", Proc. Weftec. 97 Chicago, Oct. 18-22, 1997, pp. 63-72.
Kazuaki Hibiya et al., "Simultaneous nitrification and denitrification by controlling vertical and horizontal microenvironment in a membrane-aerated biofilm reactor", Journal of Biotechnology 100 (2003) pp. 23-32.
C.M. Ho et al., "Autotrophic denitrification via a biofilm growing on a gas-permeable silicon tube", Journal of the Chinese Institute of Environmental Engineering, vol. 12, No. 4, pp. 307-313, Dec. 2002.
A. Ogawa et al., "Production of Kojic Acid From *Aspergillus oryzae* Var.*Oryzae* by Membrane-Surface Liquid Culture", Biotechnology Techniques, vol. 9, No. 2 (Feb. 1995), pp. 153-156.
Akinori Ogawa et al., "Production of Neutral Protease by Membrane-Surface Liquid Culture of *Aspergillus oryzae* IAM2704", Journal of Fermentation and Bioengineering, vol. 80, No. 1, pp. 35-40, 1995.
Akinori Ogawa et al., "Projection of Kojic Acid by Membrane-Surface Liquid Culture of *Aspergillus oryzae* NRRL484", Journal of Fermentation and Bioengineering, vol. 80, No. 1, 41-45, 1995.
Kazuaki Yamagiwa et al., "Simultaneous Organic Carbon Removal and Nitrification by Biofilm Formed on Oxygen Enrichment Membrane", Journal of Chemical Engineering of Japan, vol. 27, No. 5, 1994, pp. 638-643.
A. Yasahara et al., "Production of Neutral Protease From *Aspergillus oryzae* by a Novel Cultivation Method on a Microporous Membrane", Biotechnology Techniques, vol. 8, No. 4, Apr. 1994, pp. 249-254.
Senay Yalcin, "Effectiveness Factors for Hollow Fiber Biofilm Reactions", Proc. of Int. Conf. Mathematics and Eng. Techniq. in Med. and Biol. Sci. Las Vegas USA Jun. 25-28, 304-310 (2001).
H. Kazuhiro et al., JP2002085050, Apparatus for surface culture on non-woven fabric for bioremedication of organic chlorine compound containing drainage and degradation treatment system, Mar. 26, 2002, *Abstract.

* cited by examiner

*Primary Examiner* — David M Naff
(74) *Attorney, Agent, or Firm* — Stephen A. Bent; Foley & Lardner LLP

(57) ABSTRACT

The invention provides a membrane comprising a gel reinforced by a support. The membrane has opposing surfaces and a thickness between said surfaces. The gel communicates between the opposing surfaces and allows diffusion of a nutrient solution through the membrane. A bioreactor is also provided, comprising a membrane-supporting structure, and a membrane according to the invention supported on the membrane-supporting structure.

28 Claims, 25 Drawing Sheets

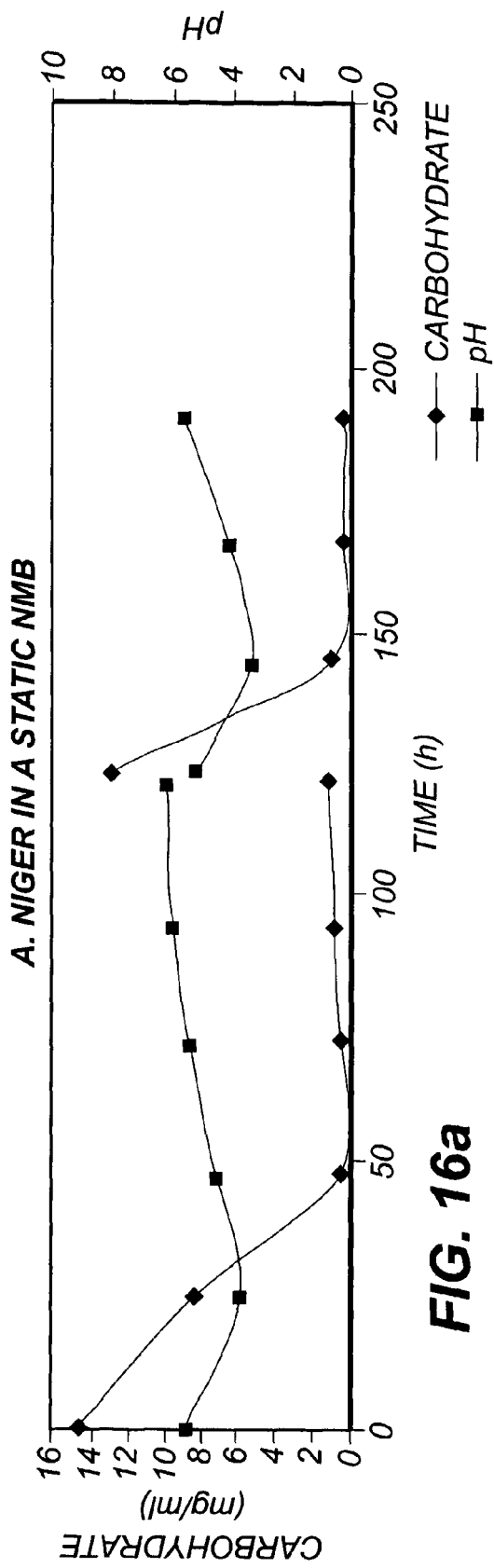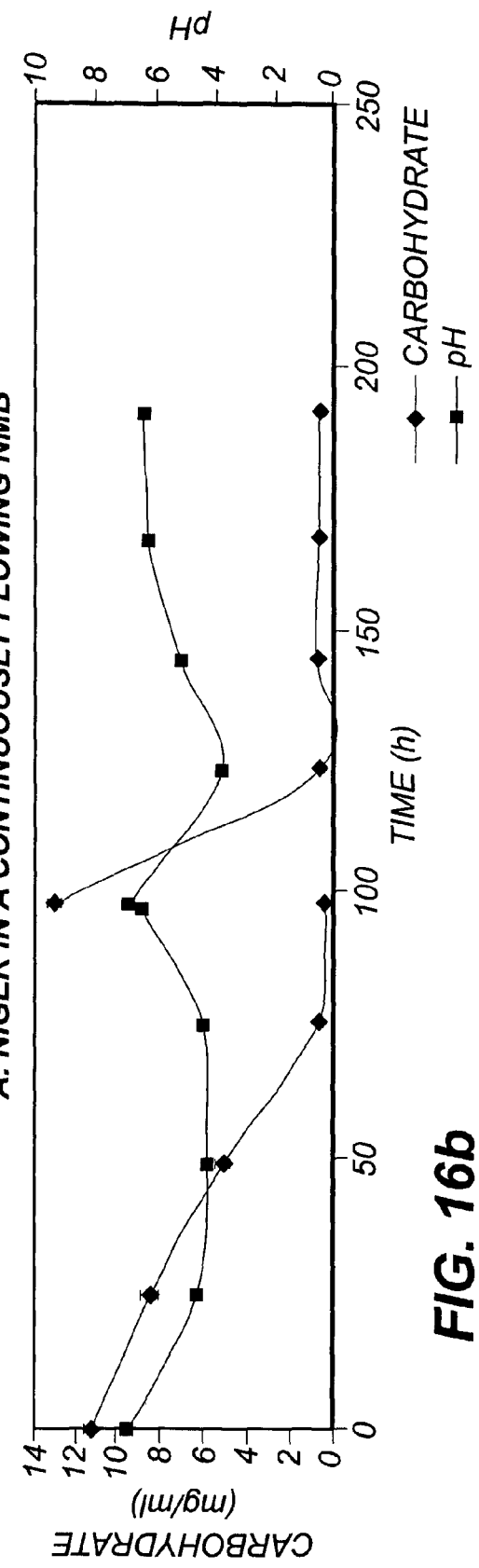
FIG. 16a — A. NIGER IN A STATIC NMB
FIG. 16b — A. NIGER IN A CONTINUOUSLY FLOWING NMB

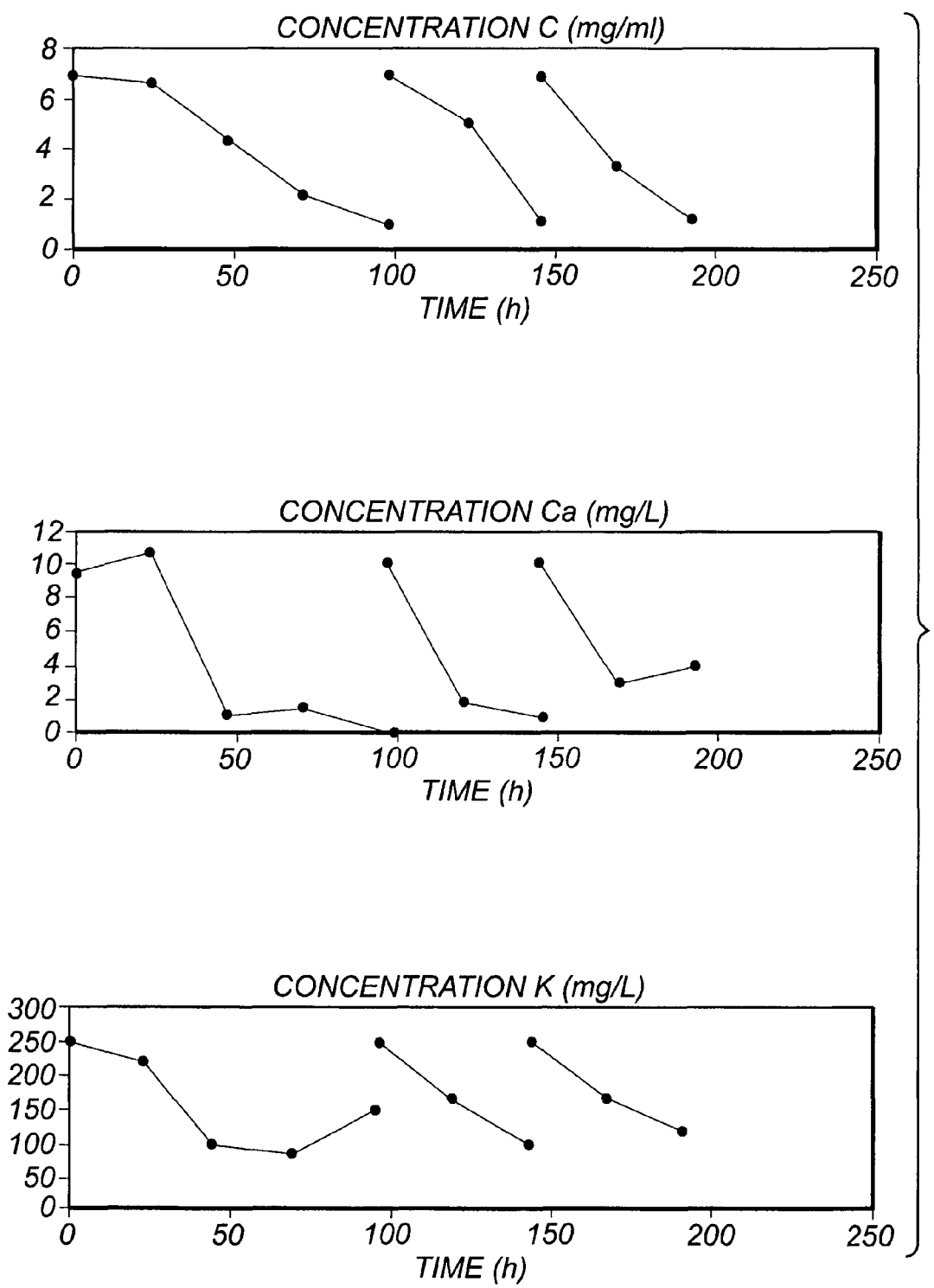
FIG. 18 (PART 1)

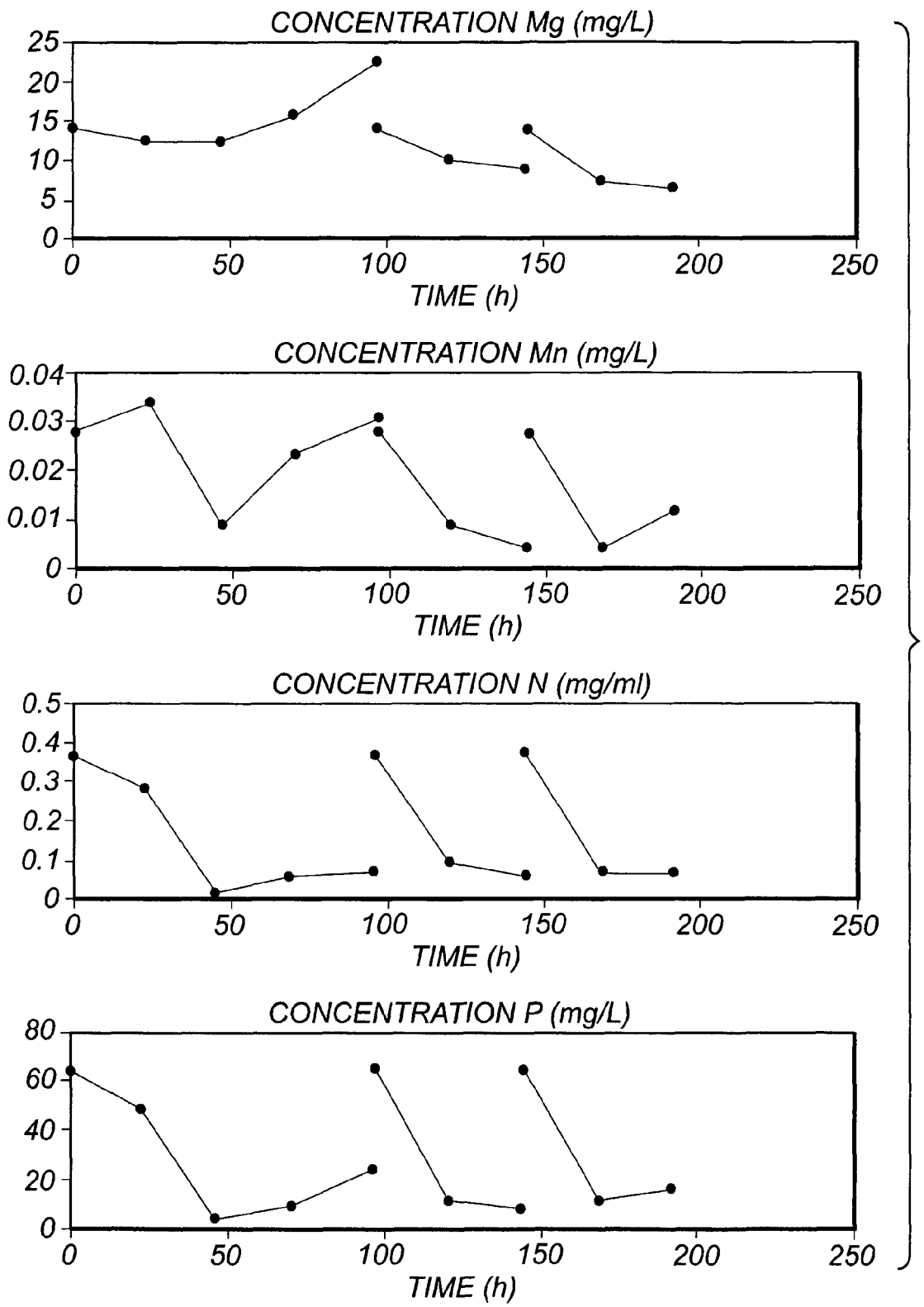
FIG. 18 (PART 2)

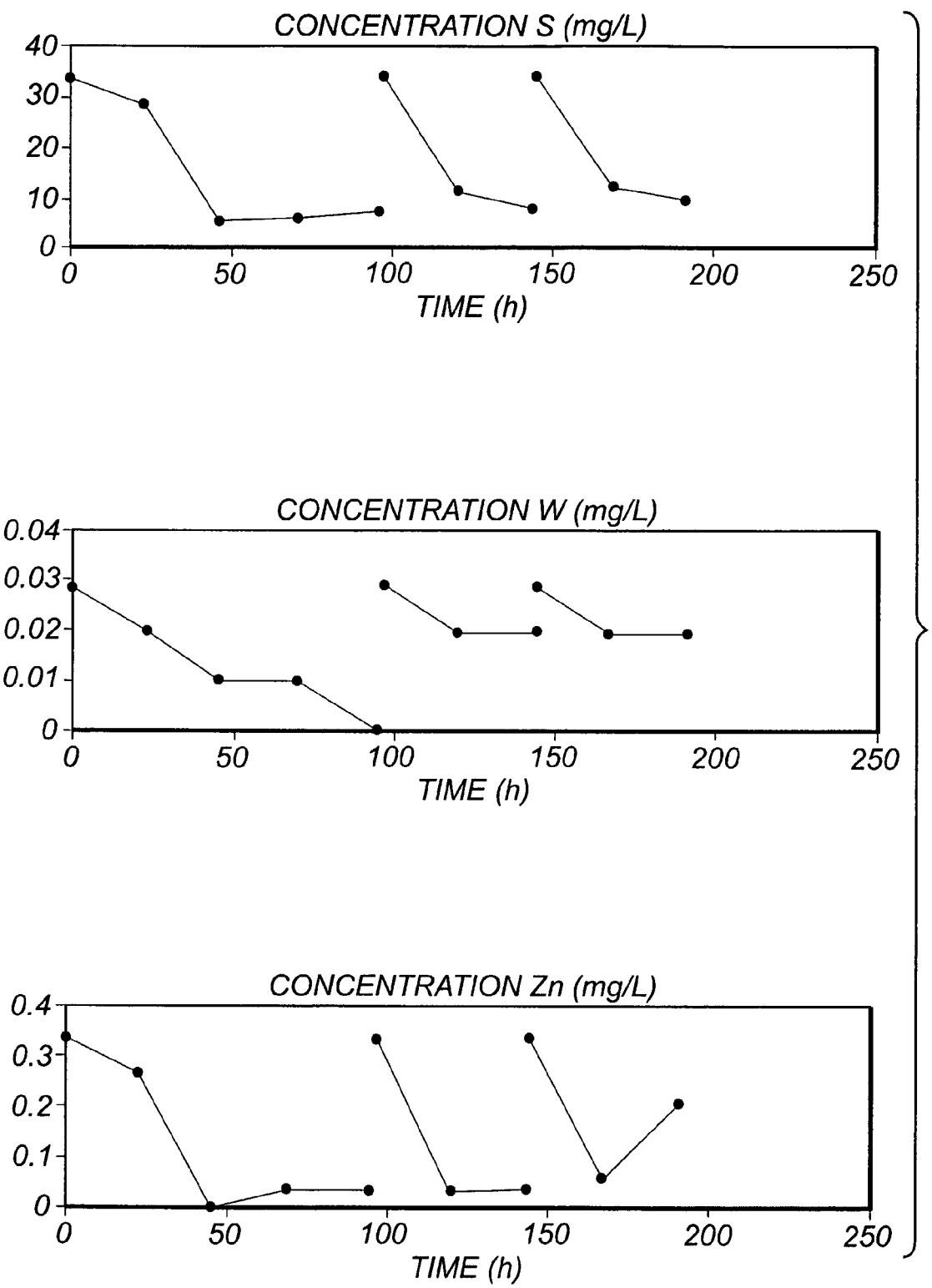
FIG. 18 (PART 3)

MEMBRANE BIOREACTOR

TECHNICAL FIELD

The present invention relates to a membrane bioreactor, processes for making a membrane for use in a membrane bioreactor and methods for using a membrane bioreactor.

BACKGROUND OF THE INVENTION

Membrane bioreactors, which use biological matter in conjunction with a membrane to convert materials supplied to the biological matter, may be used for bioreaction applications such as the production of useful substances, for example pharmaceuticals, antibodies or vaccine components, the bioconversion of organic wastes into biomass or biofuels, or remediation of toxic wastes including degradation of toxic chemicals to inert or non-bioavailable forms and precipitation or reduction/oxidation of heavy metals.

Broadly speaking, existing bioreactors can be classified as mechanically agitated bioreactors, pneumatically agitated bioreactors or non-agitated bioreactors. Mechanically agitated bioreactors include: aeration-agitation bioreactors; rotating drum bioreactors; and spin-filter bioreactors. Pneumatically agitated bioreactors include sparge bioreactors, and air-lift bioreactors. Non-agitated bioreactors include gaseous phase bioreactors, oxygen-permeable membrane aerator bioreactors, and overlay aeration bioreactors.

Pneumatically agitated bioreactors typically consist of a vat fitted with aeration vents that sparge air through the contained liquid medium, to maintain an adequate supply of dissolved oxygen for the biomass. Such reactors use a variety of systems to ensure that the biomass and process liquor remain well mixed, including impellers, propellers, and paddles. Paddles are also used to scrape biomass from the sides of the vessel to minimise fouling and ensure that the biomass remains in contact with the process liquor. However a disadvantage with such systems is that the shear forces associated with such mixing and scraping can often damage fragile cultures, leading to a reduction in biological activity and a consequent reduction in productivity. As well, the presence of the biomass, which is relatively dense, increases the viscosity of the reaction medium, thus reducing both mixing efficiency and the rate of diffusion of molecular oxygen and other gases within the process stream. Any reduction in the availability of oxygen leads to a corresponding reduction in the activity of the biomass, ensuring that many cell types no longer function as they would in natural systems (e.g. at the air-solid interface or, in the case of animal cells, while bathed in blood).

Tissue culture systems include sparged bioreactors and a variety of submerged surface-growth systems in culture vessels or rolling drums. A disadvantage of these systems is that the uptake of oxygen is relatively low, and hence the bioavailability of dissolved oxygen becomes limiting once small amounts of biomass have grown. The low availability of dissolved oxygen prevents many types of cells from being cultured, and many cell lines do not function as they would in the body, where oxygen is more readily available.

In packed column systems, cells are immobilised on inert materials of various shapes such as rings, spheres saddles or polygons which are packed into a column. A nutrient stream is oxygenated prior to being fed to the column. A disadvantage of these systems is that they are limited by the solubility of oxygen in the nutrient stream. They are usually run in trickling mode and oxygen limitation may also relate to thickness of the biomass. A further disadvantage is that growth of the cells can lead to agglomeration of the packing and to clogging of the column. Cost is also an issue for highly engineered versions of these.

Membrane systems may be classified into one of three broad classes:

Type 1: Gas-Liquid Interface Membrane Bioreactors involve the use of a porous membrane host, which is used to support the active biomass on the gas side of the membrane. The other side of the membrane is in contact with the process liquor, which is pumped through the membrane under pressure. A sintered ceramic membrane has been reported for this process (Canto et al, *Science and Engineering Journal,* 1998-2, 2). The sintered ceramic membrane reported was relatively impermeable, so the liquid was pressurized to pump it through the membrane. A disadvantage with this type of bioreactor is that the elevated pressures at which such reactors operate restrict the size of the membrane and its housing, to avoid breakage. The reduced availability of nutrients (due to the relatively low total porosity of the active membrane) restricts the growth of the biomass, thus leading to relatively low product yields. A further example of this type is described in WO90/02170. This patent describes a hollow fibre membrane having a biolayer (biofilm) on the outside. In use, liquid is passed through the lumen of the membrane, and air is provided to the biofilm through a support matrix surrounding the membrane. A disadvantage with this system is that, due to the significant transmembrane pressures required, the support matrix is required around the membrane to prevent damage due to that pressure. The construction of a concentric support matrix/biofilm/membrane system is complex. In addition, it is likely that the support matrix would become fouled with cells from the biofilm in use, leading to reduced diffusion rates of oxygen and nutrients through the biofilm.

Type 2: The culture is grown on the liquid side of the membrane, often under anoxic conditions. In an example, a porous hollow-fibre membrane has been used to immobilize a biofilm in contact with the liquid medium, while oxygen-containing gas is supplied to the other side of the membrane (JP2003251381 Asahi Kasei Corp.). A second patented method has pressurized hydrogen gas introduced into hollow fibers that are sealed at one end to prevent the escape of the hydrogen, and are impervious to liquids. Water surrounds the fibres and a biofilm grows on the liquid side of the membrane using dissolved hydrogen as an electron donor for the cells to remove oxidized chemicals dissolved in the liquid (U.S. Pat. No. 6,387,262, Northwestern University). A disadvantage of such systems is that the gas is provided to the membrane under pressure, necessitating expensive equipment for pressurizing and for housing the pressurised gas. In addition, the specialised membranes required are expensive and require sophisticated equipment for their manufacture.

Type 3: The culture is grown suspended in liquor and filtered from the liquor using a membrane filter. Most membrane bioreactors are type 3. The disadvantages of this class of bioreactor are similar to those of air-lift and tissue culture type bioreactors, and they also suffer from the disadvantages of biofouling of the membrane used to separate the liquor that contains product materials.

There is therefore a need for a bioreactor which is inexpensive, durable, and which can provide for higher rates of bioconversion than conventional systems.

OBJECT OF THE INVENTION

It is the object of the present invention to overcome or substantially ameliorate at least one of the above disadvantages. It is a further object to at least partially satisfy the above need.

SUMMARY OF THE INVENTION

In a first aspect of the invention there is provided a membrane for use in a bioreactor, said membrane having a nutrient face and a gas face, said membrane:
- being capable of supporting an immobilised biolayer on the gas face and/or in the membrane near the gas face;
- being capable of allowing diffusion of a nutrient solution from the nutrient face to the immobilised biolayer; and
- being accessible so as to enable removal of cells from the immobilised biolayer if present.

The membrane may be planar or may be tubular. The membrane may be nanoporous, mesoporous or microporous or may have a combination of nanoscale and/or mesoscale and/or microscale pores. The membrane may comprise a support material, for example a woven or non-woven fibrous material or a non-fibrous porous material. The support material may be a knitted material, a woven material, a compressed fibre material, loose fibres, a felted material or some other suitable material. The support may be internal to the gel or it may be external to the gel e.g. on a surface thereof. The support may be hydrophilic or hydrophobic, and it may have sizing or may have no sizing on the surface thereof. It may be polymeric (e.g. polyester, polyamide, acrylic, polyolefin etc.), inorganic (e.g. glass fibre), natural fibre (cellulose or modified cellulose, cotton etc.) or some other material. The support material may have a nanoporous solid or gel therein and/or thereon. The nanoporous solid or gel may be hydrophilic or hydrophobic. It may be sol-gel derived. It may be not annealed. It may be a hydrogel. The membrane may be capable of separating a gas at the gas face from a nutrient solution at the nutrient face. The membrane may be capable of allowing diffusion of a nutrient solution from the nutrient face to the immobilised biolayer without the external application of pressure. The membrane may have no support matrix on the gas face thereof. The membrane may be a hybrid membrane, having a porous or microporous layer at the liquid face thereof.

The biolayer may comprise bacteria, fungi, animal or plant cells, protozoa or other biological matter. The cells may be prokaryotic or eukaryotic. The animal cells may be, for example, mammalian cells. The biolayer may be capable of producing pharmaceuticals, antibodies, vaccine components, food materials, cells, enzymes or other substances. In order to produce a particular product it is necessary to choose the appropriate biolayer (i.e. cells etc. comprising the biolayer) and the appropriate nutrient solution for that biolayer. If the biolayer comprises mammalian cells, it may be necessary to use a hydrophobic membrane, for example comprising hydrophobic silica. The hydrophobic silica may be for example methylated, octylated or phenylated silica.

The membrane may comprise a gel reinforced by a support, said membrane having opposing surfaces and a thickness between said surfaces whereby the gel communicates between said opposing surfaces and allows diffusion of a nutrient solution through the membrane.

In an embodiment of the first aspect the membrane has an immobilised biolayer on the gas face and/or in the membrane near the gas face. The membrane may be capable of allowing diffusion of a nutrient solution from the nutrient face to the immobilised biolayer without the external application of pressure. In particular, the membrane may comprise a gel reinforced by a support, said membrane having a nutrient face, a gas face and a thickness between said faces, said membrane having an immobilised biolayer in a location selected from on the gas face and in the membrane near the gas face, whereby the gel communicates between the nutrient face and the biolayer and allows diffusion of a nutrient solution through the nutrient face to the biolayer.

In another embodiment the membrane has a nutrient face and a gas face, and comprises a fibrous support material having a nanoporous solid or gel therein and/or thereon. The nanoporous solid or gel may be silica gel, titania gel, zirconia gel, alumina gel or a mixed gel comprising two or more of silica, titania, zirconia and alumina (e.g. silica-alumina gel), or it may comprise agar agar, agarose, calcium alginate, pectin or other biopolymer. One process for making a membrane according to this embodiment comprises the steps of:
- infusing a precursor liquid into the support material, said precursor liquid being capable of generating the nanoporous solid or gel; and
- generating the nanoporous solid or gel on and/or in the support material to form a membrane.

The process may also comprise the step of exposing the support material to an alkaline aqueous solution, an acidic aqueous solution, an acidic gas, or to a water plasma prior to the step of infusing. The precursor liquid may be for example colloidal silica, or a solution or a suspension of calcium alginate or agar agar or agarose or pectin or another natural or synthetic polymer, or a mixture of these. The process of infusing may comprise immersing the support material in the precursor liquid followed by removing the support material from the liquid, or it may comprise flowing the liquid past the support material, or it may comprise some other suitable method for infusing. The process of generating the nanoporous solid or gel will depend on the nature of the precursor liquid, but may for example comprise evaporating at least a part of the precursor liquid infused in the support material, changing the pH of the precursor liquid infused in the support, changing the temperature of the precursor liquid in the support material or exposing the precursor liquid in the support material to a precipitant in order to precipitate the nanoporous solid or gel on and/or in the support material.

In another embodiment the membrane has a nutrient face and a gas face, and comprises:
- a fibrous support material having a nanoporous solid or gel therein and/or thereon, and
- an immobilised biolayer on the gas face and/or in the membrane near the gas face, wherein the membrane is capable of allowing diffusion of a nutrient solution from the nutrient face to the immobilised biolayer without the external application of pressure, and wherein the membrane is accessible so as to enable removal of cells from the immobilised biolayer. The membrane may have no support matrix on the gas face thereof.

In a second aspect of the invention there is provided a bioreactor comprising:
- a membrane-supporting structure; and
- a membrane according to the first aspect of the invention supported on the membrane-supporting structure.

The membrane-supporting structure may support the membrane in a configuration in which a portion of the membrane is parallel to another portion of the membrane so as to define an inside region between the two portions. The membrane-supporting structure may support more than one membrane. If the bioreactor comprises more than one membrane, the membranes may be parallel to each other or they may be non-parallel to each other. Two or more planar membranes may be arranged in pairs so that each pair is joined so as to form a pouch or a flattened tube or some other shape which defines an inside region between the two membranes of the pair. The membrane may be configured so as to separate a gas at the gas face from a nutrient solution at the nutrient face. The bioreactor may have one or more spacers for maintaining a distance between the membranes, or between different portions of the membrane. The spacers may prevent nutrient liquid from leaking from the sides of the membranes.

The bioreactor may have an inlet for admitting the nutrient solution to the nutrient face of the membrane, and may also have an outlet for removing the nutrient solution from the nutrient face. The inlet may be connected to an inlet manifold and the outlet may be connected to an outlet manifold.

There may also be a recycling system for recycling a liquid, for example the nutrient solution, from the outlet to the inlet. The recycling system may be capable of preventing access of oxygen to the liquid. The recycling system may comprise one or more of a pump, a feed line, a feed line valve, an exit line, an exit line valve, a feed tank and an exit tank.

The bioreactor may additionally comprise a vessel which at least partially encloses the membrane, and may also at least partially enclose the membrane-supporting structure. The vessel may be sterilisable and may have a gas inlet for admitting a gas to the vessel, and a gas outlet for allowing the gas to exit the vessel. The bioreactor may comprise a housing for housing the membrane, and optionally also the membrane supporting structure. The housing may be sterilisable, and may have a gas inlet and a gas outlet. The membrane, and optionally the membrane-supporting structure may be removable from the vessel or the housing. A sterilisable housing may be useful for preventing contamination of the biolayer, the membrane or of other portions of the bioreactor.

There may optionally also be an oxygen remover for removing oxygen from the nutrient solution. The oxygen remover may be a deoxygenator or a degasser, for example a vacuum degasser, or it may comprise a sparge device for bubbling a gas having very little oxygen through the nutrient solution.

The bioreactor may have means for removing solid matter from the membrane. The solid matter may be for example a product of the bioreactor or it may be a portion of the biolayer. The means for removing may comprise a shaker, a scraper, a blower or some other suitable means.

In an embodiment the bioreactor comprises:
a membrane-supporting structure;
a pair of membranes according to the first aspect, said membranes being supported vertically by the membrane-supporting structure, each membrane being oriented relative to the other membrane of the pair so as to define an inside region between the pair of membranes; and
an immobilised biolayer on the gas face of each of the membranes of the pair, and/or in each of the membranes of the pair near the gas face thereof.

The membranes may be planar, or they may be tubular. Each membrane may be oriented relative to the other membrane of the pair so as to form a pouch or a flattened tube or an annulus, or may be oriented in some other configuration that defines an inside region between the membranes of the pair. The membranes of the pair may be joined or they may be unjoined. The nutrient face may adjoin the inside region of the pair of membranes. There may be at least one spacer for maintaining a specified distance between the two membranes of the pair.

The bioreactor may comprise more than one pair of membranes. The more than one pair may be connected in parallel or in series, or some may be in parallel and some may be in series.

In another embodiment the bioreactor comprises:
a membrane-supporting structure;
a tubular membrane according to the first aspect, said membrane being supported vertically by the membrane-supporting structure; and
an immobilised biolayer on the gas face and/or in the membrane near the gas face.

The nutrient face may be on the inside of the tubular membrane and the gas face may be on the outside thereof. The tubular membrane may have at least one spacer for maintaining a distance between opposite faces of the tubular membrane. The tubular membrane may have an inside support concentric with the tubular membrane, such that an inside region is defined between the tubular membrane and the inside support. In that case there may be at least one spacer for maintaining a distance between the tubular membrane and the inside support. The bioreactor may have more than one tubular membrane. The more than one tubular membrane may be connected in parallel or in series, or some may be in parallel and some may be in series.

In another embodiment of the invention the bioreactor comprises:
a membrane-supporting structure;
a planar membrane according to the first aspect, said membrane being supported by the membrane-supporting structure in a configuration in which a portion of the membrane is parallel to another portion of the membrane so as to define an inside region between the two portions;
an immobilised biolayer on the gas face of the membrane and/or in the membrane near the gas face thereof.

The nutrient face of the membrane may adjoin the inside region. There may be at least one spacer for maintaining a distance between the two portions of the membrane.

In another embodiment the bioreactor comprises:
a membrane-supporting structure;
a planar membrane according to the first aspect, said membrane being supported by the membrane-supporting structure in a configuration in which the membrane separates air at the gas face from a nutrient liquid at the nutrient face, and in which the membrane defines a plurality of inner regions whereby the inner regions abut the nutrient face,
an immobilised biolayer on the gas face of the membrane and/or in the membrane near the gas face thereof,
a plurality of inlets for admitting the nutrient solution to the inside regions, said inlets being connected to an inlet manifold,
a plurality of outlets for removing the nutrient solution from the inside regions,
a recycling system for recycling the nutrient solution from the outlets to the inlet manifold,
a scraper for removing solid matter from the membrane, and
a sterilisable housing for housing the membrane and the membrane support structure, said housing having an air inlet and an air outlet.

The sterilisable housing may be for example a green-house or a glass-house, or a chamber, and the chamber be capable of admitting light to the biolayer.

In a third aspect of the invention there is provided a process for making a membrane having an immobilised biolayer on a gas face thereof and/or in the membrane near the gas face, comprising the steps of:

immobilizing biological matter on and/or in a membrane away from a nutrient face of the membrane, said membrane being capable of allowing diffusion of a nutrient solution from the nutrient face to the biological matter; and providing the nutrient solution to the nutrient face of the membrane and exposing the gas face of the membrane to a gas under such conditions that the biological matter forms an immobilised biolayer on the gas face and/or in the membrane near the gas face, wherein the membrane is accessible so as to enable removal of cells from the immobilised biolayer once formed. The membrane may have no support matrix on the gas face thereof.

The gas may be a gas containing oxygen, for example air or oxygen or a mixture of oxygen with some other gas such as nitrogen, carbon dioxide or helium. The gas is preferably not damaging to the membrane.

The biological matter may comprise cells, spores or other biological matter. The cells may be prokaryotic or eukaryotic cells, and may be for example fungi, bacteria, protozoa or plant or animal cells. The animal cells may be for example mammalian cells. The biolayer may be capable of producing pharmaceuticals, antibodies, vaccines, food materials, cells or other substances.

The nutrient solution contains nutrients for the biological matter, the nature of which will depend on the nature of the biological matter. The nutrient solution may also comprise one or more other components such as electrolytes, salts, buffers, compounds for bioconversion or biodegradation etc. The nutrient solution may be substantially anoxic.

The membrane may be planar or may be tubular. The membrane may be nanoporous, mesoporous or microporous or may have a combination of nanoscale and/or mesoscale and/or microscale pores. The membrane may comprise a support material, for example a woven or non-woven fibrous material or a non-fibrous porous material. The support material may have a nanoporous solid or gel therein and/or thereon. The membrane may be made of a material, or materials, that is (are) not biodegradable under the operating conditions of the bioreactor. The membrane may be capable of allowing diffusion of a nutrient solution from the nutrient face to the biological matter without the external application of pressure.

During the step of providing the nutrient solution to the nutrient face of the membrane, some of the biological matter may grow on the nutrient face of the membrane. Consequently, during this step it may be advantageous to move a scraper across the nutrient face. The moving may be continuous or intermittent. The moving may dislodge biological matter from the nutrient face, and may prevent the nutrient faces of adjoining membranes from adhering to each other due to growth of the biological matter. The scraper may be a spacer for separating the nutrient faces of adjoining membranes.

The step of immobilising may comprise exposing the membrane to a plurality of cells and/or spores such that at least some of the plurality of cells and/or spores become attached thereto. Said exposing may comprise exposing the membrane to a carrier containing the cells and/or spores, wherein the carrier may be a liquid, for example an aqueous liquid, or a gas, a vapour, an aerosol or a spray. Said exposing may comprise spraying, irrigating, swabbing, blowing or any other method of exposing that conveys the cells and/or spores to the gas face.

The step of providing the nutrient solution may comprise removing oxygen from the nutrient solution. The step of removing oxygen may comprise degassing, for example by application of a vacuum to the nutrient solution, or it may comprise bubbling a gas having very little oxygen through the nutrient solution.

In an embodiment the step of immobilising comprises the steps of:

infusing a precursor liquid into the support material, said precursor liquid being capable of generating a nanoporous solid or gel; and generating the nanoporous solid or gel on and/or in the support material to form a membrane.

The step of immobilising may also comprise the step of exposing the support material to either an alkaline aqueous solution or to a water plasma prior to the step of infusing. The precursor liquid may comprise biological matter, for example a plurality of cells and/or spores, whereby the process of generating the nanoporous solid or gel immobilizes at least some of the biological matter (e.g. cells and/or spores) within the membrane. The step of immobilising may additionally comprise exposing the membrane to a plurality of cells and/or spores as described earlier. The precursor liquid may be for example colloidal silica, or a solution or a suspension of calcium alginate or agar agar or agarose or pectin or another natural or synthetic polymer, or a mixture of these. The process of infusing may comprise immersing the support material in the precursor liquid followed by removing the support material from the liquid, or it may comprise flowing the liquid past the support material, or it may comprise some other suitable method for infusing. The process of generating the nanoporous solid or gel will depend on the nature of the precursor liquid, but may for example comprise evaporating at least a part of the precursor liquid infused in the support material, changing the pH of the precursor liquid infused in the support, changing the temperature of the precursor liquid in the support material or exposing the precursor liquid in the support material to a precipitant in order to precipitate the nanoporous solid or gel on and/or in the support material.

In another embodiment there is provided a process for making a membrane having an immobilised biolayer on a gas face thereof and/or in the membrane near the gas face, comprising the steps of infusing a precursor liquid into a support material, said precursor liquid being capable of generating a nanoporous solid or gel;

generating the nanoporous solid or gel on and/or in the support material to form the membrane;

exposing the gas face of the membrane to a plurality of cells and/or spores such that at least some of the plurality of cells and/or spores become attached thereto; and providing a nutrient solution to a nutrient face of the membrane and exposing the gas face of the membrane to a gas under such conditions that the cells and/or spores forms an immobilised biolayer on the gas face and/or in the membrane near the gas face.

In another embodiment there is provided a process for making a membrane having an immobilised biolayer on a gas face thereof and/or in the membrane near the gas face, comprising the steps of infusing a precursor liquid into a support material, said precursor liquid containing biological matter, and being capable of generating a nanoporous solid or gel;

generating the nanoporous solid or gel on and/or in the support material to form the membrane, thereby immobilising the biological matter on and/or in the membrane; and providing a nutrient solution to a nutrient face of the membrane and exposing the gas face of the membrane to a gas under such conditions that the biological matter forms an immobilised biolayer on the gas face and/or in the membrane near the gas face.

In another embodiment there is provided a process for making a membrane having an immobilised biolayer on a gas face thereof and/or in the membrane near the gas face, comprising the steps of infusing colloidal silica into a woven support material, said colloidal silica containing cells and/or spores;

acidifying the colloidal silica in the support material to form the membrane, thereby immobilising the cells and/or spores in the membrane; and providing a nutrient solution to a nutrient face of the membrane and exposing the gas face of the membrane to a gas under such conditions that the cells and/or spores form an immobilised biolayer on the gas face and/or in the membrane near the gas face.

There is also provided a membrane having an immobilised biolayer on a gas face thereof and/or in the membrane near the gas face, said membrane being made by the process of the third aspect of the invention.

In a fourth aspect of the invention there is provided a process for making a bioreactor comprising the step of mounting a membrane according to the first aspect of the invention on a membrane-supporting structure.

In an embodiment, the process comprises mounting a membrane according to the first aspect of the invention on a membrane-supporting structure, said membrane having an immobilised biolayer on the gas face and/or in the membrane near the gas face, and said membrane being capable of allowing diffusion of a nutrient solution from the nutrient face to the immobilised biolayer, whereby the membrane is accessible so as to enable removal of cells from the immobilised biolayer. The membrane may have no support matrix on the gas face thereof.

In another embodiment, the process comprises the steps of:

mounting a membrane on a membrane-supporting structure, said membrane having biological matter immobilised thereon and/or therein away from a nutrient face of the membrane, said membrane being capable of allowing diffusion of a nutrient solution from the nutrient face to the biological matter, and said membrane being accessible so as to enable removal of cells from the immobilised biolayer; and providing the nutrient solution to the nutrient face of the membrane and exposing the gas face of the membrane to a gas under such conditions that the biological matter forms an immobilised biolayer on the gas face and/or in the membrane near the gas face.

The nutrient solution may be substantially anoxic. The membrane may have no support matrix on the gas face thereof.

In another embodiment the process comprises the steps of:

mounting a membrane on a membrane-supporting structure, said membrane:

having a nutrient face and a gas face, and being capable of supporting an immobilised biolayer on the gas face and/or in the membrane near the gas face, being capable of allowing diffusion of a nutrient solution from the nutrient face to the immobilised biolayer; and immobilising biological matter on and/or in the membrane away from the nutrient face; and providing the nutrient solution to the nutrient face of the membrane and exposing the gas face of the membrane to a gas under such conditions that the biological matter forms an immobilised biolayer on the gas face and/or in the membrane near the gas face whereby the membrane is accessible so as to enable removal of cells from the immobilised biolayer. The membrane may have no support matrix on the gas face thereof.

The step of immobilising may comprise exposing the membrane to a plurality of cells and/or spores such that at least some of the plurality of cells and/or spores become attached thereto. Said exposing may comprise exposing the membrane to a carrier containing the cells and/or spores, wherein the carrier may be a liquid, for example an aqueous liquid, or a gas, a vapour, an aerosol or a spray. Said exposing may comprise spraying, irrigating, swabbing, blowing or some other method of exposing that conveys the cells and/or spores to the gas face. The nutrient solution maybe substantially anoxic.

In another embodiment the process comprises the steps of:

mounting a support material on a membrane-supporting structure infusing a precursor liquid into the support material, said precursor liquid being capable of generating a nanoporous solid or gel;

generating the nanoporous solid or gel on and/or in the support material to form a membrane; and providing a nutrient solution to a nutrient face of the membrane and exposing a gas face of the membrane to a gas under such conditions that an immobilised biolayer forms on the gas face and/or in the membrane near the gas face, whereby the membrane is accessible so as to enable removal of cells from the immobilised biolayer. The membrane may have no support matrix on the gas face thereof.

In the process of this embodiment, either:

the precursor liquid comprises a plurality of cells and/or spores, whereby the step of generating the nanoporous solid or gel immobilizes at least some of the cells and/or spores within the membrane; or the step of exposing the membrane to a plurality of cells and/or spores (as described earlier) is performed before the step of providing a nutrient solution; or both.

The nutrient solution may be substantially anoxic.

In a fifth aspect of the invention there is provided a method for operating a bioreactor according to the second aspect comprising:

exposing the nutrient face of the membrane to a nutrient solution, exposing the biolayer to a gas, and allowing the nutrient solution to diffuse from the nutrient face of the membrane to the biolayer.

The step of allowing the nutrient solution to diffuse may be performed without the application of external pressure. The method may also comprise passing the gas past the biolayer. The gas may be a gas containing oxygen, for example air or oxygen or a mixture of oxygen with some other gas such as nitrogen, carbon dioxide or helium, if the biolayer comprises aerobic species. The gas is preferably not damaging to the membrane. The nutrient solution contains nutrients for the biolayer, the nature of which will depend on the nature of the biolayer. The nutrient solution may also comprise one or more other components such as electrolytes, salts, buffers etc. The nutrient solution may be substantially anoxic. The method may be a batch method wherein the nutrient solution does not flow past the membrane, or it may be a continuous method, wherein the nutrient solution flows past the membrane. The method for operating the biomembrane reactor may be for the purpose of producing for example pharmaceuticals, antibodies, vaccine components, food material, cells or enzymes or it may be for the purpose of removing, degrading or converting undesirable components in the nutrient liquid.

The method may also comprise the step of removing oxygen from the nutrient solution. The step of removing oxygen may comprise degassing, for example by application of a vacuum to the nutrient solution, or it may comprise bubbling a gas having very little oxygen through the nutrient solution. The step of removing oxygen may be performed before the step of exposing the nutrient face to the nutrient solution.

The method may additionally comprise the step of isolating a product of the bioreactor. Said isolating may comprise separating the product from the nutrient solution, or it may comprise harvesting solid matter from the gas face. The solid matter may be for example a product of the bioreactor or it may be a portion of the biolayer. The solid matter may comprise for example cells, spores, hyphae or other biological matter including substances produced by the cells such as proteins, polysaccharides, and polymers.

In an embodiment, the method comprises the steps of:
exposing the nutrient face of a membrane to a nutrient solution, said membrane having an immobilised biolayer on the gas face thereof and/or in the membrane near the gas face, said membrane being accessible so as to enable removal of cells from the immobilised biolayer,
exposing the biolayer to a gas containing oxygen,
allowing the nutrient solution to diffuse from the nutrient face of the membrane to the biolayer,
exposing the membrane to the nutrient solution for a first period of time,
introducing a second liquid to the nutrient face of the membrane,
exposing the membrane to the second liquid for a second period of time, and
separating a product from the second liquid.

The membrane may have no support matrix on the gas face thereof. The second liquid may be a liquid that does not contain nutrient, and may be for example a saline solution or a buffer solution. The first period of time may be for example between about 1 hour and 1 day, and the second period of time may be for example between about 12 hours and 12 days.

In another embodiment, the method comprises the steps of:
exposing the nutrient face of a membrane to a nutrient solution, said membrane having an immobilised biolayer on the gas face thereof and/or in the membrane near the gas face, said membrane being accessible so as to enable removal of cells from the immobilised biolayer,
exposing the biolayer to a gas containing oxygen, and
separating a product from the nutrient solution.

The membrane may have no support matrix on the gas face thereof.

In yet another embodiment, the method comprises the steps of:
exposing the nutrient face of a membrane to a nutrient solution, said membrane having an immobilised biolayer on a gas face thereof and/or in the membrane near the gas face, said membrane being accessible so as to enable removal of cells from the immobilised biolayer,
allowing the nutrient solution to diffuse from the nutrient face to the biolayer,
exposing the biolayer to a gas containing oxygen, and
removing a solid product from the biolayer.

The membrane may have no support matrix on the gas face thereof. The step of removing may comprise scraping or shaking or blowing or some other suitable means for separating the solid product from the biolayer.

There is also provided a bioreactor according to the invention when used with a substantially anoxic nutrient solution at the nutrient face thereof to produce a biolayer on the gas face thereof and/or in the membrane near the gas face thereof, or to produce a product of a biolayer on the gas face thereof and/or in the membrane near the gas face thereof. The product may be for example pharmaceuticals, antibodies, vaccine components, food materials, cells or other substances, or the bioreactor may convert substances from the solution into useful or non-toxic forms.

BRIEF DESCRIPTION OF THE DRAWINGS

A preferred form of the present invention will now be described by way of example with reference to the accompanying drawings wherein:

FIG. 16 shows a graph of carbohydrate consumption and of pH in a continuous bioreactor of example 3 and, for reference, results for a batch system using the same membrane materials

FIG. 18 shows a graph of concentration of various elements over time showing removal of those elements from malt extract broth by *A. niger* grown in an NMB in example 4;

DETAILED DESCRIPTION OF THE PREFERRED EMBODIMENTS

Figure 1:
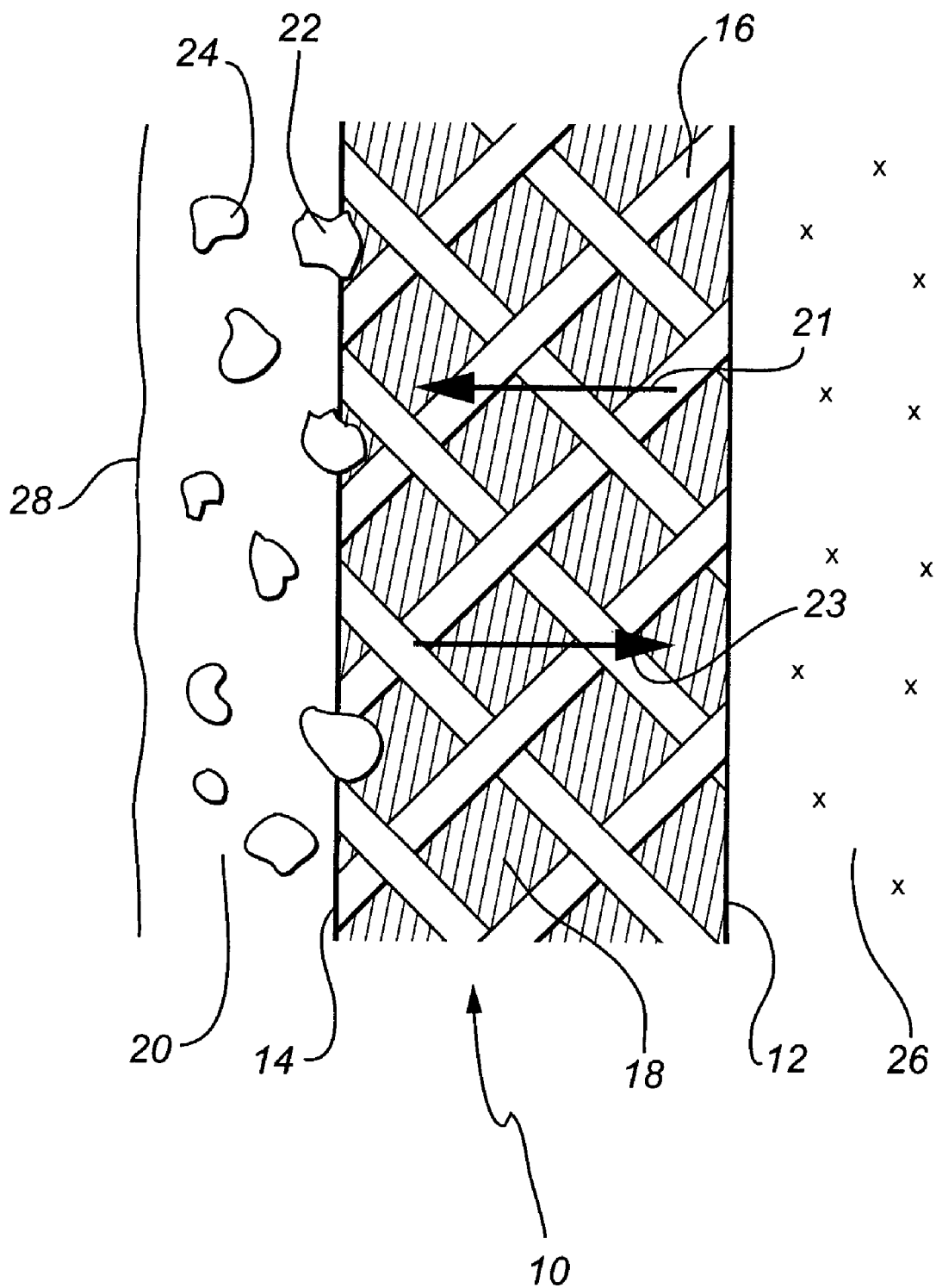
FIG. 1 is a diagrammatic representation a membrane according to the invention.

The bioreactor of the present invention may be a membrane bioreactor, a nanoparticulate membrane bioreactor, a hybrid organ or an organoid. The bioreactor may be, but is not limited to, an apparatus for producing biomass, or an apparatus for producing chemical substances, or an apparatus for removing pollutants. The bioreactor comprises a membrane of porous or fibrous material optionally having a nanoparticulate gel, for example a silica gel, thereon and/or therein, and supported by a membrane-supporting structure. The bioreactor may have one or more membranes and may have between about 1 and 20000 membranes, or between about 1 and 1000 or between about 1 and 100 or between about 1 and 50 or between about 1 and 20 or between about 1 and 10 or between about 100 and 20000 or between about 1000 and 20000 or between about 10000 and 20000 or between about 2 and 10000 or between about 10 and 5000 or between about 20 and 1000 or between about 50 and 500 or between about 100 and 200, and may have about 1, 2, 3, 4, 5, 6, 7, 8, 9, 10, 12, 14, 16, 18, 20, 30, 40, 50, 60, 70, 80, 90, 100, 120, 140, 160, 180, 200, 250, 350, 400, 450, 500, 600, 700, 800, 900, 1000, 1500, 2000, 2500, 3000, 3500, 4000, 4500, 5000, 6000, 7000, 8000, 9000, 10000, 12000, 14000, 16000, 18000 or 20000 membranes. Each membrane may have an area of between about 10 $cm^2$ and 10 $m^2$, and may have an area of between about 10 $cm^2$ and 1 $m^2$, or between about 10 and 500 $cm^2$, 10 and 100 $cm^2$, 10 and 50 $cm^2$, 100 and 500 $cm^2$, 500 $cm^2$ and 1 $m^2$, 1 and 10 $m^2$, 1 and 5 $m^2$, 5 and 10 $m^2$ or 500 $cm^2$ and 5 $m^2$, and may have an area of about 10, 50, 100, 200, 300, 400, 500, 600, 700, 800 or 900 $cm^2$, or about 1, 1.5, 2, 2.5, 3, 3.5, 4, 4.5, 5, 6, 7, 8, 9 or 10 $m^2$, or may have an area of greater than 10 $m^2$, for example 15, 20, 25 or 30 $m^2$ or more. If the membranes are planar membranes, they may be arranged in pairs, or gills. There may be between about 1 and 10000 pairs or may be between about 1 and 5000 or between about 1 and 1000 or between about 1 and 500 or between about 1 and 100 or between about 1 and 50 or between about 1 and 10, or between about 2 and 10000 or between about 5 and 5000 or between about 10 and 1000 or between about 50 and 500 or between about 100 and 200 or between about 100 and 10000 or between about 500 and 10000 or between about 1000 and 10000 or between about 5000 and 10000 pairs, and may be about 1, 2, 3, 4, 5, 6, 7, 8, 9, 10, 12, 14, 16, 18, 20, 25, 30, 35, 40, 45, 50, 60, 70, 80, 90, 100, 200, 300, 500, 500, 600, 700, 800, 900, 1000, 1500, 2000, 2500, 3000, 3500, 4000, 4500, 5000, 6000, 7000, 8000, 9000, 10000, 12000, 14000, 16000, 18000 or 20000 pairs. In one embodiment, a pair of membranes, i.e. a gill, is suspended parallel to each other in a vertical orientation. The membranes may be planar, so that the pair is in the form of a flattened tube, or they may be tubular and concentric, so that the pair defines an annular region between them. The pair of membranes may be joined around at least a portion of the circumferential edges thereof in order to define a lumen between the membranes. In another embodiment a membrane tube is suspended with appropriate spacers. Thus the present invention provides a bioreactor comprising two substantially planar membranes disposed parallel and in close proximity to each other, such that they define a planar lumen between them, said lumen housing a liquid stream. The faces of the membranes away from the lumen may have a biolayer (i.e. biofilm) therein and/or thereon. The membranes, and the lumen are oriented vertically such that the liquid stream is transported downwards through the lumen under the force of gravity. The two membranes may be joined at the edges thereof to form a pouch structure. There may be another spacer located between the membranes in the form of a scraper, which may be a vertical member, for example a rod or a bar. It may have holes therein so that when it moves, the nutrient solution in the region between the membranes can pass through the holes. This spacer may be movable, and may be capable of moving between the membranes. It may be disposed so that, when moved, it is capable of scraping the nutrient faces of the membranes. It may be disposed so that, when moved, it can remove cells adhering to the nutrient faces of the membranes. The spacer may be in the form of a scraper, which may be a vertical member, for example a rod or a bar. It may be coupled to a spacer moving device for moving the spacer so as to remove cells adhering to the nutrient faces of the membranes. This movable spacer may also aid the process of formation of two separate membranes doped with gels, by breaking the gel layer that would otherwise stick the two membranes together and thus preventing the formation of a lumen. In still another embodiment a membrane tube is located concentrically (either inside or outside) in relation to a support, with spacers to maintain a distance between the membrane and the support. In a further embodiment a membrane is configured so that a portion of the membrane is parallel to another portion of the membrane so as to define an inside region between the two portions. For example the membrane may be concertinaed. The membranes may be doped with appropriate biological matter for example by including the biological matter with a precursor liquid during fabrication of the membrane, or the membranes may be inoculated with the biological matter after the membrane has been fabricated.

The membranes may be connected in parallel or in series, or some may be in parallel and some may be in series. In a series connection, an outlet for removing liquid from the nutrient face(s) of a first (pair of) membrane(s) is connected to an inlet for supplying liquid to the nutrient face(s) of a second (pair of) membrane(s). There may be a pump for pumping fluid from the outlet to the inlet. In a parallel connection, the inlets for supplying liquid to the nutrient faces of the membranes are connected to an inlet manifold, and the outlets for removing liquid from the nutrient faces of the membranes may be connected to an outlet manifold.

The membranes may be oriented vertically, or non-horizontally, or at a non-zero angle to the horizontal, and may separate a nutrient region (e.g. a lumen) or regions (adjoining the nutrient face or faces of the membranes) from a gas region or regions (adjoining the gas face of faces of the membranes).

The nutrient solution may be supplied from above the membrane(s) and may flow down the nutrient face(s) of the membranes. It may passed to the membrane by way of a nozzle or some other inlet device. It may be sprayed onto the membrane using a spray which comprises the nutrient solution and a substantially anoxic gas. The angle of the membranes to the horizontal may be between about 30 and 90°, or between about 45 and 90, 60 and 90 or 45 and 60, and may be about 30, 45, 60, 75 or 90°. The membranes may be disposed between the nutrient solution at the nutrient face and the gas at the gas face, the nutrient solution and the gas both being in contact with the membrane. The pressure of the gas at the gas face may be sufficient that the nutrient solution does not pass through the membrane into the gas region. The pressure may be the same as or greater than the pressure of the nutrient solution at the nutrient face. The pressure may be between about 0.8 and 1.2 atm, or between about 0.9 and 1.1, 0.9 and 1 or 1 and 1.1 atm, and may be about 0.8, 0.9, 1, 1.1 or 1.2 atm. The pressure across the membrane may be less than about 0.2 atm, or less than about 0.15, 0.1, 0.1 or 0.05 atm., and may be about 0, 0.05, 0.1, 0.15 or 0.2, or between about 0 and 0.2, 0 and 0.1, 0 and 0.05 or 0.05 and 0.15 atm, or may be greater than 0.2 atm under some circumstances.

The membrane of the present invention may be used in many orientations. If the biolayer of the membrane comprises aerobic cells or microorganisms or spores, then the nutrient side of the membrane should be substantially anoxic, and the gas side should have a gas containing oxygen in contact therewith. The gas containing oxygen may have between about 5 and 100% w/w oxygen, or between about 10 and 100, 15 and 100, 20 and 100, 30 and 100, 50 and 100, 75 and 100, 10 and 50, 10 and 30, 10 and 20, 15 and 50, 15 and 25 or 20 and 50% w/w oxygen, and may contain about 10, 15, 20, 25, 30, 35, 40, 45, 50, 55, 60, 65, 70, 75, 80, 85, 90, 95 or 100% w/w oxygen. As noted earlier, in one orientation a pair of membranes defines a lumen therebetween. Nutrient solution flowing down the lumen is depleted of oxygen as the biolayer absorbs oxygen from the nutrient solution, leaving it substantially anoxic. The nutrient solution may be deoxygenated using a deoxygenator prior to flowing down the lumen. In another orientation, the membrane separates two chambers, wherein a first gas chamber has a gas containing oxygen, which is exposed to the gas face of the membrane and the second chamber is anoxic, and is exposed to the nutrient face of the membrane. The second chamber may be filled with nutrient solution, which may be static or may flow past the membrane. The second chamber may have an anoxic gas above the nutrient solution, or the nutrient solution may flow down the nutrient face of the membrane within the second chamber, said second chamber having an anoxic gas therein so that the nutrient solution within the second chamber is anoxic. The nutrient solution may be sprayed onto the membrane in the second chamber, using an anoxic gas for said spraying. The first chamber may be an upper chamber and the second chamber may be a lower chamber, or the first chamber may be a lower chamber and the second chamber may be an upper chamber (whereby the membrane is horizontal), or the first and second chambers may be side by side, whereby the membrane is vertical. In the case of a horizontal membrane, particularly if the second chamber is an upper chamber, there may be a support structure for supporting the membrane so that the weight of the nutrient solution does not distort or damage the membrane. Alternatively there may be no first chamber, wherein the gas face of the membrane is open to the atmosphere, which contains oxygen. It may be advantageous to pass a gas containing a higher than ambient concentration of oxygen past the gas face of the membrane in order to encourage growth of the biolayer. In another orientation the membrane is horizontal and separates an upper chamber, having a gas containing oxygen in contact with the gas face of the membrane, from a lower chamber, having the nutrient solution in contact with the nutrient face of the membrane, wherein the nutrient solution is anoxic. The nutrient solution may be anoxic as a result of being deoxygenated using a deoxygenator. Alternatively, if the lower chamber has a small volume, oxygen may be depleted in the nutrient solution in the lower chamber by being consumed by the biolayer of the membrane. One or both of the nutrient solution and the gas containing oxygen may flow past the membrane. In another orientation the membrane may be disposed close to and parallel to a solid surface (which may be for example a polymeric material or a metal such as stainless steel, aluminium etc.) such that a lumen is defined between the membrane and the solid surface. The membrane may be vertical or it may be at an angle to the horizontal as defined above. Nutrient solution flowing down the lumen is depleted of oxygen as the biolayer absorbs oxygen from the nutrient solution, leaving it substantially anoxic. The nutrient solution may be deoxygenated using a deoxygenator prior to flowing down the lumen. In another orientation the membrane forms a portion of the wall of a nutrient chamber, whereby the gas face of the membrane is on the outside of the nutrient chamber and the nutrient face is on the inside of the nutrient chamber. The nutrient chamber is maintained anoxic by means of a deoxygenator as describe elsewhere herein. In cases where the nutrient solution flows past the membrane, it may flow under the influence of gravity, or by being pumped, or a portion of the bioreactor comprising the membrane may be rotated so as to cause the nutrient solution to flow past the membrane under the influence of centrifugal force, or it may flow past under some other force. In cases where the membrane is not horizontal, the nutrient solution may flow past the membrane from above or from below, or in some other direction. In another orientation, the nutrient liquid may flow past the membrane, which is in a non-horizontal, optionally vertical, orientation. In this orientation, the nutrient liquid may flow past the membrane within a nutrient chamber from a lower portion of the membrane to an upper portion of the membrane. This enables easy exclusion of gas from the nutrient chamber, thereby facilitating the maintenance of anoxic conditions at the nutrient face of the membrane. In some modes of operation of a bioreactor of the present invention, in addition to the biolayer on the membrane, there may be anaerobic cells encapsulated in beads which are in the nutrient solution. Thus nutrient may be metabolised by both encapsulated anoxic cells in the anoxic nutrient solution and by oxygen requiring cells and/or spores of the biolayer on the membrane. The beads may be sufficiently small as to avoid clogging, and may have a specific gravity adequate to remain in suspension in the nutrient solution. The size of the beads may be between about 1 and 100 microns, or between about 1 and 50, 1 and 10, 10 and 100, 50 and 100 or 10 and 50 microns, and may be about 1, 2, 3, 4, 5, 10, 15, 20, 30, 40, 50, 60, 70, 80, 90 or 100 microns, or may be larger or smaller, dependent in part on the size of the cells that are encapsulated therein. The specific gravity of the beads may be between about 0.8 and 1.2, or between about 0.8 and 1, 1 and 1.2 or 0.9 and 1.1, and may be about 0.8, 0.9, 1, 1.1 or 1.2, or may be greater or smaller, depending in part on the specific gravity of the nutrient solution. The encapsulated anaerobic cells may be encapsulated by an encapsulant which may be a gel or a porous material, that allows access of the nutrients in the nutrient solution to the encapsulated anaerobic cells. The encapsulant may be a hydrogel, an inorganic gel, an organic gel, a porous ceramic, a porous polymer or some other encapsulant permeable to the nutrient. In this mode, the beads may be recycled past the membrane, and may be prevented from exiting the bioreactor. This may be achieved for example by use of a filter. By encapsulating the anaerobic cells, they may be prevented or inhibited from colonizing the nutrient side of the membrane, and therefore from restricting diffusion of the nutrient solution through the membrane to the biolayer on the gas face of the membrane.

In any or all of the above orientations and modes, the membrane may be maintained in that orientation by means of a membrane-supporting structure, for example a support frame, a casing, a housing, a framework, a scaffold or some other support structure. The membrane may be mounted such that it hangs from the membrane supporting structure, or it may be constrained within the membrane supporting structure, or it may be mounted in some other manner in or on the membrane supporting structure. The membrane-supporting structure may comprise a solid structure having grooves or channels therein, whereby the membrane spans the grooves to enclose the nutrient solution therein. Thus in operation of the latter option, the gas side of the membrane having the biolayer thereon is away from the grooves, and the nutrient side of the membrane faces the grooves. Nutrient solution flowing through the grooves diffuses through the nutrient face to the biolayer and metabolites diffuse to the grooves. In this option, the membrane may have an internal support, e.g. woven, fibrous or other support, or may have no internal support. It may have for example fibres therein to provide additional support. The grooves may span the solid support and have gel membrane on two opposing sides of each groove. The membrane supporting structure may provide sufficient support for the membrane to maintain its integrity. In any or all of the above orientations, the nutrient solution may be circulated past the membrane using a recycling system. The recycling system may be capable of excluding oxygen from the nutrient solution, or of removing oxygen from the nutrient solution for example using a deoxygenator.

In waste water and similar applications, it may be necessary to recycle the waste (the nutrient solution) past the membrane of the bioreactor more than one time, in order to achieve sufficient contact time to remove the desired amount of matter in the waste. The contact time may be between about 1 minute and 10 days, depending on the nature of the biolayer, the nature and concentration of the matter to be removed and other factors. The contact time may be between about 1 minute and 1 day, 1 minute and 12 hours, 1 minute and 1 hour 1 and 30 minutes, 1 and 15 minutes, 1 hour and 10 days, 1 and 10 days, 5 and 10 days, 1 hour and 1 day, 1 and 12 hours 12 and 24 hours or 6 and 12 hours, and may be about 1, 2, 3, 4, 5, 6, 12, 18, 24, 30 or 45, minutes, 1, 2, 3, 4, 5, 6 8, 12, 15, 18 or 21 hours, or 1, 2, 3, 4, 5, 6, 7, 8, 9 or 10 days or may be more than 10 days. Accordingly the waste may be recycled past the membrane between about 1 and 1000 times, depending on the dimensions of the membrane, the flow rate, the nature and concentration of the matter to be removed, the nature of the biolayer and other factors. It may be recycled between about 1 and 500, 1 and 200, 1 and 100, 1 and 50, 1 and 10, 10 and 1000, 100 and 1000, 500 and 1000, 10 and 500, 10 and 100, 100 and 500, 50 and 100 or 10 and 50 times, and may be recycled about 1, 2, 3, 4, 5, 10, 15, 20, 25, 30, 35, 40, 45, 50, 60, 70, 80, 90, 100, 200, 3400, 400, 500, 600, 700, 800, 900 or 1000 times. There may be a detector within the recycling system to determine the concentration of the matter to be removed. Thus the waste may be recycled until the matter to be removed has dropped to a predetermined concentration, as determined by the detector. The nature of the detector may depend on the nature of the matter to be removed. It may be a concentration detector, a pH detector, a pH probe, an ion concentration probe or some other type of detector. A bioreactor according to the invention may be used to sequester heavy metals from a stream containing them. It may be a waste stream or some other stream. The heavy metals may if required be recovered from the biolayer in which they were sequestered, for example by extraction, combustion or some other suitable process.

Examples of microorganisms and cells that may be used in the biolayer of the membrane of the present invention include *P. chrysogenum, A. ferrooxidans, A. Niger, A. Oryzae* (e.g. var. *oryzae*, IFO30113 strain), *A. soya*, human primary fibroblasts, A feature of the present invention is that the membrane is accessible so as to enable removal of cells from the immobilised biolayer. The membrane may have no support matrix on the gas face thereof in order that the membrane be accessible. Removal of cells from the immobilised biolayer may be for the purpose of using the cells, for example as food, or it may be to prevent excessive growth of the biolayer. In operation the biolayer may grow to such an extent that the diffusion of oxygen and/or of nutrient solution through the biolayer is slowed, thereby reducing the rate of production of products, or the rate of removal of undesirable components from the nutrient solution. It is therefore desirable to be able to remove some of the biolayer in order to achieve rates of diffusion of oxygen and/or of nutrient solution sufficient for acceptable production or removal rates. The membrane may be accessible to a device for scraping or shaking or blowing or some other suitable means for separating the solid product from the biolayer. Thus the solid product may be removed by a process comprising at least one of scraping or shaking or blowing. Alternatively the solid product may be removed by operating the bioreactor so that the biolayer is not viable, for example by not providing nutrient to the biolayer or by letting the culture consume all of the nutrient. In this case, for certain types of biolayer, the biolayer may spontaneously detach from the membrane, or may become more amenable to removal by scraping or shaking or blowing.

In operation, nutrient solution is supplied to the nutrient face of the membrane to deliver nutrients which diffuse through the membrane to the biolayer, which grows on the gas face of the membrane and to a lesser extent inside the membrane's pore network. Since nearly all of the biomass grows on or in the gas face of the membrane, it is effectively immobilised and thus is separated from the nutrient solution. The relatively anoxic nutrient solution may retard the growth of the cells or other biological matter of the biolayer within the nutrient solution, thus reducing biofouling. The virtually cell-free nutrient solution is easier to process than the cell laden effluent produced by other types of bioreactor. The diffusion of nutrient solution may occur without the need for external pressure. This precludes the need for support structures to support the membrane and the biolayer from pressure from the nutrient face of the membrane, and also precludes the need for equipment to apply such pressure.

In one mode of operation, the biolayer of the bioreactor comprises aerobic microorganisms or cells. In this mode, an oxygen containing gas is provided to the gas face of the membrane, and a nutrient solution comprising oxidizable matter (for example carbohydrates, amino acids, iron(II) salts) is provided to the nutrient face of the membrane in such a manner that the nutrient solution is substantially anoxic. This may be achieved by removing oxygen from the nutrient solution before it is provided to the membrane, or it may be by providing the nutrient solution to the membrane in a configuration such that the biolayer rapidly consumes any oxygen initially present in the nutrient solution, leaving it substantially anoxic thereafter. Depending on the configuration of the bioreactor, the nature of the nutrient solution, the nature of the biolayer etc., oxygen initially present in the nutrient solution may be consumed in the first about 10 cm of the membrane, or the first about 5, 4, 3, 2, 1 or 0.5 cm (or some other length) of the membrane, and the remainder of the membrane would then be exposed to substantially anoxic nutrient solution.

In an alternative mode of operation, the biolayer of the bioreactor comprises anaerobic microorganisms of cells. In this mode, an anoxic gas may be provided to the gas face of the membrane. The anoxic gas may be hydrogen, methane, nitric oxide, nitrogen or some other anoxic gas, or some combination of these. The anoxic gas may be non-oxidising and may be a reducing gas, and may be an oxidisable gas. In this mode, the nutrient stream may comprise reducible matter, such as sulphate, nitrate or a mixture of reducible matter. In operation in this mode, the biolayer reduces the reducible matter of the nutrient stream and oxidizes the anoxic gas. Reduction of the reducible matter may produce insoluble matter (e.g. metal sulfides), for example removing undesirable solutes from the nutrient stream.

In another mode of operation, the membrane has a first biolayer on the gas face of the membrane, said first biolayer comprising aerobic cells or microorganisms, and a second biolayer on the nutrient face of the membrane, said second biolayer comprising anaerobic cells or microorganisms. This mode may be used for example for simultaneous nitrification and denitrification of ammonia and nitrite to form nitrogen. This may be used in wastewater treatment applications and in aquaculture applications.

In operation also, the biomass may be exposed to an oxygen containing gas on the gas side of the membrane. In many bioreactors in the prior art, the biomass is located in the nutrient solution, thereby necessitating oxygenation or aeration of the nutrient solution in order to provide oxygen to the biomass. This greatly increases the cost of these bioreactors. The present bioreactor design obviates the need for such oxygenation or aeration equipment. In bioreactors according to the present invention, pairs of membranes (which define a lumen for passage of a nutrient solution therebetween) may be separated by a space sufficient for passage of air between the pairs of membranes, for providing oxygen to the biomass on and/or in the membranes. The space may be sufficient to allow diffusive flow therethrough. The gas (e.g. air) may be passed through the space by diffusion, convection, wind or some other means, i.e. without the need for additional equipment to cause it to pass through the space, or it may be by means of a fan, a blower, a gas circulator or some other means to cause the gas to pass across the gas faces of the membranes of the pairs. The space may depend on the size of the membranes. It may be between about 2 and 100 mm across (i.e. between the pairs of membranes), or between about 2 and 50, 2 and 20, 2 and 10, 5 and 50, 5 and 20, 5 and 10, 10 and 100, 50 and 100, 80 and 100, 10 and 50, 10 and 20 or 8 and 10 mm, and may be about 2, 3, 4, 5, 6, 7, 8, 9, 10, 15, 20, 25, 30, 35, 40, 45, 50, 55, 60, 65, 70, 75, 80, 85, 90, 95 or 100 mm across, or may be more than 100 mm across.

In many modes of operation the bioreactors of the present invention operate such that the nutrient stream is substantially anoxic. This restricts the growth of oxygen-requiring cells and spores on the nutrient face of the membrane. This feature distinguishes the present invention from many previously known bioreactors, which do not describe an anoxic nutrient solution, and indeed take no precautions to ensure that the nutrient feed stream is anoxic. For example JP10-179138 describes a bioreactor wherein a nutrient stream flows down a membrane which has a biolayer on the other side from the nutrient stream. However in this bioreactor, there are no precautions to prevent oxygenation of the nutrient stream as it is applied to the membrane and flows down it, and there is no indication that it is anoxic. The membrane used in that invention must be impassable to the cells of the biolayer, since this is the only means to prevent the cells growing on the nutrient face of the membrane. In the present invention, by contrast, the absolute integrity of the membrane is not as important, as the cells, spores etc. are inhibited from growing on the nutrient side of the membrane by the anoxic nature of the nutrient solution. This enables use of a less expensive membrane in the present invention relative to that of JP10-179138.

The bioreactor may be operated in a manner that the nutrient solution is not exposed to air. This may be achieved by passing it between two membranes, or between two portions of a single membrane, or between a membrane and a support that is not permeable to oxygen, wherein the support may be located between two parallel membranes, whereby any dissolved oxygen in influent nutrient solution is rapidly used up by the biolayer, leaving the nutrient solution relatively anoxic. In this way the nutrient stream may be rendered largely anoxic without the need for expensive sparging and/or deoxygenating equipment. Alternatively, the nutrient solution may be passed by the membrane in a substantially oxygen-free atmosphere, for example in nitrogen, carbon dioxide, helium, argon or another non-oxidising gas or a mixture thereof. For example the membrane may be suspended vertically, and have an oxygen-containing gas on the gas side, and have nutrient solution trickling down the nutrient side blanketed by a nitrogen atmosphere. There may optionally also be an oxygen remover for removing oxygen from the nutrient solution in order to ensure that it is relatively anoxic. The oxygen remover may be a degasser, for example a vacuum degasser, or it may comprise a sparge device for bubbling a gas having very little oxygen through the nutrient solution. The gas having very little oxygen may be for example nitrogen, carbon dioxide, helium, argon or any other convenient gas that contains little oxygen. It may have less than about 5% oxygen by weight or by volume, or less than about 4, 3, 2, 1, 0.5 or 0.1% oxygen or may have about 0, 0.1, 0.5, 1, 2, 3, 4 or 5% oxygen by weight or by volume. After the nutrient solution exits the oxygen remover, it may have an oxygen concentration of less than about 10 ppm oxygen, or less than about 5, 1, 0.5, 0.1, 0.05 or 0.01 ppm oxygen or may have about 0, 0.01, 0.05, 0.1, 0.5, 1, 5 or 10 ppm oxygen, or it may have an oxygen saturation level of less than about 10%, or less than about 5, 2, 1, 0.5 or 0.1%, or of about 0, 0.1, 0.5, 1, 2, 3, 4, 5, 6, 7, 8, 9 or 10%. The oxygen remover may be located at the inlet, the inlet manifold, the outlet, the outlet manifold or at a reservoir for holding the nutrient solution or in some other part of the bioreactor, or there may be more than one oxygen remover, each being located at any of these locations.

There may also be a recycling system for recycling the nutrient solution from the outlet to the inlet. The recycling system may be capable of preventing access of oxygen to the nutrient solution. The recycling system may comprise one or more of a pump, a pump inlet line, a pump outlet line, a feed line, a feed line valve, an exit line, an exit line valve, a feed tank and an exit tank. For example the recycling system may comprise:
    a pump for pumping the nutrient solution,
    a pump outlet line leading from the pump to the inlet manifold,
    a pump inlet line leading from the outlet manifold to the pump, a feed line with a feed line valve, for allowing entry of liquid into the bioreactor, and an exit line with an exit line valve, for removing fluid from the bioreactor.

The recycling system may have a reservoir for holding the nutrient liquid. The reservoir may be a tank or a container, a beaker, a bottle, a chamber, a cistern or a vessel.

It has been found that the biolayer of the present invention may continue to produce products after the nutrient solution has been replaced by a second liquid that does not contain nutrient, for example a solution of saline and/or buffer. Consequently one method for operating a bioreactor according to the invention is to supply nutrient solution to the nutrient face of the membrane for a first period, and then supply a second liquid that does not contain nutrient to the membrane for a second period. The virtually cell-free and nutrient-free solution thus provides for still easier processing to separate products. In the latter method, the first period may depend on the nature of the biolayer and on the conditions of operating the bioseparator. The first period may be between about 1 hour and 1 day, or between about 1 and 18 hours or between about 1 and 12 hours or between about 1 and 6 hours or between about 1 and 3 hours or between about 1 and 2 hours or between about 6 hours and 1 day or between about 12 hours and 1 day or between about 18 hours and 1 day or between about 3 and 18 hours or between about 6 and 12 hours, and may be about 1, 2, 3, 4, 5, 6, 12, 18 or 24 hours. The second period may also depend on the nature of the biolayer and on the conditions of operating the bioreactor, and may depend on the length of the first period. The second period may be between about 12 hours and 12 days or between about 12 hours and 8 days or between about 12 hours and 4 days or between about 12 hours and 2 days or between about 12 hours and 1 day, or between about 1 and 12 days or between about 4 and 12 days or between about 8 and 12 days or between about 1 and 6 days or between about 2 and 4 days, and may be about 12 or 18 hours or about 1, 2, 3, 4, 5, 6, 7, 8, 9, 10, 11 or 12 days.

In order to promote the health and efficient operation of the biolayer, the biolayer may be kept at a particular temperature. The temperature will depend on the nature of the biolayer, as different biological materials perform optimally at different temperatures. The temperature may vary slightly during operation of the bioreactor. The temperature may be between about −5 and 120° C., or between −5 and 0° C. or between about 0 and 100° C. or between about 0 and 50° C. or between about 0 and 20° C. or between about 20 and 120° C. or between about 50 and 120° C. or between about 90 and 120° C. or between about 10 and 45° C. or between about 10 and 35° C. or between about 10 and 25° C., or between about 20 and 55° C. or between about 30 and 55° C. or between about 40 and 55° C. or between about 15 and 45° C. or between about 17 and 42° C. or between about 20 and 40° C. or between about 20 and 30° C. or between about 30 and 40° C., and may be about −5, 0, 5, 10, 15, 17, 20, 25, 28, 30, 35, 37, 40, 42, 45, 50, 60, 70, 80, 90, 100, 110 or 120° C. The temperature may be kept at about the desired temperature by the air or the effluent liquid which is in contact with the biolayer.

The bioreactor may be operated for the purpose of producing soluble products, which are recoverable from a liquid at the nutrient face of the membrane, for example pharmaceuticals, antibodies, vaccine components, or other chemicals, and/or solid products which are recoverable from the gas face of the membrane, for example food material or cells or it may be for the purpose of removing undesirable components from the nutrient liquid. Additionally or alternatively the bioreactor may be used to remove undesirable components (e.g. C, N, S, P, Mn, Mg, Ca, Zn, heavy metals), such as pollutants, of a nutrients stream, either by bioconversion (for example metabolism of carbohydrate in order to reduce Biological Oxygen Demand (BOD), bioreduction or bio-oxidation of metal ions to reduce pollutant loading, removal of sulfur, phosphorus or nitrogen compounds) or by biosorption of components such as metal ions onto the biolayer. This may be applied in the treatment of wastewaters, biosorption of metal ions from a liquid stream, and for recovery applications for mining and bioremediation applications.

The membrane-supporting structure may be any suitable structure for supporting the membrane, or, in the case of a bioreactor having more than one membrane, all of the membranes, of the invention. It may be for example a frame, a bracket, a casing, a housing, a rack or a scaffold. It may be made of metal, for example aluminium, steel, stainless steel, titanium or other suitable metal, or it may be made of a suitably rigid plastic, for example polyethylene, polypropylene, polymethylpentene, polymethyl methacrylate or polycarbonate. The membrane-supporting structure may support the membrane(s) in a vertical position or in a horizontal position. The membrane supporting structure may comprise rollers and motors for assisting movement of the membrane within the bioreactor.

The membrane of the invention may be nanoporous, mesoporous or microporous or it may have a combination of nanoscale and/or mesoscale and/or microscale pores. It may be capable of allowing the cells or spores of the biolayer to pass therethrough or it may be incapable of allowing the cells or spores of the biolayer to pass therethrough. The membrane comprises a support material, as described below, and may also have a nanoporous solid or gel, as described below, on and/or in the support material, although a membrane according to the invention may have no nanoporous solid or gel. The membrane may comprise between about 0 and 90% nanoporous gel on a weight or a volume basis, or between 10 and 90% or between about 10 and 50% or between about 10 and 30% or between about 30 and 90% or between about 50 and 90% or between about 70 and 90% or between about 20 and 80% or between about 30 and 70% or between about 40 and 60% nanoporous gel on a weight or a volume basis, or may comprise about 0, 10, 20, 30, 40, 50, 60, 70, 80 or 90% nanoporous gel on a weight or a volume basis. The membrane may be planar or it may be tubular. The thickness of the membrane may be between about 0.1 and 10 mm thick, and may be between about 0.1 and 5 mm thick or between about 0.1 and 2 mm thick or between about 0.1 and 1 mm thick or between about 1 and 10 mm thick or between about 5 and 1.0 mm thick or between about 0.5 and 5 mm thick or between about 1 and 5 mm thick or between about 1 and 2 mm thick, and may be about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9 or 10 mm thick. When the membrane is fabricated, the distribution of cells within the nanoporous material may initially be approximately homogeneous. However in operation, the conditions of operation may encourage growth of the cells near and/or on the gas face, and may discourage growth of cells in other regions of the membrane. This may lead to a membrane in operation that has a non-homogeneous distribution of cells, with a higher concentration of cells near and/or on the gas face.

The nanoporous solid or gel may comprise any suitable material that can be fabricated from a precursor liquid, wherein the precursor liquid is suitable for dispersing cells therein without damage to the cells. The nanoporous solid or gel may comprise for example silica gel, titania gel, zirconia gel, alumina gel or a mixed gel comprising two or more of silica, titania, zirconia and alumina (e.g. silica-alumina gel), or it may comprise agar agar, agarose, calcium alginate, pectin or other biopolymer. Furthermore, a nanoporous inorganic gel composed of ferrihydrite may develop on/in the membranes as a result of the actions of *Acidithiobacillus ferrooxidans*.

The porosity of the nanoporous solid or gel may be between about 40 and 90%, or between about 40 and 75% or between about 40 and 60% or between about 50 and 90% or between about 60 and 90% or between about 70 and 90% or between about 50 and 80% or between about 60 and 70%, and may be about 40, 45, 50, 55, 60, 65, 70, 75, 80, 85 or 90%. The pores may have a mean diameter between about 1 nm and 10 microns, or between about 1 nm and 1 micron or between about 1 and 500 nm or between about 1 and 100 nm or between about 1 and 50 nm or between about 1 and 10 nm or between about 100 nm and 10 microns or between about 500 nm and 10 microns or between about 1 and 10 microns or between about 10 nm and 1 micron or between about 50 and 500 nm or between about 100 and 200 nm, and may have a mean diameter about 1, 5, 10, 15, 20, 25, 30, 35, 40, 45, 50, 75, 100, 150, 200, 250, 300, 350, 400, 450, 500, 600, 700, 800 or 900 nm or about 1, 2, 3, 4, 5, 6, 7, 8, 9 or 10 microns. The nanoporous solid or gel may have liquid in the pores thereof, and the liquid may be an aqueous liquid. The aqueous liquid may contain nutrients for the biological entities, and it may contain products produced by the biological entities, and it may contain other components for example electrolytes, salts, vitamins, growth factors and/or dissolved gases.

The biolayer may be for example a biofilm. The biolayer may comprise cells, spores or other biological entities or a combination thereof. The biolayer may be capable of producing a desired product such as an antibiotic, a pharmaceutical, an antibody, a vaccine, a chemical, a food material, cells or a hormone, for example it may comprise *Penicillium chrysogenum* which are capable of producing penicillin. Alternatively it may comprise cells capable of sorbing metals (which may be in the form of metal ions) such as lead, or of removing other waste materials or for decontamination of an effluent, for example they may be *Aspergillus niger*, which is capable of removing carbohydrate material. The biolayer may be located on and/or in the membrane, and may be located on and/or in the gas face of the membrane so that the biolayer may be exposed to the gas in the bioreactor. The bioreactor thus may be capable of producing a desirable product, or of removing materials, for example pollutants or unwanted materials, from either a liquid stream which is presented to the nutrient face of the membrane as a nutrient stream or from a gas stream which is presented to biolayer on the gas face of the membrane. For example, microorganisms may mediate the removal of contaminants (e.g. ozone, $H_2S$, $SO_2$ etc.) from a gas stream. In this case the gas face of the membrane may be disposed with in a gas chamber or housing, and the gas stream may be recirculated through the gas chamber past the biolayer, and may be recirculated for sufficient time for the concentration of the contaminant to reduce to an acceptable level.

The support material may be made of a material that is non-biodegradable under the conditions of operation of the membrane. The support material may be hydrophilic or hydrophobic, and may comprise a porous material or a woven material or a non-woven fibrous material or a sponge-like material or an open cell foam material or some other material having holes connecting a first face of the support and a second face of the support. The support material may be, for example a woven or non-woven fibrous material or a non-fibrous porous material. The fibrous material may be glass fibre matting or cotton, and the non-fibrous porous material may be macroporous, for example an open-celled foam, or it may be mesoporous and/or microporous. It may be rigid or it may be flexible. The porosity of the support may be between about 40 and 90%, or between about 40 and 75% or between about 40 and 60% or between about 50 and 90% or between about 60 and 90% or between about 70 and 90%, or between about 50 and 80% or between about 60 and 70%, and may be about 40, 45, 50, 55, 60, 65, 70, 75, 80, 85 or 90%. The holes of the support may be between about 10 and 200 microns or between about 10 and 100 microns or between about 10 and 50 microns or between about 50 and 200 microns or between about 100 and 200 microns or between about 50 and 150 microns, and may be about 10, 20, 30, 40, 50, 60, 70, 80, 90, 100, 150 or 200 microns. The woven or non-woven material may have between about 10 and 100 strands/cm or between about 20 and about 100 strands/cm, or between about 40 and 100 strands/cm or between about 60 and 100 strands/cm, or between about 10 and 60 strands/cm or between about 10 and 40 strands/cm or between about 25 and 70 strands/cm or between about 30 and 60 strands/cm or between about 35 and 50 strands/cm or between about 35 and 45 strands/cm, and may have about 10, 15, 20, 25, 30, 35, 40, 45, 50, 55, 60, 65, 70, 75, 80, 85, 90, 95 or 100 strands/cm. The thickness of the strands may be between about 20 and 1000 microns or between about 20 and 500 microns or between about 20 and 200 microns or between about 20 and 100 microns or between about 100 and 500 microns or between about 200 and 500 microns or between about 300 and 500 microns, or between about 50 and 400 microns or between about 100 and 300 microns or between about 500 and 1000 microns or between about 750 and 1000 microns or between about 500 and 750 microns, and may be about 20, 30, 40, 50, 100, 150, 200, 250, 300, 350, 400, 450, 500, 600, 700, 800, 900 or 1000 microns. The support may comprise for example a glass fibre matting, woven glass matting, polyester, microporous polyolefin (for example polyethylene or polypropylene), microporous fluoropolymer (such as polyvinylidene fluoride or polytetrafluoroethylene), cotton, polyester-cotton, silk, wool, sintered glass, sintered metal or some other porous or fibrous material.

The support material may be a hydrophilic material. Before use, the support material may be treated in order to clean the surface and/or to render the surface more hydrophilic. The details of the treatment may depend on the nature of the material. For example a treatment that may be used comprises the step of exposing the support material to an alkaline solution, for example aqueous potassium hydroxide solution. The alkaline solution may be between about 0.1 and 5M, or between about 0.1 and 1M or between about 0.1 and 0.5M or between about 0.5 and 5M or between about 1 and 5M or between about 3 and 5M or between about 0.5 and 2M, and may be about 0.1, 0.2, 0.3, 0.4, 0.5, 0.6, 0.7, 0.8, 0.9, 1, 1, 5, 2, 2.5, 3, 3.5, 4, 4.5 or 5M. When treating a support material that comprises woven glass matting (or other glass fibre), the step of exposing may be for between about 12 and 48 hours, or between about 18 and 36 hours, or between about 20 and 28 hours, or between about 12 and 24 hours or between about 12 and 18 hours or between about 24 and 48 hours or between about 36 and 48 hours, and may be for about 12, 18, 24, 30, 36, 42 or 48 hours. However when treating a support material that comprises cotton, polyester-cotton or polyester, the step of exposing should be much shorter so as not to damage the support material, and may be between about 1 and 20 minutes, or between about 1 and 10 minutes or between about 1 and 5 minutes or between about 10 and 20 minutes or between about 15 and 20 minutes or between about 2 and 15 minutes or between about 3 and 10 minutes or between about 4 and 7 minutes, and may be about 1, 2, 3, 4, 5, 6, 7, 8, 9, 10, 12, 14, 16, 18 or 20 minutes. An alternate treatment that may be used is to expose the support material to a water plasma (which may be for example formed within an RF generator). The exposure may be for between about 1 and 20 minutes, or between about 1 and 10 minutes or between about 1 and 5 minutes or between about 10 and 20 minutes or between about 15 and 20 minutes or between about 2 and 15 minutes or between about 3 and 10 minutes or between about 5 and 8 minutes, and may be for about 1, 2, 3, 4, 5, 6, 7, 8, 9, 10, 12, 14, 16, 18 or 20 minutes. In an example, the support may be etched for about 6 minutes in water plasma at about $5.0 \times 10^{-2}$ millibar in a 40 W radio frequency plasma generator operating at 13.56 mH RM to hydroxylate the surfaces making them wettable. Alternatively an oven may be used to burn hydrophobic materials off glass support materials to make them more hydrophilic. The temperature of the oven may be between about 300 and 700° C., or between about 300 and 500° C. or between about 300 and 400° C. or between about 500 and 700° C. or between about 500 and 700° C. or between about 400 and 600° C., and may be about 400, 450, 500, 550, 600, 650 or 700° C. The time required to burn hydrophobic materials off a glass support material may be between about 5 minutes and 36 hours, or between about 10 minutes and about 24 hours or between about 30 minutes and 18 hours or between about 1 and 12 hours or between about 2 and 6 hours or between about 5 minutes and 12 hours or between about 5 minutes and 6 hours or between about 5 minutes and 1 hour or between about 5 and 30 minutes or between about 10 and 30 minutes or between about 1 and 36 hours or between about 6 and 24 hours or between about 12 and 24 hours or between about 18 and 24 hours, and may be about 5, 10, 15, 20, 25, 30, 40 or 50 minutes or about 1, 2, 3, 4, 5, 6, 9, 12, 18, 24, 30 or 36 hours.

The precursor liquid may be any liquid which is suitable for dispersing cells therein without damage to the cells, and which can be converted to a nanoporous material without damage to either the cells or the support. An example of a precursor liquid is alkaline colloidal silica solution. These solutions are commonly at a pH of around 10, however may have a pH between about 9 and 11 or between about 9.5 and 10.5 or between about 9 and 10 or between about 10 and 11, and may have a pH of about 9, 9.5, 10, 10.5 or 11. The solids concentration of silica in the colloidal silica solution may be about 30% on a weight/weight basis, or between about 15 and 50% or between about 20 and 45% or between about 25 and 40% or between about 30 and 35% or between about 15 and 40% or between about 15 and 30% or between about 25 and 50% or between about 35 and 50% on a weigh/weight basis, or may be about 15, 20, 25, 30, 35, 40, 45 or 50% on a weight/weight basis, or it may be about 17% on a volume/volume basis, or between about 10 and 20% or between about 12 and 20% or between about 15 and 20% or between about 16 and 20% or between about 10 and 18% or between about 10 and 16% or between about 10 and 14% or between about 12 and 19% or between about 14 and 18% or between about 16 and 17% on a volume/volume basis, or it may be about 10, 11, 12, 13, 14, 15, 16, 17, 18, 19 or 20% on a volume/volume basis.

The cells to be immobilised in the nanoporous solid or gel may be dispersed in the precursor liquid. The concentration of cells in the precursor liquid may be between about $10^1$ and $10^{12}$ cfu/ml or between about $10^1$ and $10^5$ cfu/ml or between about $10^1$ and $10^3$ cfu/ml or between about $10^9$ and $10^{12}$ cfu/ml or between about $10^{10}$ and $10^{12}$ cfu/ml or between about $10^5$ and $10^9$ cfu/ml or between about $10^6$ and $10^8$ cfu/ml or between about $5*10^6$ and $5*10^7$ cfu/ml or between about $10^7$ and $10^9$ cfu/ml or between about $5*10^7$ and $5*10^8$ cfu/ml or between about $10^5$ and $10^7$ cfu/ml or between about $5*10^5$ and $5*10^6$ cfu/ml, or may be about $10^1$, $10^2$, $10^3$, $10^4$, $10^5$, $5*10^5$, $10^6$, $5*10^6$, $10^7$, $5*10^7$, $10^8$, $5*10^8$, $10^9$, $10^{10}$, $10^{11}$ or $10^{12}$ cfu/ml.

The nanoporous solid or gel may comprise for example silica gel, titania gel, zirconia gel, alumina gel, or a mixed gel comprising two or more of silica, titania, zirconia and alumina (e.g. silica-alumina gel), or it may comprise agar agar, agarose, calcium alginate, pectin or other biopolymer. The mixed gels may be made by a process which comprises, as one step, controlled hydrolysis of mixtures of the corresponding alkoxides, for example silica-titania gel may be made by controlled hydrolysis of a tetraalkoxysilane (e.g. tetramethoxysilane $Si(OMe)_4$ TMOS) with a tetralkyltitanate (e.g. tetramethyltitanate $Ti(OMe)_4$). Alternatively the gel may be made using a trialkoxysilane, for example methyl trimethoxysilane or a functional alkylalkoxysilane (e.g. methacryloyloxypropytrimethoxysilane). The precursor liquid may be converted in to the nanoporous solid or gel by changing the pH (for example acidifying), or by evaporating a volatile liquid from the precursor liquid. The evaporating may comprise heating and/or passing a gas past the support material having the precursor liquid. The heating may be to a temperature sufficient to evaporate the volatile liquid but insufficient to cause deterioration of the support material or of the cells and/or spores therein if present. The temperature may be between about 30 and 90° C., or between about 30 and 80, 30 and 60, 30 and 40, 50 and 80 or 40 and 60° C., and may be about 30, 40, 50, 60, 70, 80 or 90° C., or it may be greater than 90° C. if the support material and any cells and/or spores therein are capable of withstanding that temperature. A sufficient amount of volatile liquid may be evaporated to cause the formation of the nanoporous solid or gel on and/or in the support material.

Thus a sol (e.g. a hydrosol), which is the precursor liquid, is infused into the support material, and caused to gel in the support material, by a suitable sol-gel process which may depend on the nature of the sol, and may comprise one or more of: pH adjustment, temperature adjustment, evaporation of volatile liquid, exposure to a reagent and precipitation with a metal ion.

In one example of a fabrication process, a support material having a plurality of holes therein, is exposed to a colloidal silica solution having the cells dispersed therein, and the pH of the colloidal silica solution in the holes is reduced in order to form a nanoporous silica gel having the cells immobilised therein in the holes of the support material. The pH may be reduced to between about 4 and about 8, or between about 5 and about 7 or between about 4 and about 7 or between about 4 and about 6, or between about 5 and about 8 or between about 6 and about 8 and may be reduced to about 4, 4.5, 5, 5.5, 6, 6.5, 7, 7.5 or 8. The step of reducing the pH may comprise the steps of removing the support having the precursor solutions in the holes thereof from the bulk precursor solution and immersing the support in an aqueous solution of the desired pH. Alternatively a colloidal silica solution is adjusted to pH between about 4 and about 8 as described above. Cells are then added to the colloidal silica solution, and, before gelation, the solution is infused into the support material. This alternative process is particularly useful for use with cells that are sensitive to high pH environments.

Other examples of precursor liquids include aqueous solutions of sodium alginate or of agar agar or agarose. The concentration of solute in the precursor liquid should be such that the viscosity of the precursor liquid is suitable for infusing into the support. The concentration will depend on factors which include the molecular weight and nature of the solute and the nature (pore size or mesh size) of the support material. The concentration may be between about 0.5% and 40% by weight or by volume and may be between about 0.5 and 30%, about 0.5 and 20%, about 0.5 and 15%, about 0.5 and 10%, about 0.5 and 5%, about 1% and 10%, about 1% and 5%, about 5 and 40%, about 10 and 40%, about 15 and 40%, about 20 and 40%, about 30 and 40%, about 5 and 30% or about 10 and 20%, and may be about 0.5, 0.6, 0.7, 0.8, 0.9, 1, 2, 3, 4, 5, 10, 15, 20, 25, 30, 35 or 40% by weight or by volume. Evaporation of a part of the water of the aqueous solution may cause the solute to precipitate as a gel on and/or in the support material. In the case that the nanoporous solid or gel comprises agar agar, the precursor solution may be made by heating agar agar with an aqueous liquid to a temperature above the gel temperature of the agar agar in order to dissolve it. The gel temperature depends on the grade of agar agar and may be between about 25 and about 70° C. Preferably the grade of agar agar is selected so that its gel temperature is sufficiently low that the cells are not harmed at the temperature at which the dissolution is effected. The gel temperature may conveniently be below about 50° C., and may be below about 45° C. or below about 40° C., and may be about 30, 35, 40, 45 or 50° C. The concentration of agar agar in the precursor liquid may be between about 0.5 and 5% by weight or by volume, or between about 0.5 and 4% or between about 0.5 and 3% or between about 0.5 and 2% or between about 1 and 3%, or may be about 0.5, 0.6, 0.7, 0.8, 0.9, 1, 2, 3, 4 or 5% by weight or by volume. Cooling the support material infused with the precursor solution causes precipitation of an agar agar gel in and/or on the support material. If the gel temperature of the agar agar is sufficiently high as to cause damage to the cells, agar agar gel may be formed in the support material as described earlier, but without the cells in the precursor solution, and the resulting membrane may be inoculated with cells after formation of the membrane. In the case that the nanoporous solid or gel comprises calcium alginate, the precursor solution may be an aqueous solution of alginic acid, or of a soluble alginate salt such as sodium alginate. The concentration of alginic acid may be between about 1 and 10% by weight or by volume or between about 1 and 5% or between about 1 and 3% or between about 5 and 10% or between about 7 and 10% or between about 2 and 7% or between about 3 and 5% and may be about 1, 2, 3, 4, 5, 6, 7, 8, 9 or 10% by weight or by volume. Thus immersion of a support infused with the precursor solution into a solution of a metal ion the alginate salt of which is insoluble in water (for example calcium) causes precipitation of an insoluble alginate salt, for example calcium alginate, in and/or on the support material. The alginate salt may be for example calcium alginate, and the solution thereof may be between about 1 and 5% by weight or by volume, or between about 1 and 4% or between 1 and 3% or may be about 1, 2, 3, 4 or 5% by weight or by volume.

With reference to FIG. 1, membrane 10 has nutrient face 12 and gas face 14, and comprises fibrous support material 16 having nanoporous gel 18 therein and thereon. Immobilised biolayer 20 is located on gas face 14 and in membrane 10 near gas face 14. Fibrous support material 16 comprises a woven glass fibre mesh which does not have sizing agent, and nanoporous gel 18 comprises a nanoporous silica gel. Biolayer 20 comprises fungi 22 which are embedded in membrane 20 near gas face 14, and fungi 24 on or near gas face 14. Fungi 22 and 24 may be for example *Penicillium chrysogenum*, which are capable of producing penicillin.

In operation, membrane 10 allows diffusion of nutrient solution 26 from nutrient face 12 to immobilised biolayer 20 in the direction of arrow 21. Air is provided to surface 28 of biolayer 20, promoting growth of fungi 22 and 24, and consequent production of products (for example penicillin) by biolayer 20. Growth of fungi in nutrient solution 26 and inside membrane 10 is discouraged, due to the relatively anoxic conditions in those regions. Products diffuse from biolayer 20 through membrane 10 in the direction of arrow 23.

Figure 2:
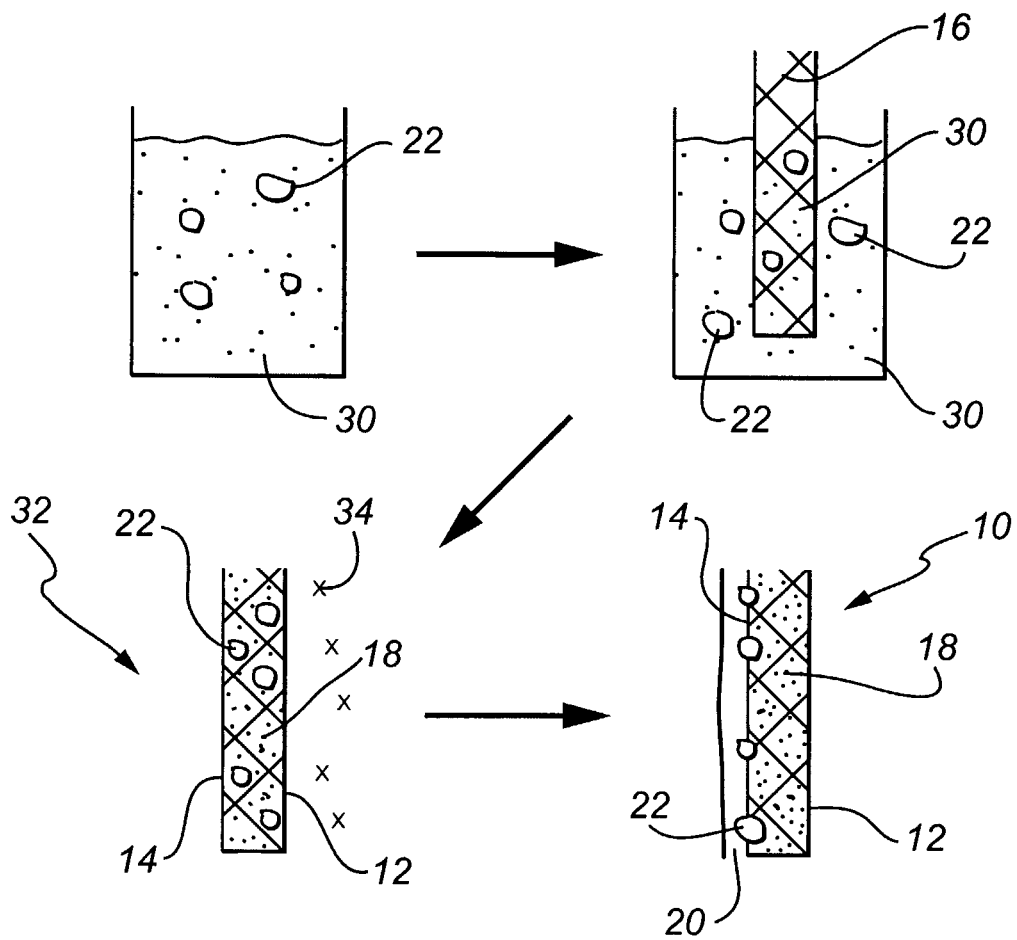
FIG. 2 shows a scheme describing a process for fabricating a membrane having a biolayer thereon and/or therein according to the invention.

FIG. 2 shows a scheme describing a process for fabricating a membrane having a biolayer thereon and/or therein. With reference to FIG. 2, support material 16 is a fibrous mesh, for example glass fibre woven matting. Before use, support material 16 may be treated in order to clean the surface of sizing agents and other contaminants and to render its surface more hydrophilic. A treatment that may be used comprises exposing support material 16 to an alkaline solution, for example an approximately 1M aqueous potassium hydroxide solution for about 24 hours. The process of making the membrane comprises adjusting a colloidal silica solution, which is initially at pH around 10 with solids content of about 30% w/w, to a pH of about 6, for example by adding a mineral acid solution, such as sulfuric acid or hydrochloric acid, which may be between about 1 and 5N, or between about 1 and 3N or between about 3 and 5N or between about 2 and 5N, and may be about 1, 2, 3, 4 or 5N. Fungi 22, for example *P. chrysogenum*, are added to provide an overall count of about $10^9$ cfu/ml, to produce precursor liquid 30. Precursor liquid 30 is infused into support material 16 by immersing support material 16 in precursor liquid 30. Precursor liquid 30 will gel shortly after being adjusted to pH about 6, commonly within about 30 minutes, and therefore it is necessary to remove support material 16 from precursor liquid 30 before gelation. On removal of support material 16 from precursor liquid 30, precursor liquid 30 remains infused therein. On standing under ambient conditions, precursor liquid 30 gels in support material 16 to form membrane 32 which has fungi 22 distributed approximately evenly throughout and which has nanoporous gel 18 therein. Providing nutrient solution 34 to nutrient face 12 of membrane 32 allows nutrient solution 34 to penetrate membrane 32. Exposure of gas face 14 to air does not permit air to penetrate membrane 32 to a substantial degree since the pores thereof are filled with liquid. This encourages growth of fungi 22 at or near gas face 14, and discourages growth in other less oxygenated regions of membrane 32. Thus membrane 32, which initially has a symmetrical distribution of fungi 22, develops an asymmetric distribution, resulting in membrane 10 having biolayer 20 (comprising fungi 22) on and in gas face 14.

Figure 2A:
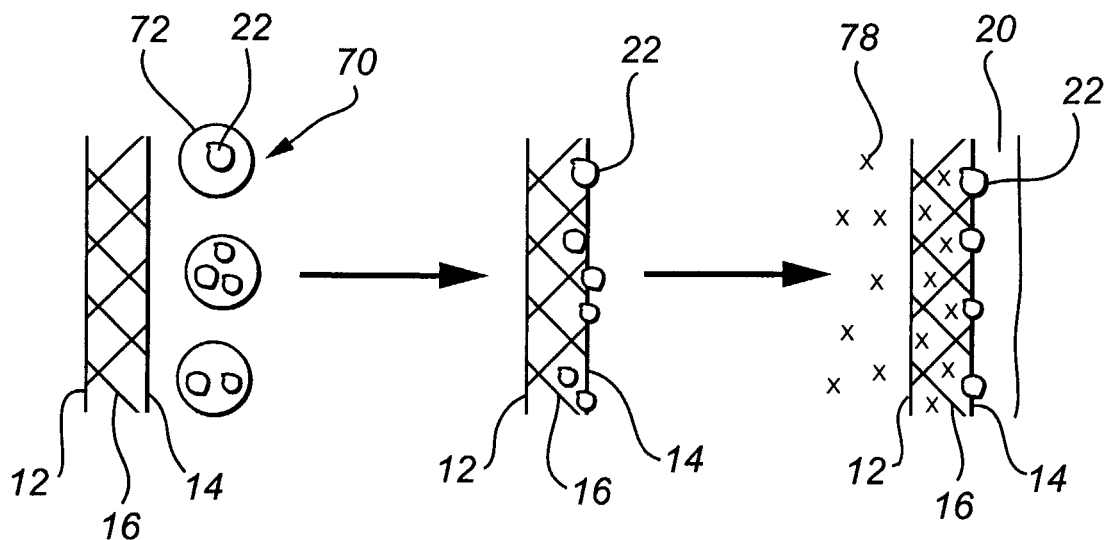
FIG. 2a shows another scheme describing a different process for fabricating a membrane having an immobilised biolayer thereon and/or therein according to the invention.

FIG. 2a shows another scheme describing a different process for fabricating a membrane having an immobilised biolayer. In FIG. 2a, the membrane comprises support 16. Support material 16 is a fibrous mesh, for example cotton, and spray 70 comprises droplets 72 having fungi 22 therein. Exposure of gas face 14 of support material 16 to spray 70 causes fungi 22 to deposit onto gas face 14, and some of fungi 22 may also penetrate into support 16. Exposure of nutrient face 12 of the membrane to nutrient solution 78 allows solution 78 to diffuse through support material 16 to fungi 22, displacing the air in support material 16. This encourages growth of fungi 22 at or near gas face 14, and discourages growth in other less oxygenated regions of the membrane. This leads to formation of biolayer 20, located on, and partially in, gas face 14.

With reference to FIG. 3, bioreactor 50 comprises membrane-supporting structure 52 and membranes 10 supported vertically by structure 52. Each of membranes 10 is planar and is oriented parallel to the other membranes 10. Membranes 10 are arranged in pairs so that each pair is joined so as to form a flattened tube, a cross-section of which is shown.

Each membrane 10 has a biolayer 20 immobilised thereon, such that a nutrient solution is capable of diffusing thereto. Biolayer 20 may comprise fungi, for example *P. chrysogenum*, which is capable of producing penicillin. Bioreactor 50 has spacers 54 for maintaining a distance between the membranes of each pair. Each membrane 10 has a scraper 56 for removal of excess biomass from biolayer 20. Bioreactor 50 has inlets 58 for admitting the nutrient solution to the nutrient face of membranes 10, and also has outlets 60 for removing the nutrient solution from between the membranes of each pair. Inlets 58 are connected to inlet manifold 62 and outlets 60 are connected to outlet manifold 64.

In operation, nutrient solution is supplied through inlet manifold 62 and inlets 58. The nutrient solution is a suitable nutrient solution for the fungi of biolayers 20, and may for example contain carbohydrates. Bioreactor 50 is located in an aerobic environment, thereby exposing biolayer 20 to air. The nutrient solution is allowed to diffuse through membranes 10 to biolayers 20. Biolayers 20 are thus provided with the conditions required for producing the desired product, in the above example penicillin. This product diffuses through membrane 10, and exits bioreactor 50 in the nutrient solution through outlets 60 and outlet manifold 64. The exiting nutrient solution may be collected for separation of the desired product. In the event that biolayers 20 becomes sufficiently thick that production of product is retarded due to lack of oxygen to portions thereof, scrapers 56 can be passed down biolayers 20 in order to remove solid matter therefrom. In an alternative mode of operation, nutrient solution is provided to membranes 10 as described above for a first period of time, which may be between about 12 and 24 hours. Following this first period, a saline solution is provided to membranes 10 for a second period of time through inlet manifold 62 and inlets 58, and thereby displaces the nutrient solution in bioreactor 50. The second period may be between about 1 and 5 days. During the second period, biolayer 20 produces the desired product as described above. This product diffuses through membranes 10, and exits bioreactor 50 in the saline solution through outlets 60 and outlet manifold 64. Separation of the desired product from the exiting saline solution may be easily accomplished.

Figure 3:
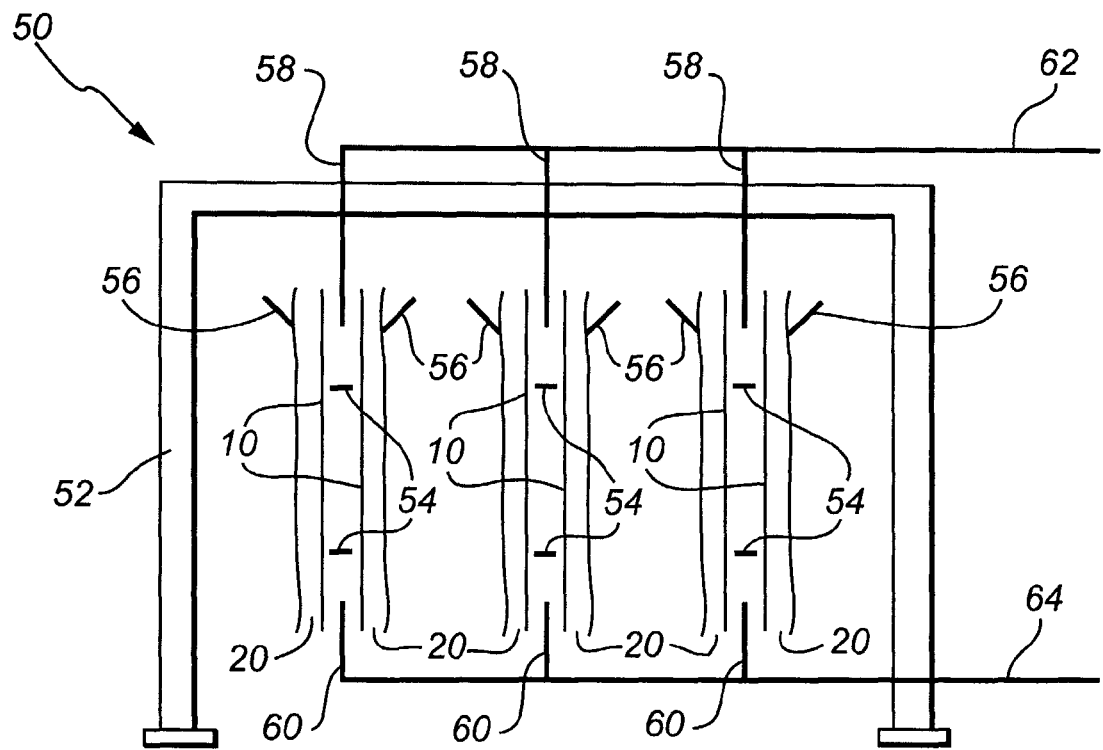
FIG. 3 is a diagrammatic representation of a bioreactor according to the invention.
Figure 3A:
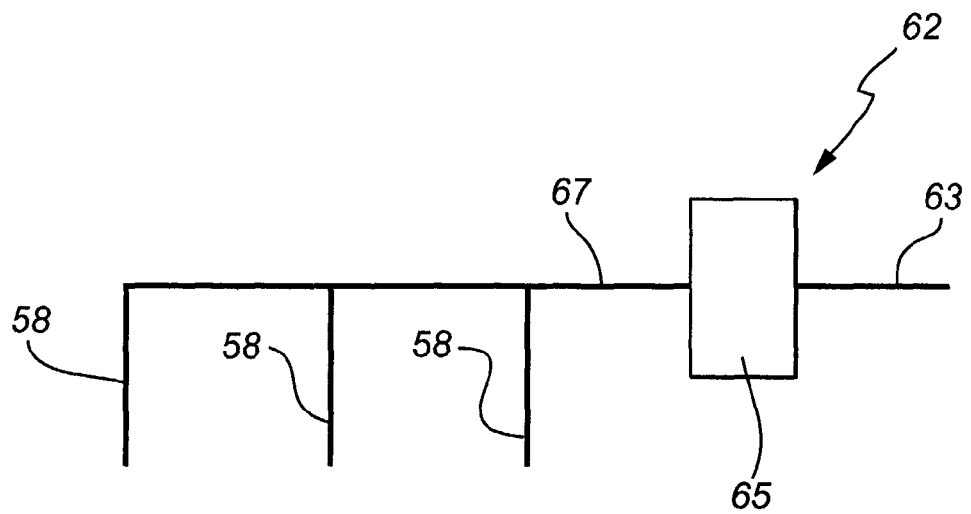
FIG. 3a is a diagrammatic representation of an inlet manifold that may be used in the bioreactor shown in FIG. 3.

FIG. 3a shows an inlet manifold that may be used in the bioreactor shown in FIG. 3. In FIG. 3a, manifold inlet 63 leads to oxygen remover 65. Oxygen remover may be any convenient oxygen remover, and may comprise for example a degasser, such as a vacuum degasser, or it may comprise a sparge device for bubbling a gas having very little oxygen, for example nitrogen or carbon dioxide, through the nutrient solution. Manifold pipe 67 connects oxygen remover 65 to inlets 58. In operation, nutrient solution is provided through manifold inlet 63 to oxygen remover 65, which removes oxygen to a low level, for example below about 5 ppm. The relatively anoxic nutrient solution then passes through manifold pipe 67 to inlets 58 which supply the nutrient solution to the membranes of the bioreactor (not shown).

Figure 3B:
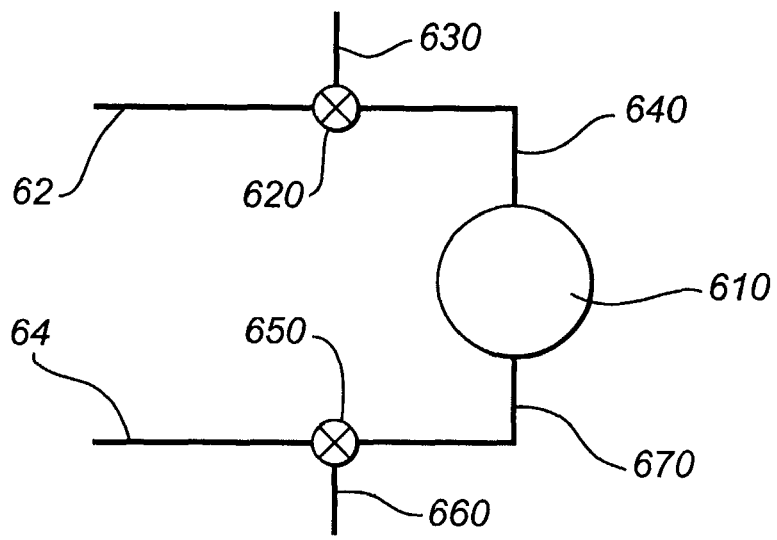
FIG. 3b is a diagrammatic representation of a recycling system for recycling a liquid from the outlet to the inlet of a bioreactor according to the invention.

FIG. 3b shows a recycling system for recycling a liquid from the outlet to the inlet of a bioreactor according to the invention. In FIG. 3b, feed line valve 620 is a three-way valve connected to inlet manifold 62 of bioreactor 50 (shown in FIG. 3 but not in FIG. 3b), feed line 630 and pump outlet pipe 640. Exit line valve 650 is a three-way valve connected to outlet manifold 64 of bioreactor 50 (of FIG. 3), exit line 660 and pump inlet pipe 670. In normal operation of bioreactor 50, feed line valve 620 is configured so that liquid can pass from pipe 640 to manifold 62, but line 630 is closed, and exit line valve 650 is configured so that liquid can pass from manifold 64 to pipe 670, but line 660 is closed. In this configuration, pump 610 pumps fluid from exit manifold 64 to inlet manifold 62 via pipes 670 and 640, and no liquid passes through lines 630 or 660. In order to add liquid to bioreactor 50, for example at the commencement of operation of the bioreactor, valve 620 is configured so that liquid can pass from line 630 to inlet manifold but not to pipe 640. Similarly, in order to remove liquid from bioreactor 50, for example in order to pass the liquid to a separator for separating products from it, valve 650 is configured so that liquid can pass from outlet manifold to exit line 660 but not to pipe 670.

Figure 3C:
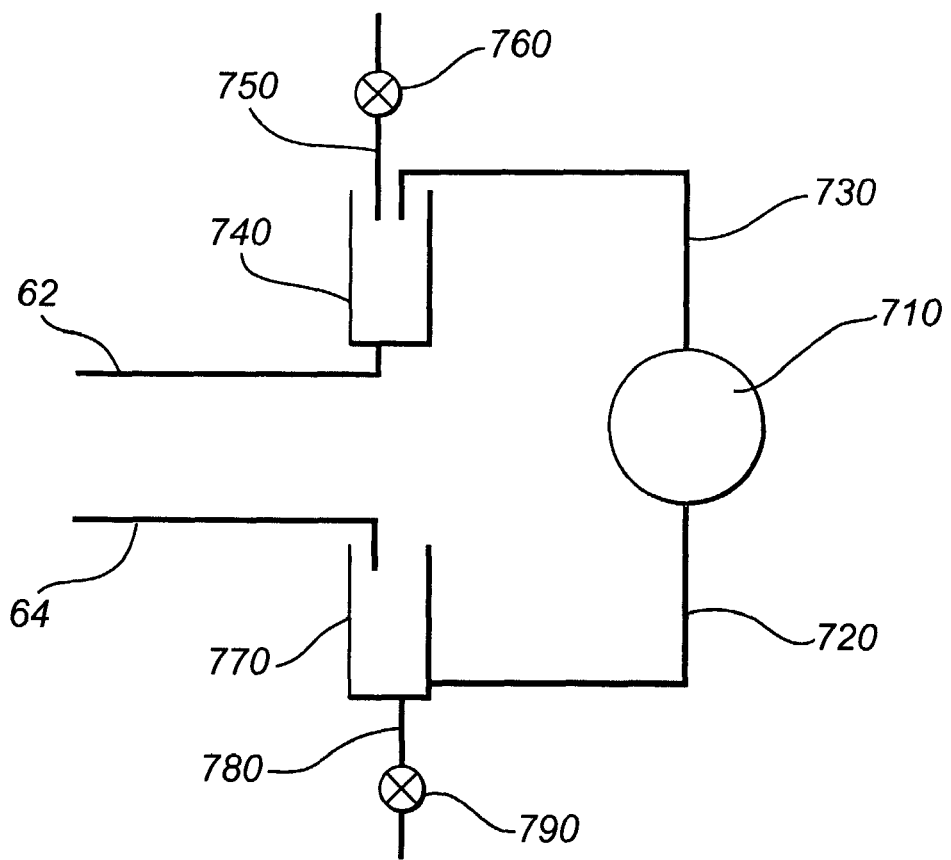
FIG. 3c is a diagrammatic representation of another recycling system for recycling a liquid from the outlet to the inlet of a bioreactor according to the invention.

FIG. 3c shows another recycling system for recycling a liquid from the outlet to the inlet of a bioreactor according to the invention. In FIG. 3c, pump 710 has pump inlet pipe 720 and pump outlet pipe 730. Pump outlet pipe 730 outputs into feed tank 740. Feed line 750, fitted with valve 760 also outputs into tank 740. Tank 740 is connected to inlet manifold 62 of bioreactor 50 (shown in FIG. 3 but not in FIG. 3c). Outlet manifold 64 of bioreactor 50 outputs into exit tank 770, which is connected to pump inlet pipe 720 and to exit line 780, fitted with exit line valve 790. Tanks 740 and 770 may optionally have means to exclude oxygen from liquid therein. Such means may comprise for example an inert gas sparge, a lid, a movable plunger or other suitable means. In normal operation of bioreactor 50, feed line valve 760 is closed in order to prevent liquid entering tank 740 through line 750, and exit line valve 790 is closed in order to prevent liquid exiting tank 770 through exit line 780. In this configuration, liquid flows from tank 740 to inlet manifold 62, and is returned via exit manifold 64 to tank 770. Pump 710 pumps the liquid from tank 770 through pipes 720 and 730 to tank 740. In order to add liquid to bioreactor 50, for example at the commencement of operation of the bioreactor, valve 760 is opened so that liquid can pass from line 750 to tank 740. Similarly, in order to remove liquid from bioreactor 50, for example in order to pass the liquid to a separator for separating products from it, valve 790 is opened so that liquid can pass from tank 770 to exit line 780.

Figure 3D:
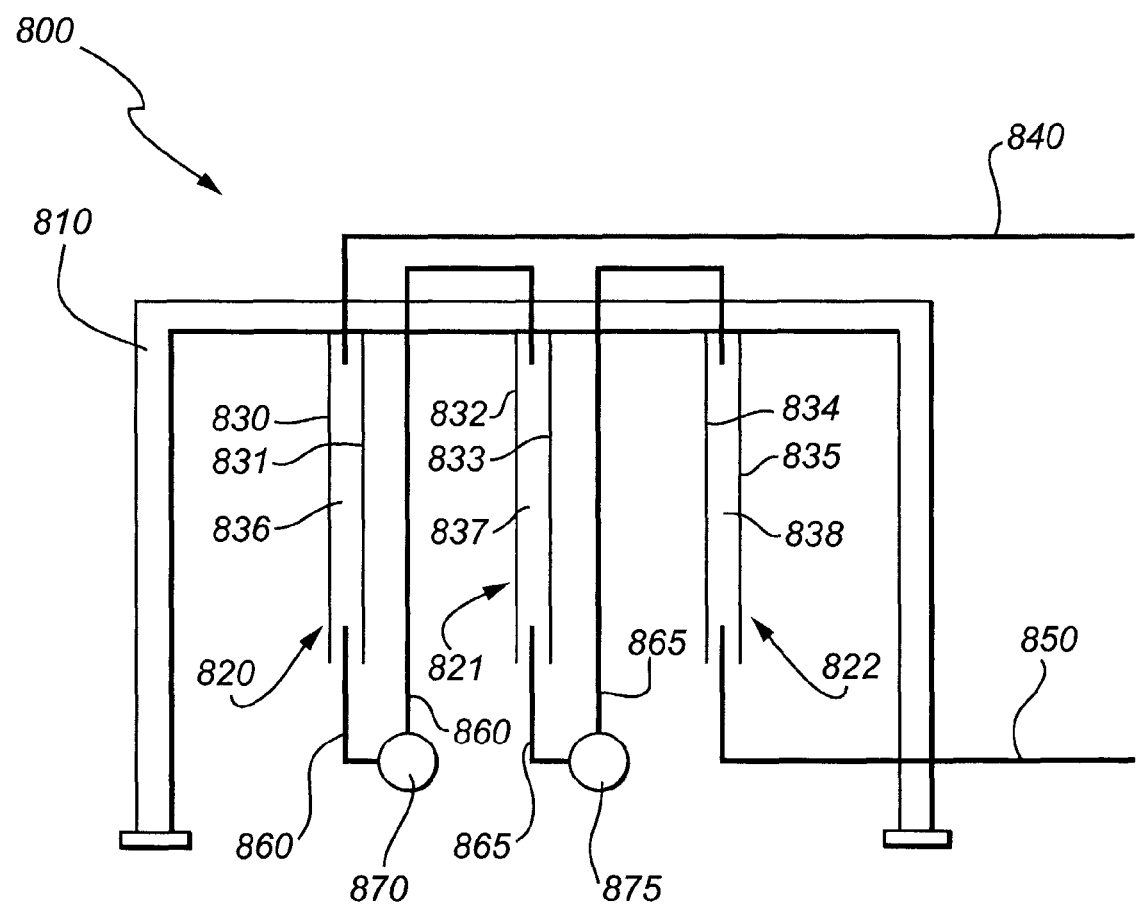
FIG. 3d is a diagrammatic representation of another bioreactor according to the invention.

FIG. 3d shows another bioreactor according to the invention. This bioreactor has pairs of membranes configured in sequence. In FIG. 3d, bioreactor 800 has membrane-supporting structure 810 and pairs 820, 821 and 822 of membranes 830 and 831, 832 and 833, and 834 and 835 respectively supported thereon. Pairs 820, 821 and 822 have inner regions 836, 837 and 838 respectively. Inlet 840 is connected to inner region 836 of pair 820, and outlet 850 is connected to inner region 838 of pair 822. Connecting pipe 860 connects inner regions 836 and 837, and is provided with pump 870, and connecting pipe 865 connects inner regions 837 and 838, and is provided with pump 875. In operation, nutrient solution passes through pipe 840 to inner region 836, from where it diffuses through membranes 830 and 831 to the biolayers thereon (not shown). Products diffuse through the membranes to inner region 836. The nutrient solution then passes out of region 836 through pipe 860 and is pumped by pump 870 into inner region 837, where it diffuses through membranes 832 and 833 as described above for membranes 830 and 831. On exiting inner region 837 through pipe 865, the nutrient solution is pumped by pump 875 to inner region 838, where it diffuses through membranes 834 and 835 as described above for membranes 830 and 831. Finally, the nutrient solution, containing any products produced by membranes 830 to 835, exits through outlet 850. The nutrient solution may be recycled through a recycling system such as those shown in FIGS. 3b and 3c.

Figure 4:
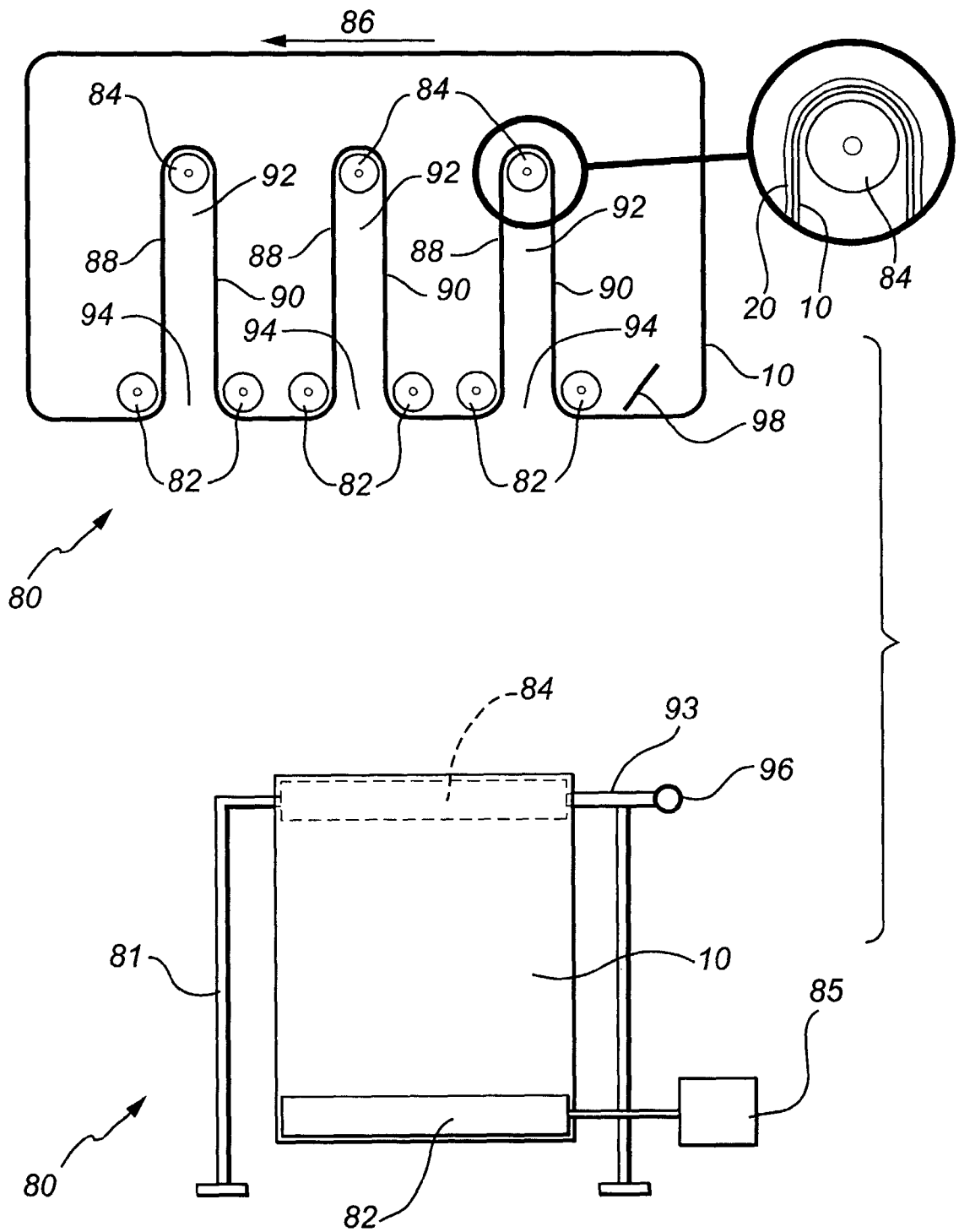
FIG. 4 is a diagrammatic representation of another bioreactor according to the invention.

FIG. 4 is a diagrammatic representation of another bioreactor according to the invention. The upper portion of FIG. 4 shows a side view of bioreactor 80 and the lower portion shows a vertical cross-sectional view thereof. Bioreactor 80 comprises membrane-supporting structure 81 and membrane 10 supported on membrane-supporting structure 81. Membrane 10 has biolayer 20 supported thereon. Membrane supporting structure 81 comprises rollers 82 and perforated rollers 84, which are capable of rotating in a clockwise direction. At least one of rollers 82 and 84 is motor driven by motor 85 in order to move membrane 10 in the direction of arrow 86. Membrane-supporting structure 81 supports membrane 10 in a configuration in which portions 88 of membrane 10 are parallel to other portions 90 respectively so as to define inside regions 92 between them. Bioreactor 80 has inlets 93 for admitting the nutrient solution via perforated rollers 84 to inside regions 92, and has outlets 94 for removing the nutrient solution from inside regions 92. Inlets 93 are connected to inlet manifold 96 and to perforated rollers 84. Bioreactor 80 has scraper 98 for removing solid matter from membrane 10.

In operation, nutrient solution is supplied to perforated rollers 84 through inlet manifold 96 and inlets 93. The nutrient solution is a suitable nutrient solution for the cells of biolayers 20, and may for example contain carbohydrates. Bioreactor 80 is located in an aerobic environment, thereby exposing biolayer 20 to air. Nutrient solution passes out of rollers 84 into regions 92, from where it is allowed to diffuse through membranes 10 to biolayers 20. Biolayers 20 are thus provided with the conditions required for producing the desired product, for example penicillin. This product diffuses through membrane 10 to regions 92, and exits bioreactor 80 in the nutrient solution through outlets 94. The exiting nutrient solution may be collected for separation of the desired product. In the event that biolayer 20 becomes sufficiently thick that production of product is retarded due to lack of oxygen to portions thereof, motor 85 can be operated, causing membrane 10 to move in the direction of arrow 86. Membrane 10 is thereby passed by scraper 98, which is positioned so as to remove excess biomass from biolayer 20. The excess biomass may be collected for use or further processing. In an alternative mode of operation, motor 85 may be operated continuously at a slow speed, such that when a portion of membrane 10 that has had biolayer 20 growing on it for sufficient time to require removal of biomass, that portion is passed by scraper 98 for scraping. For example if the total length of membrane 10 that is exposed to appropriate conditions for growth of biolayer 20 is L metres, and biolayer 20 requires T hours to grow sufficient biomass to require removal, and the circumference of roller 82 which is driven by motor 85 is C metres, then motor 85 will turn roller 82 at L/(T*C) revolutions/hour.

Figure 5:
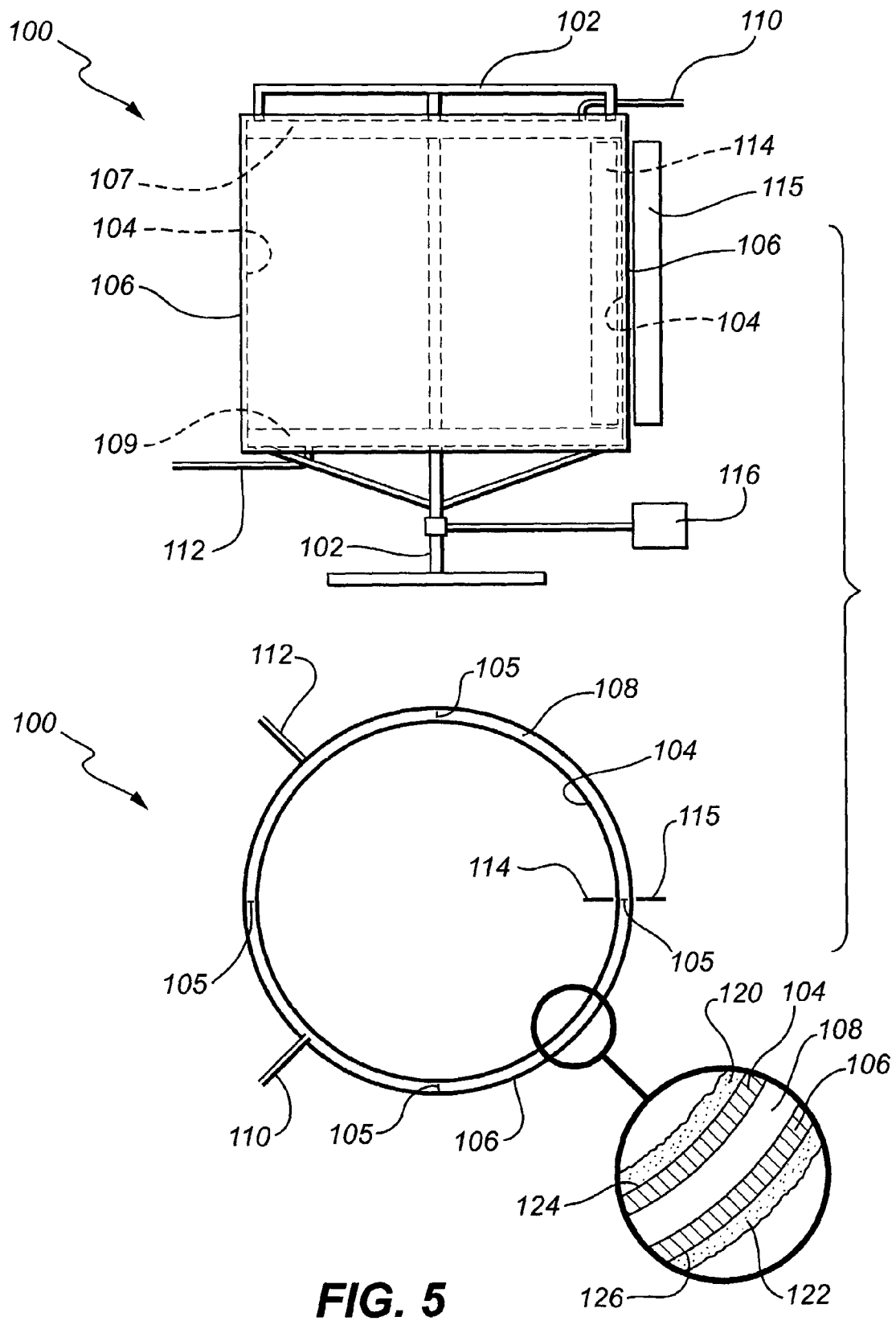
FIG. 5 is a diagrammatic representation of yet another bioreactor according to the invention.

FIG. 5 is a diagrammatic representation of yet another bioreactor according to the invention. The upper section of FIG. 5 shows a side view of bioreactor 100 and the lower section shows a horizontal cross-sectional view thereof. Bioreactor 100 comprises membrane-supporting structure 102, and inner membrane 104 and outer membrane 106 supported between inlet ring 107 and outlet ring 109, which are parts of membrane-supporting structure 102. Membranes 104 and 106 are tubular and concentric, and define inside region 108 between them. Perforations in inlet ring 107 and outlet ring 109 open into region 108 to allow passage of liquid from ring 107 to region 108 and from region 108 into ring 109. Membranes 104 and 106 each have an immobilised biolayer 120 and 122 respectively, comprising cells, on the gas face (124 and 126 respectively) thereof. Spacers 105 are located in inside region 108 for maintaining a distance between membranes 104 and 106. Bioreactor 100 has inlet 110 for admitting nutrient solution to region 108 via inlet ring 107, and has outlet 112 for removing the nutrient solution from region 108 via outlet ring 109. Bioreactor 100 has scrapers 114 and 115 for removing solid matter from biolayers 120 and 122 respectively. Motor 116 is provided for rotating membranes 104 and 106 relative to scraper 114 and 115 respectively to assist with removing excess biomass from biolayers 120 and 122 of membranes 104 and 106.

In operation, nutrient solution is supplied to inlet ring 107 through inlet 110. The nutrient solution is a suitable nutrient solution for the fungi of biolayers 120 and 122, and may for example contain carbohydrates. Bioreactor 100 is located in an aerobic environment, thereby exposing biolayers 120 and 122 to air. Nutrient solution passes from inlet ring 107 into region 108, from where it is allowed to diffuse through membranes 104 and 106 to biolayers 120 and 122 respectively. Biolayers 120 and 122 are thus provided with the conditions required for producing the desired product. This product diffuses through membranes 104 and 106 to region 108, and exits bioreactor 100 in the nutrient solution through outlet ring 109 and outlet 112. The exiting nutrient solution may be collected for separation of the desired product. In the event that biolayers 120 and 122 becomes sufficiently thick that production of product is retarded due to lack of oxygen to portions thereof, motor 116 can be operated, causing membranes 104 and 106 to rotate about a vertical axis. Membranes 104 and 106 thereby pass by scrapers 114 and 115 respectively, which are positioned so as to remove excess biomass from biolayers 120 and 122. The excess biomass may be collected for use or further processing. In an alternative mode of operation, motor 116 may be operated continuously at a slow speed, such that when portions of membranes 104 and 106 that have had biolayers 120 and 122 growing on them for sufficient time to require removal of biomass, those portions are passed by scrapers 114 and 115 for scraping.

Figure 5A:
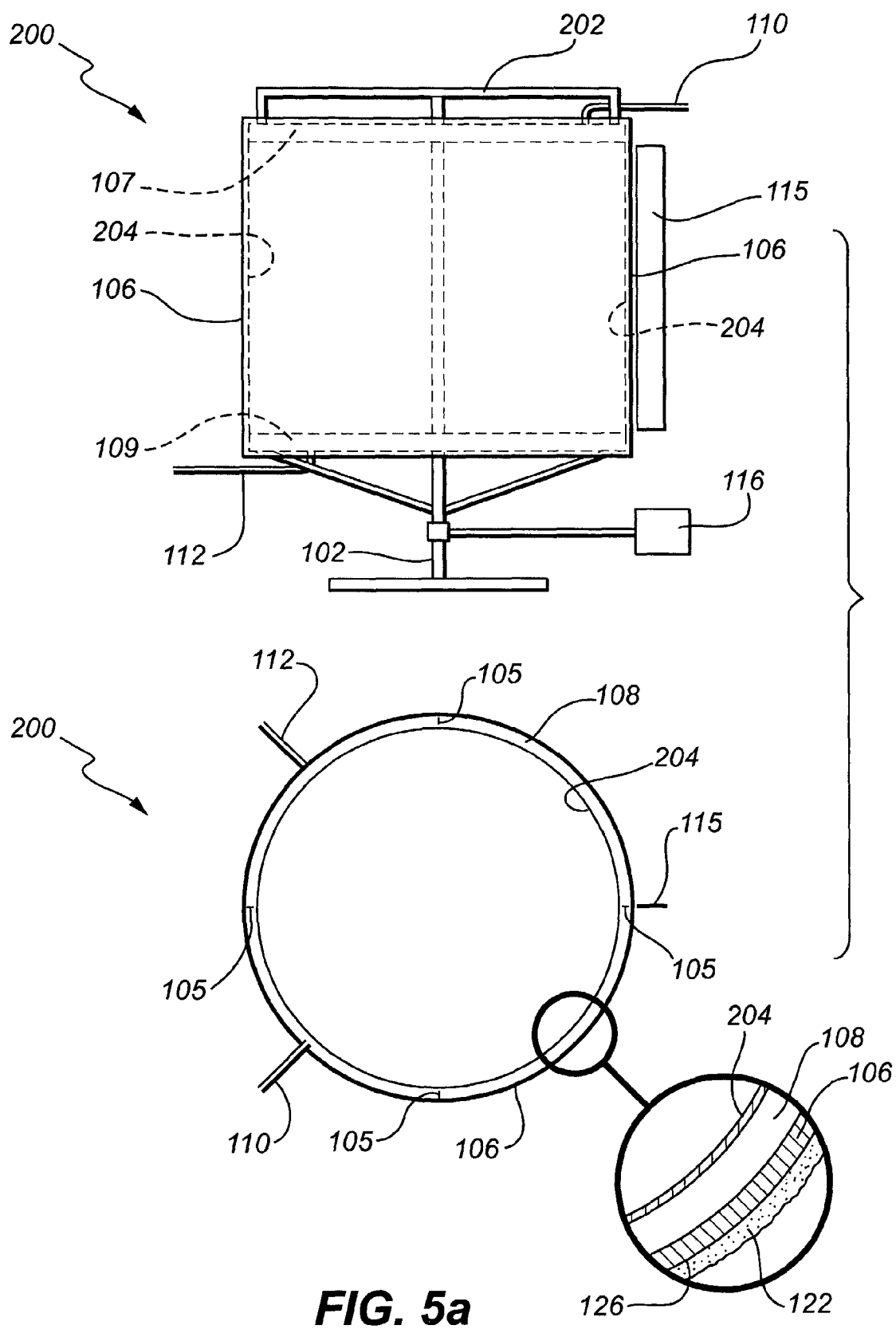
FIG. 5a is a diagrammatic representation of still another bioreactor according to the invention.

FIG. 5a is a diagrammatic representation of still another bioreactor according to the invention. The upper section of FIG. 5 shows a side view of bioreactor 200 and the lower section shows a horizontal cross-sectional view thereof. Bioreactor 200 comprises membrane-supporting structure 202, inside support 204 (which is part of support structure 202) and membrane 106 supported between inlet ring 107 and outlet ring 109, which are parts of membrane-supporting structure 202. Inside support 204 is a non-porous support comprising a material that is impervious to the nutrient liquid, and may for example comprise stainless steel or some suitable rigid polymeric material such as polycarbonate. Membrane 106 is tubular and is concentric with inside support 204, and inside region 108 is defined between those two. Perforations in inlet ring 107 and outlet ring 109 open into region 108 to allow passage of liquid from ring 107 to region 108 and from region 108 into ring 109. Membrane 106 has immobilised biolayer 122, comprising fungi, on gas face 126 thereof. Spacers 105 are located in inside region 108 for maintaining a distance between membranes 106 and inside support 204. Bioreactor 200 has inlet 110 for admitting nutrient solution to region 108 via inlet ring 107, and has outlet 112 for removing the nutrient solution from region 108 via outlet ring 109. Bioreactor 200 has scraper 115 for removing solid matter from biolayer 122. Motor 116 is provided for rotating membrane 106 relative to scraper 115 to assist with removing excess biomass from biolayer 122 of membrane 106.

In operation, nutrient solution is supplied to inlet ring 107 through inlet 110. The nutrient solution is a suitable nutrient solution for the fungi of biolayer 122, and may for example contain carbohydrates. Bioreactor 200 is located in an aerobic environment, thereby exposing biolayer 122 to air. Nutrient solution passes from inlet ring 107 into region 108, from where it is allowed to diffuse through membrane 106 to biolayer 122. Biolayer 122 is thus provided with the conditions required for producing the desired product. This product diffuses through membrane 106 to region 108, and exits bioreactor 200 in the nutrient solution through outlet ring 109 and outlet 112. The exiting nutrient solution may be collected for separation of the desired product. In the event that biolayer 122 becomes sufficiently thick that production of product is retarded due to lack of oxygen to portions thereof, motor 116 can be operated, causing membrane 106 to rotate about a vertical axis. Membrane 106 thereby passes by scraper 115, which is positioned so as to remove excess biomass from biolayer 122. The excess biomass may be collected for use or further processing. In an alternative mode of operation, motor 116 may be operated continuously at a slow speed, such that when a portion of membrane 106 that has had biolayer 122 growing on it for sufficient time to require removal of biomass, that portion is passed by scraper 115 for scraping.

Figure 20:
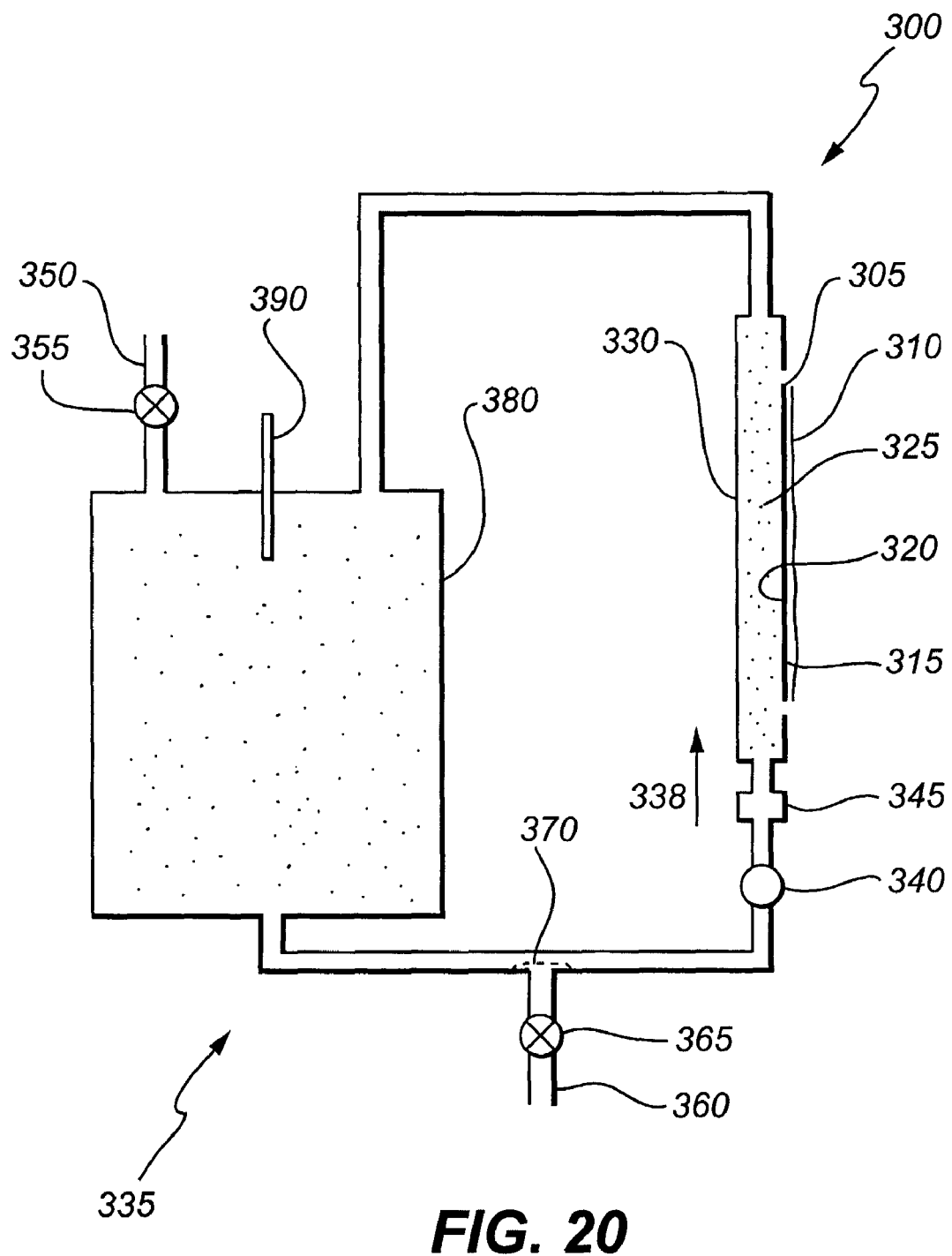
FIG. 20 is a diagrammatic representation of a bioraeactor according to the present invention, wherein the nutrient stream is fed from the lower end of the membrane.

With reference to FIG. 20, bioreactor 300 comprises membrane 305 having biolayer 310 on gas face 315 thereof. Nutrient face 320 of membrane 305 is exposed to nutrient solution 325 in nutrient chamber 330, and biolayer 310 is exposed to air outside chamber 330. Membrane 305 may be supported, if necessary, by a support matrix, not shown, or it may be self supporting. Nutrient solution 325 may optionally have encapsulated anaerobic cells (not shown) suspended therein. Bioreactor 300 also has recycling system 335, for recycling nutrient 325 past membrane 305 in the direction of arrow 338 by means of recirculator (e.g. pump) 340. By recycling in this direction, chamber 330 is maintained full with no gas space above. Recycling system 335 may have deoxygenator 345 for removing oxygen from nutrient solution 325. System 330 also has inlet 350, fitted with valve 355, and outlet 360, fitted with valve 365, and optionally filter 370 for preventing the encapsulated anaerobic cells, if present, from leaving bioreactor 300. Bioreactor 300 also has reservoir 380, which is sealed from ingress of oxygen, for holding nutrient solution that is recycled through chamber 330. Detector 390 is provided to detect a level of a component of nutrient solution 325. Thus in operation nutrient enters bioreactor 300 through inlet 350 with valve 355 open and valve 365 shut. Valve 355 is then closed and nutrient solution 325 recirculates through reservoir 380 and chamber 330 in the direction of arrow 338. Nutrient stream 325 is rendered and maintained anoxic by means of deoxygenator 346. In chamber 330, nutrient diffuses through nutrient face 320 of membrane 305 to biolayer 310 where it is metabolised, for example to form desirable products, or to remove undesirable matter from nutrient solution 325. Biolayer 310 obtains oxygen for metabolism from air outside the chamber to which it is exposed. Metabolites, e.g. desirable products, may then diffuse back into chamber 330 and recycle with nutrient solution 325. If present, the encapsulated anaerobic cells also metabolize components of the nutrient stream to produce metabolites as nutrients diffuse through encapsulant to the encapsulated cells. Detector 390 determines when the bioreaction of the biolayer has proceeded sufficiently, either by determining when a level of a nutrient solution component has dropped to a predetermined level or be determining when a level of metabolite has increased to a predetermined level. Nutrient solution 325 may then be removed from bioreactor 300 through valve 365. Encapsulated anaerobic cells, if present, are retained in bioreactor 300 by filter 370. Products (metabolites) may then be recovered from nutrient solution 325 separately. Detector may trigger opening of valve 365 automatically, or may signal an operator to open valve 365 manually. Alternatively, valve may be opened (either manually or automatically) after a predetermined time.

Applications

The bioreactor of the present invention may be used in many applications. These include:
  Antibiotic, other pharmaceuticals and cosmetics production;
  Sewerage treatment;
  Heavy metal removal/recovery;
  Bioleaching and other mining applications;
  Biosynthesis (food and chemicals for industry and research);
  Secondary and tertiary treatment of waste waters, for the removal of carbon, nitrogen, phosphorous, and metal ions;
  Bioremediation of toxic waste waters;
  Polishing of contaminated drinking water;
  Culture of animal and plant tissues.
  Any field where cultured aerobic cells are used;
  Growth of food (for example for space industry);
  Use of animal tissues for biosynthesis;
  Recovery of organic material for fuel production (biofuel);
  Animal tissues culture for artificial organs and implantation and for biosynthesis of hormones and other mammalian-derived pharmaceuticals;

Advantages

The bioreactor of the present invention offer a variety of advantages over the prior art.
  These include:
  Higher membrane porosity—the biolayer is supported within a high-porosity membrane. This has a higher availability of nutrients than that provided by other membranes used for this purpose (e.g. ceramic membrane bioreactor);
  Less expensive membrane—since biomass is discouraged from growing on the nutrient side of the membrane by the relatively anoxic conditions there, there is no requirement for a membrane with pores sufficiently small to prevent penetration of the microorganisms of the biomass. Consequently membranes that are less expensive than those used in conventional membrane-surface-liquid-culture bioreactors may be used.
  Membrane is easily made—the membranes of the present invention apart from being inexpensive, may be made using simple techniques and inexpensive readily available equipment. Making the membrane may be quick. This may enable use of the membranes as a disposable item if required.
  Thin, well-dispersed biolayer—the diffusion distances for dissolved oxygen and nutrients are relatively short, ensuring that the biolayer is supplied with an abundant quantity of metabolites;
  Air-cooled—the reactor assembly may be cooled by natural convection, and thus no expensive refrigeration is required;
  Low weight—no major building infrastructure is required to support the bioreactor of the invention, enabling them to be readily deployed;
  Inexpensive—the components are inexpensive and readily available;
  Operates at ambient pressure—the biological processes being exploited all operate at ambient pressure, thus avoiding the need for expensive high-pressure infrastructure;
  Culture grows mostly on the gas face of the membrane of the bioreactor—this increases the contact area between the biolayer and gas phase and more effectively removes the biolayer from the nutrient solution;

Double sided—increases the surface area of the system relative to single-sided systems;

Flexible membrane—makes the membrane more durable and capable of being deployed in almost any desired shape;

Easy separation of products—The biolayer is separated at all times from the nutrient solution;

Low running costs;

No special expertise—the systems are simple and minimal training is required to operate them;

Potential for automation;

Higher rate of production than conventional bioreactors (two orders of magnitude more than Type 1 ceramic membrane bioreactor and up to 40 times faster than current airlift bioreactor configuration for penicillin production);

Wide choice of biolayer—Suitable for bacteria, yeast, fungi, animal, and plant cells;

Minimal footprint—membranes may be vertically hung;

High product yields—higher yield per unit of substrate consumed;

Greater rate of growth of biolayer;

Continuous flow—can be used in continuous mode convenient for sequential processing.

Regenerable—Biolayer is able to be effectively washed and can be re-used/recycled many times High delivery of gas—facilitates full function of the immobilized culture Flexible reactor structure—can be deformed without damaging the membrane;

Relatively infrequent downtime to commence operations with a new batch of biomass;

Short lag time between addition of nutrients and product generation (concurrent primary and secondary metabolism);

Improved longevity of biolayer;

Simultaneous secondary and tertiary treatment;

Easy separation of biomass, with rapid culture regrowth following biomass removal.

EXAMPLE 1

Penicillin Biosynthesis and Carbohydrate Consumption Assay

Closed-System Nanoparticulate Membrane Bioreactor

Four pouches were made from woven glass fabric to be 90×80 mm and assembled on stainless steel frames suspended in a 1000 ml beaker covered with an aluminium foil lid. The woven glass matting used had 22 strands per cm and weighed 80 g/m². To make the glass wettable it was plasma etched as described later. Thereafter, all techniques were aseptic and performed in a class II biosafety cabinet. 40 ml of gamma ray-sterilized colloidal silica solution (Bindzil T, Eka Chemicals) at pH 10, was adjusted to pH 6 using universal indicator and 4.0 M HCl, to initiate gelation. 4.0 ml of $P.$ $chrysogenum$ spore suspension containing $8.0\times10^{10}$ cfu/ml was added to the gelling silica sol. 10.0 ml of colloidal silica was adjusted to pH 6 in the same way and was doped with 1.0 ml of $A.$ $niger$ spore suspension containing $9.0\times10^{10}$ cfu/ml. Approximately 8.0, 10.0 and 12.0 ml of $P.$ $chrysogenum$-doped colloidal silica was soaked into each of three glass pouches. Approximately 8.0 ml of $A.$ $niger$-doped colloidal silica was soaked into a fourth pouch. All were allowed to gel and aged overnight at 20° C. to prevent redispersion, before 100 ml of Wickerham's malt yeast extract broth (MYEB) containing malt extract, 3.0 g/l; peptone, 5.0 g/l; yeast extract, 3.0 g/l; and glucose, 10 g/l, was added to the lumen of each pouch. Initially the Nanoparticulate Membrane Bioreactors (NMBs) were leaky, so the effluent was returned to the lumen via a peristaltic pump with a flow rate greater than the rate of efflux, so that the lumen was full at all times. The broth filled the pouch to within 10 mm of the top, making the area of culture 80×80 mm on each side, giving a total of 128 cm² of cultured membrane. The pouches were incubated at 28° C. 1.0 ml samples were taken from each NMB daily, and were analysed for carbohydrate concentration and pH. The $P.$ $chrysogenum$ culture was also tested for penicillin production via the disc-diffusion assay method. The MYEB was removed every 4 days. 100 ml of sterile 0.85% saline was used to wash each bioreactor for one hour. The saline was sampled and analysed for penicillin ($P.$ $chrysogenum$ only) and the remainder was discarded. 100 ml of fresh MYEB was replaced in the NMB to start the next batch. 1.0 ml samples were taken at the start of each batch. Except for the $P.$ $chrysogenum$ culture in the sparged bioreactor (described below), each batch lasted four days. After eight batches the biomass was aseptically scraped from the NMB with a spatula, before the next batch was commenced with fresh MYEB.

Sparged Bioreactors (SB)

Two scaled sparged bioreactors (SB) were assembled from 500 ml Schott bottles with two-holed stoppers. One tube sparged sterile filtered air at a rate of approximately 1.0 L/minute through 100 ml of MYEB in the bottom of each vessel. Another tube carried the air efflux through another filter for release. The bioreactors were inoculated with 1.0 ml of spore suspension ($P.$ $chrysogenum$ and $A.$ $niger$ as described above) and incubated at 28° C. 1.0 ml samples were taken daily and analysed as described for the Nanoparticulate Membrane Bioreactors above. For $P.$ $chrysogenum$ in the sparged bioreactor the batch was ended when the penicillin concentration fell.

TABLE 1

Metabolic parameters of $P.$ $chrysogenum$ cultured in various bioreactors.

| Bioreactor | Batch | $Y_p$ | $Y_{p/s}$ | $R_p$ | Lag | $[COH]_{Pen}$ |
|---|---|---|---|---|---|---|
| NMB | 1 | 16.8 | 1.2 | 0.18 | 43 | 14.6 |
|  | 2 | 44.3 | 3.4 | 0.64 | 0 | 13.8 |
|  | 3 | 30.7 | 2.4 | 0.32 | 0 | 13.1 |
|  | 4 | 55.8 | 4.3 | 0.59 | 0 | 13.6 |
|  | 5 | 52.8 | 4.3 | 0.54 | 0 | 13.1 |
|  | 6 | 50.4 | 3.9 | 0.72 | 0 | 13.8 |
|  | 7 | 33.9 | 2.8 | 0.34 | 0 | 12.9 |
|  | 8 | 47.3 | 3.8 | 0.49 | 0 | 13.4 |
|  | 9 | 69.3 | 5.2 | 0.88 | 0 | 14.1 |
| SB | 1 | 28.6 | 2.0 | 0.14 | 113 | 0.7 |
|  | 2 | 9.8 | 1.3 | 0.14 | 46 | 4.4 |
| CMB* | 1 | 2.2 | 0.4 | 0.014 | 98 | 0.8 |

$Y_p$ Yield of penicillin (µg/ml)

$Y_{p/s}$ $Y_p$ divided by the carbohydrate consumed (µg/mg)

$R_p$ Rate of penicillin produced (µg/mlh)

Lag Time (h) taken from the addition of new medium till penicillin production began $[COH]_{Pen}$ Concentration of carbohydrate at which penicillin production began NMB Nanoparticulate-membrane bioreactor SB Sparged bioreactor

*prior art data

TABLE 2

Metabolic parameters of *A. niger* cultured in an NMB and a sparged bioreactor (SB).

| Bioreactor | Batch | $T_D$ | $R_s$ |
|---|---|---|---|
| NMB | 1 | 47 | 0.30 |
|  | 2 | 21 | 0.57 |
|  | 3 | 21 | 0.63 |
|  | 4 | 26 | 0.52 |
|  | 5 | 21 | 0.60 |
|  | 6 | 25 | 0.50 |
|  | 7 | 21 | 0.60 |
| SB | 1 | 66 | 0.22 |
|  | 2 | 45 | 0.24 |
|  | 3 | 46 | 0.26 |
|  | 4 | 72 | 0.17 |
|  | 5 | 69 | 0.17 |
|  | 6 | 71 | 0.17 |
|  | 7 | 116 | 0.10 |

Figure 6:
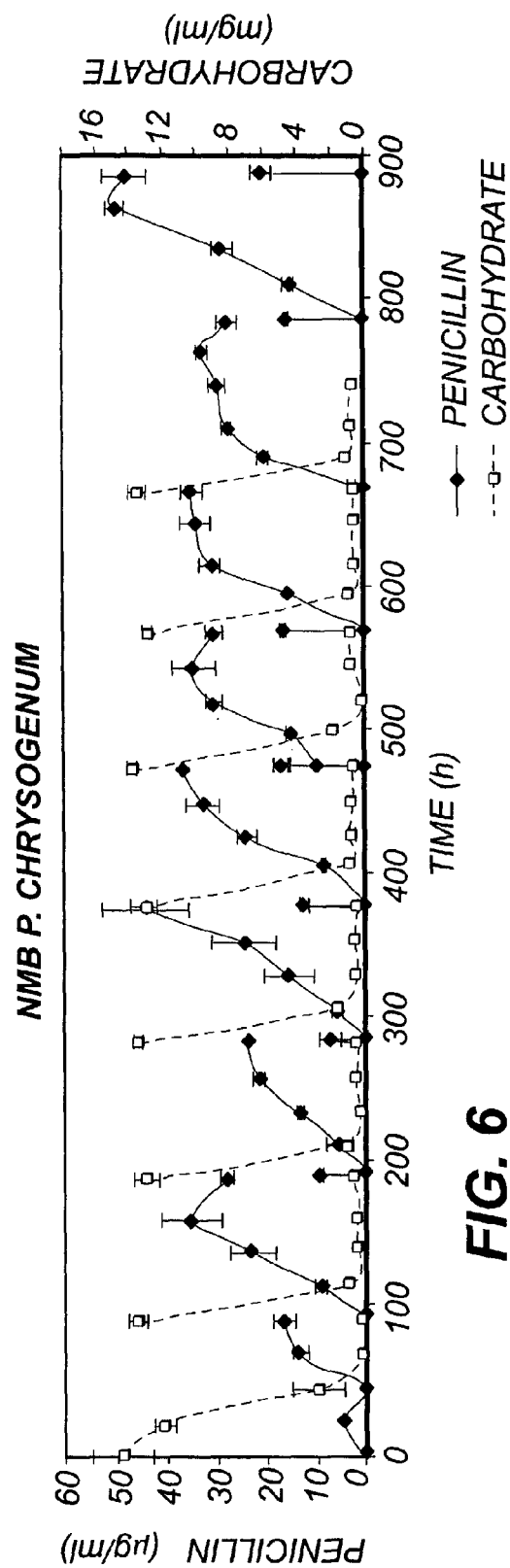
FIG. 6 is a graph of penicillin concentration against time for *P. chrysogenum* in the bioreactor of example 1.
Figure 7:
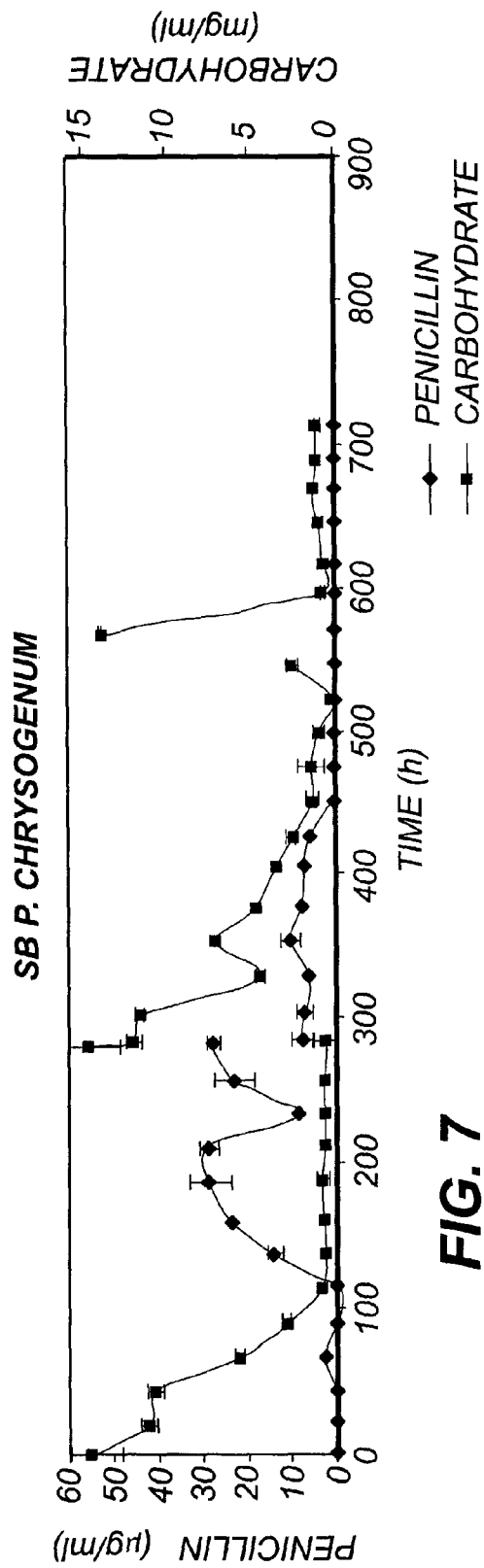
FIG. 7 is a graph of penicillin concentration against time for *P. chrysogenum* in the sparged bioreactor of example 1.
Figure 8:
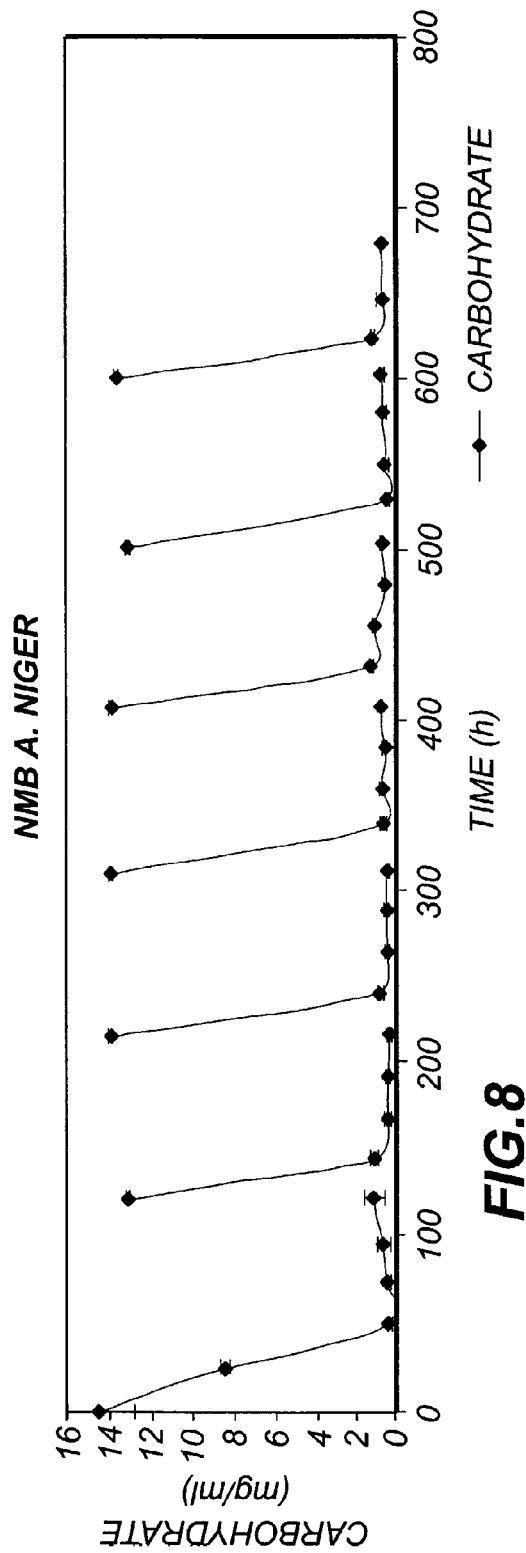
FIG. 8 is a graph of carbohydrate concentration against time for *A. niger* in the bioreactor of example 1.
Figure 9:
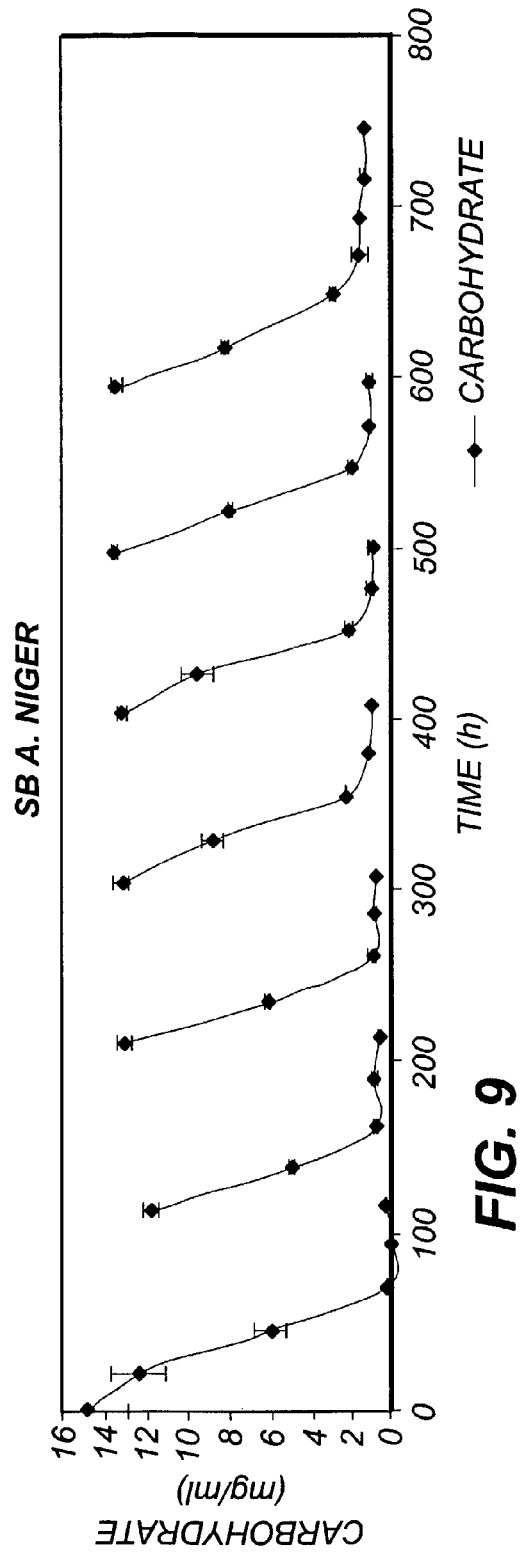
FIG. 9 is a graph of carbohydrate concentration against time for *A. niger* in the sparged bioreactor of example 1.
Figure 10:
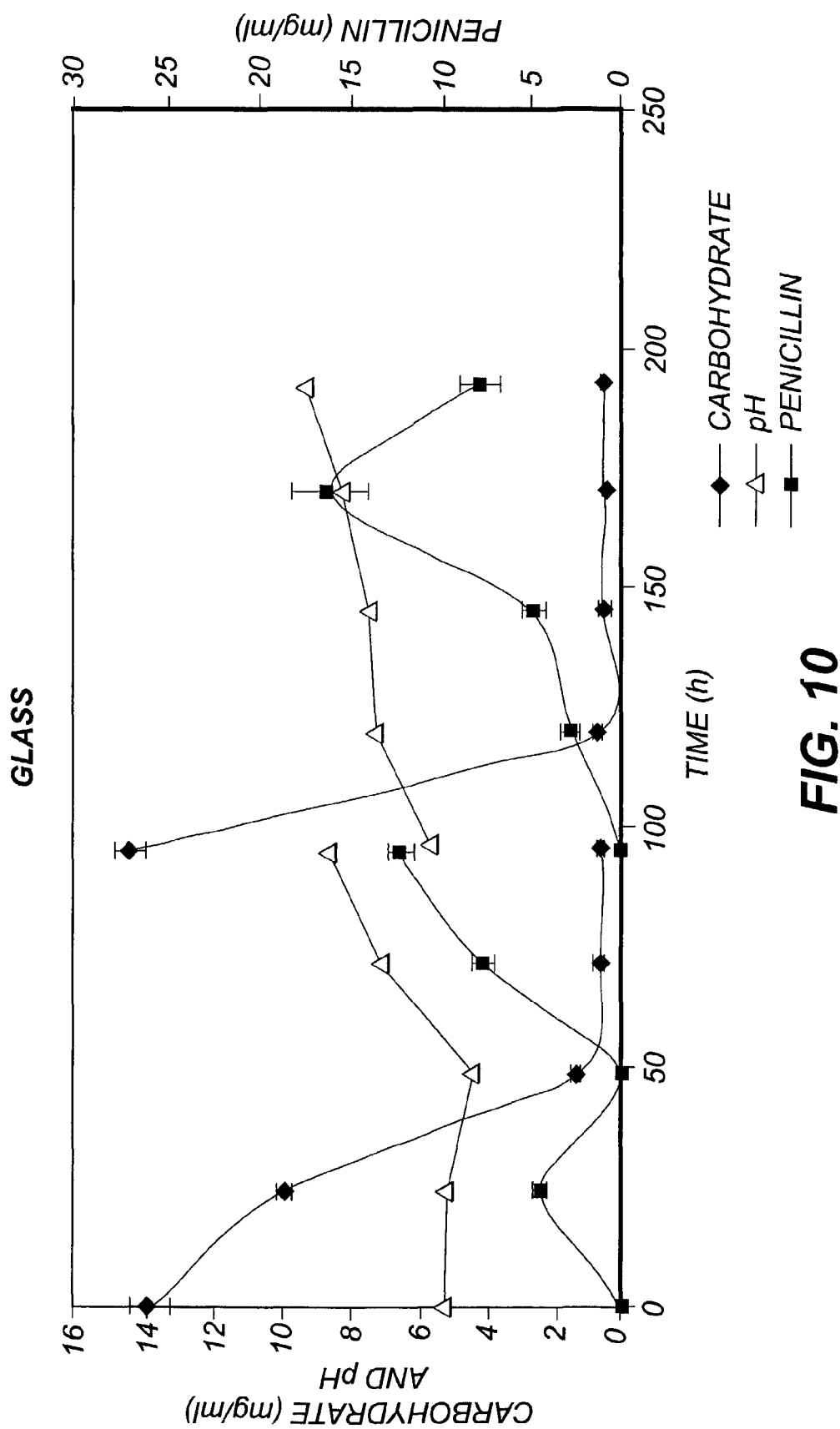
FIG. 10 is a graph of carbohydrate concentration, pH and penicillin concentration against time for *P. chrysogenum* in a bioreactor of example 2 using a glass support.
Figure 11:
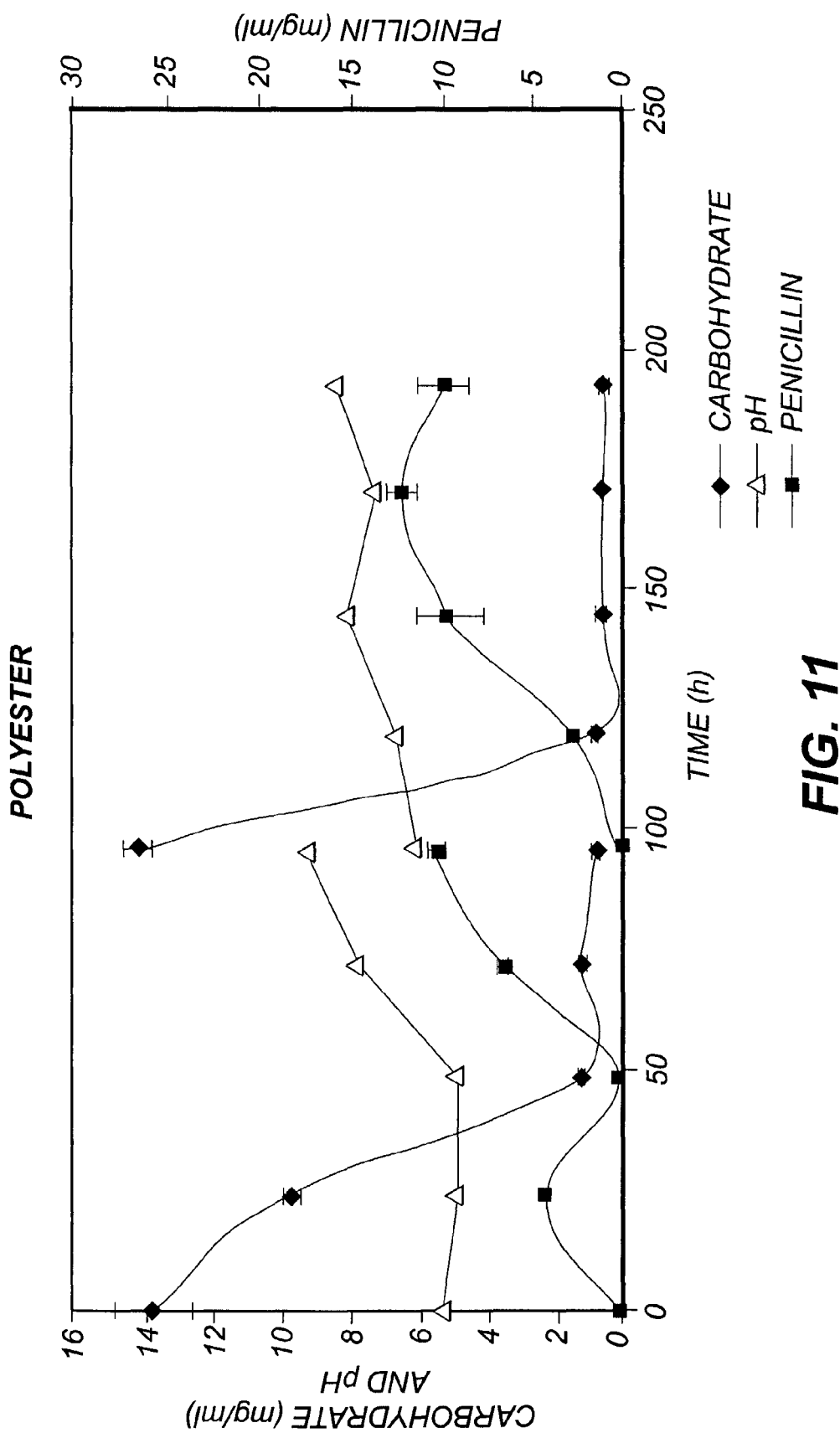
FIG. 11 is a graph of carbohydrate concentration, pH and penicillin concentration against time for *P. chrysogenum* in a bioreactor of example 2 using a polyester support.
Figure 12:
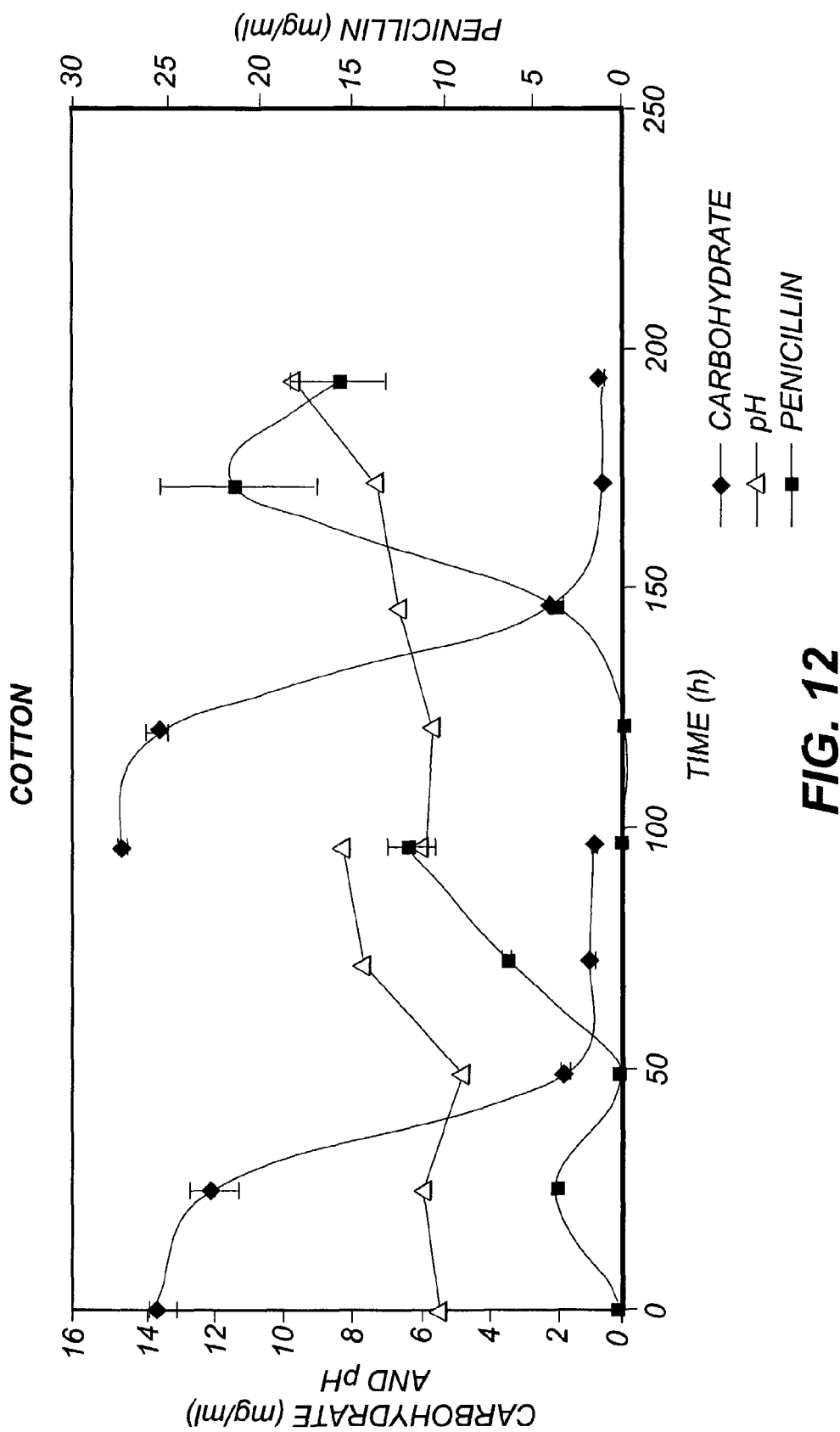
FIG. 12 is a graph of carbohydrate concentration, pH and penicillin concentration against time for *P. chrysogenum* in a bioreactor of example 2 using a cotton support.
Figure 13:
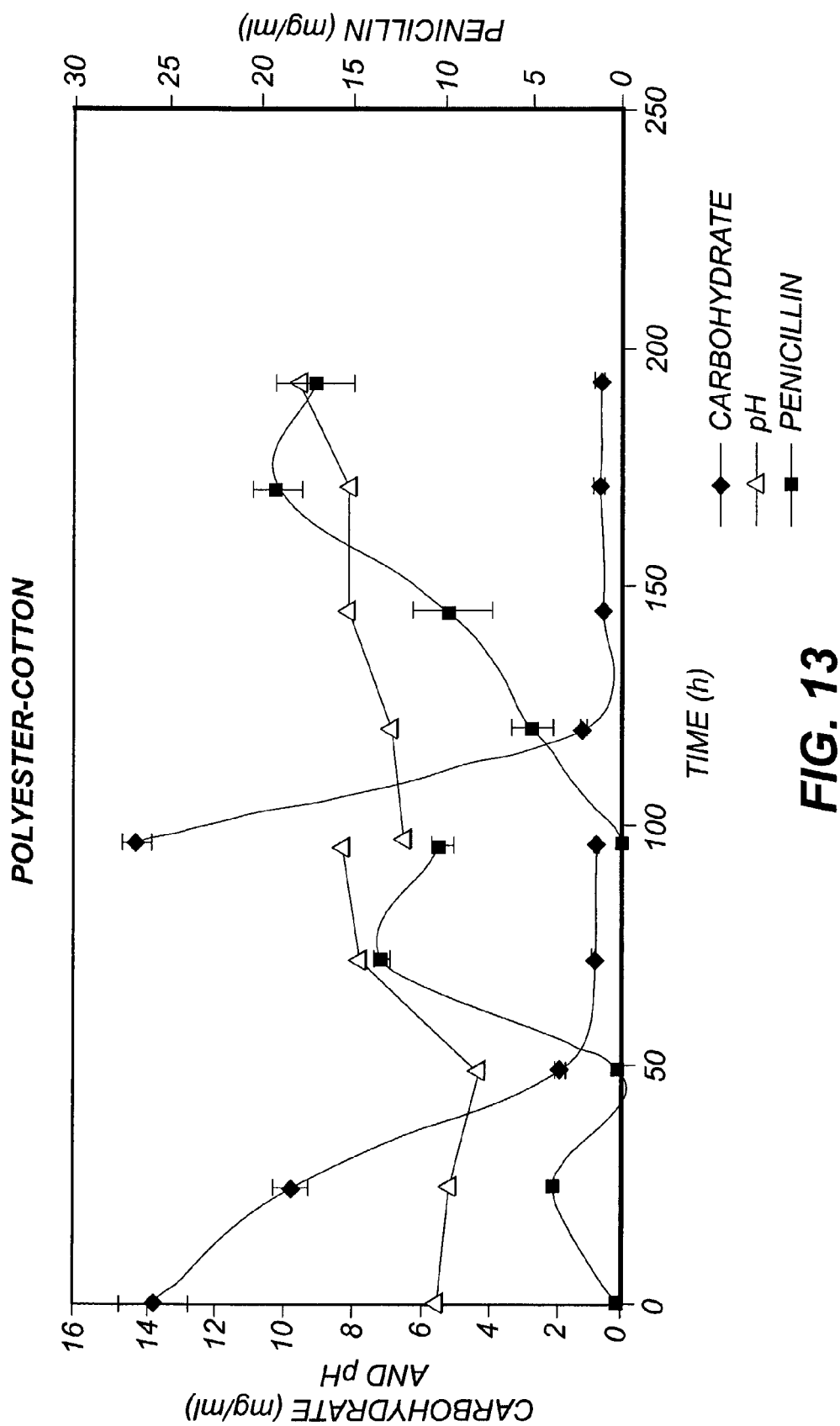
FIG. 13 is a graph of carbohydrate concentration, pH and penicillin concentration against time for *P. chrysogenum* in a bioreactor of example 2 using a polyester-cotton support.
Figure 14A:
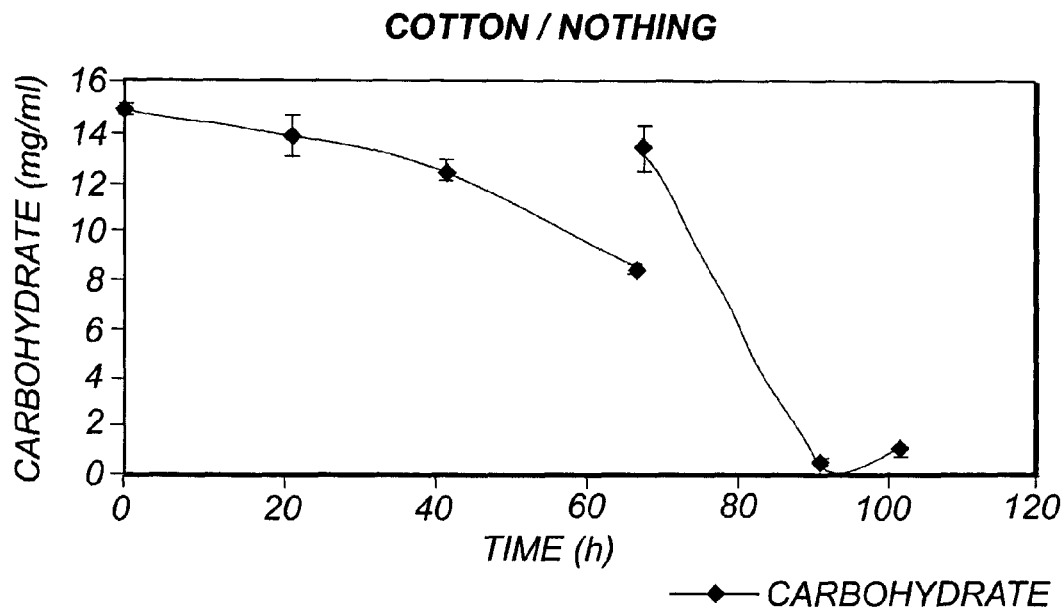
FIG. 14 shows 4 graphs of carbohydrate concentration against time for *A. niger* in the bioreactor of example 2 using a cotton support in FIG. 14a and glass supports in FIGS. 14b-d with various gel materials, including: nothing; agar agar; calcium alginate; and silica gel, respectively.
Figure 14B:
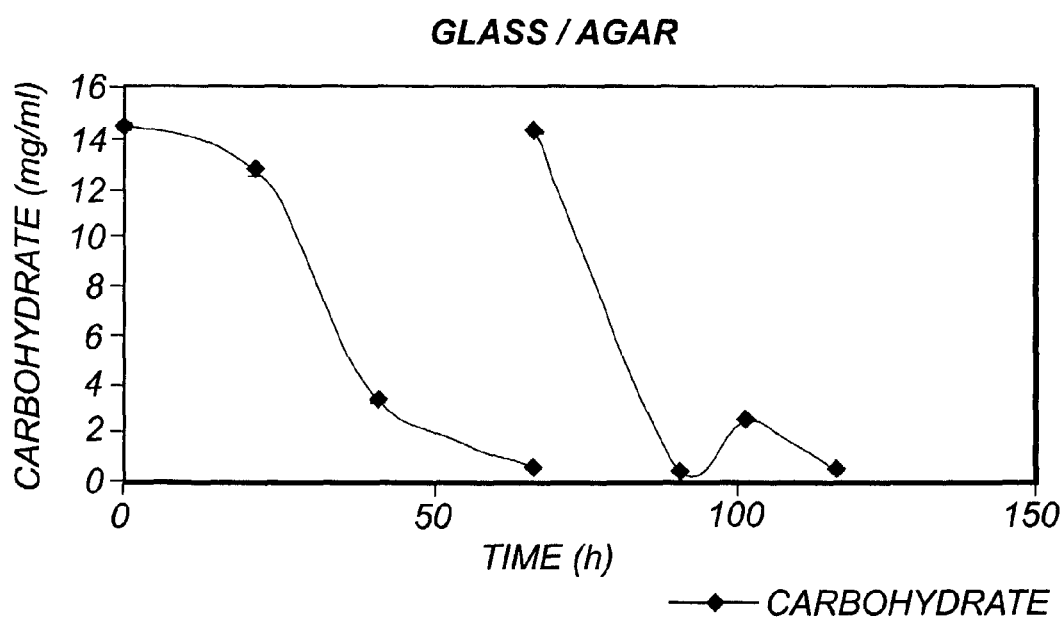
Figure 14C:
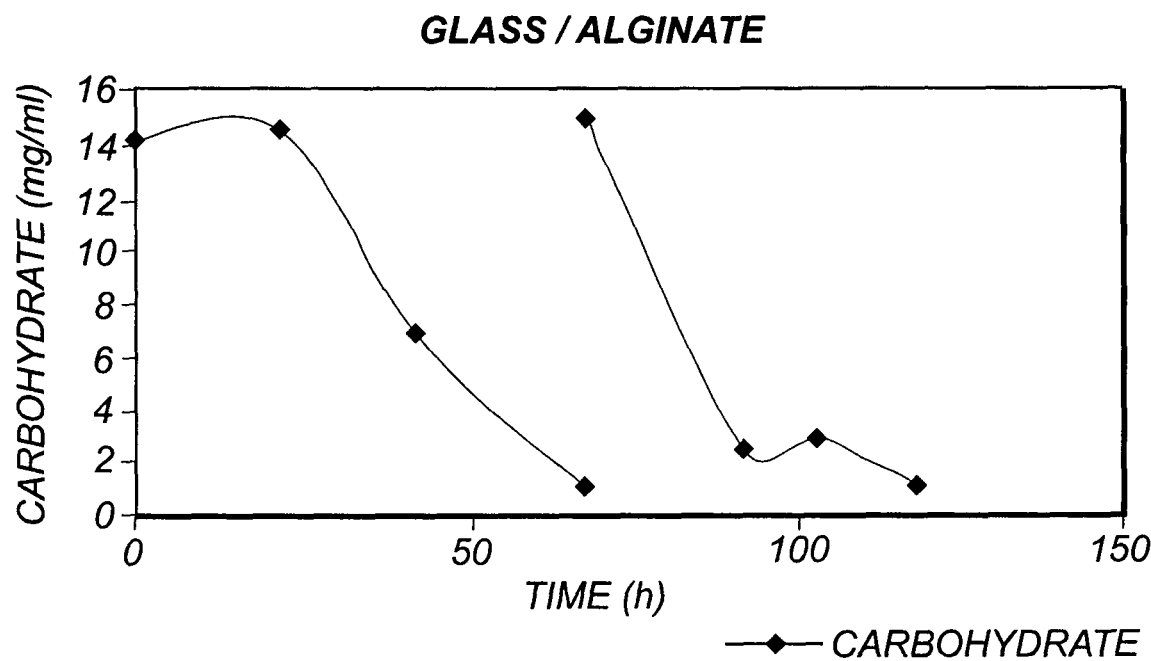
Figure 14D:
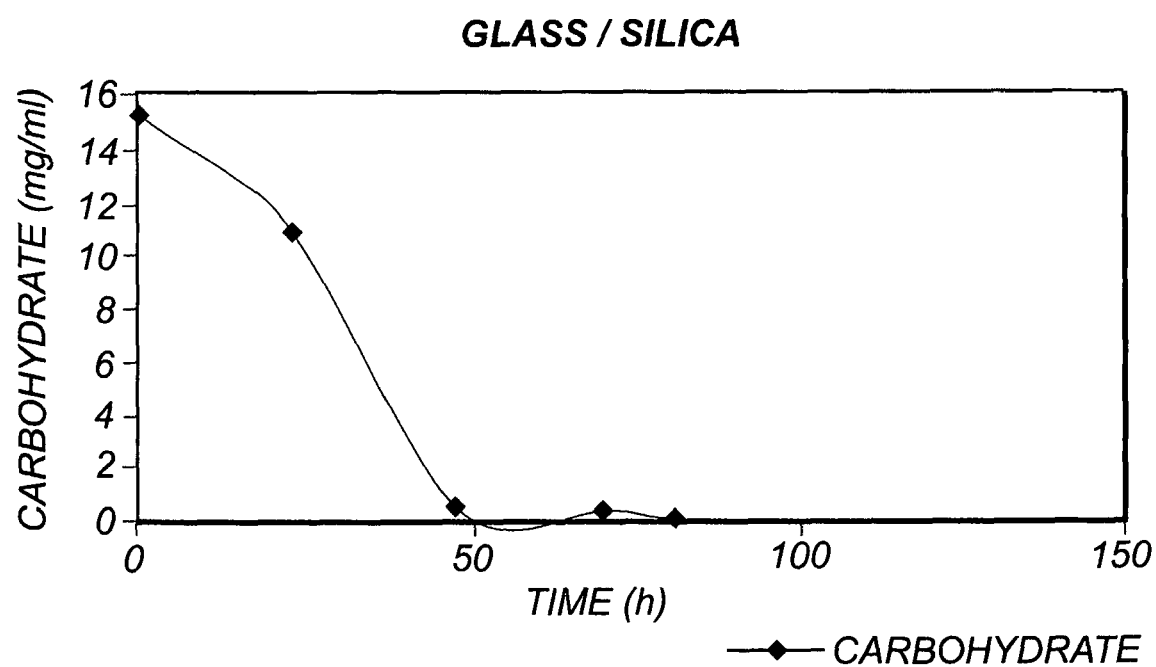
Figure 15A:
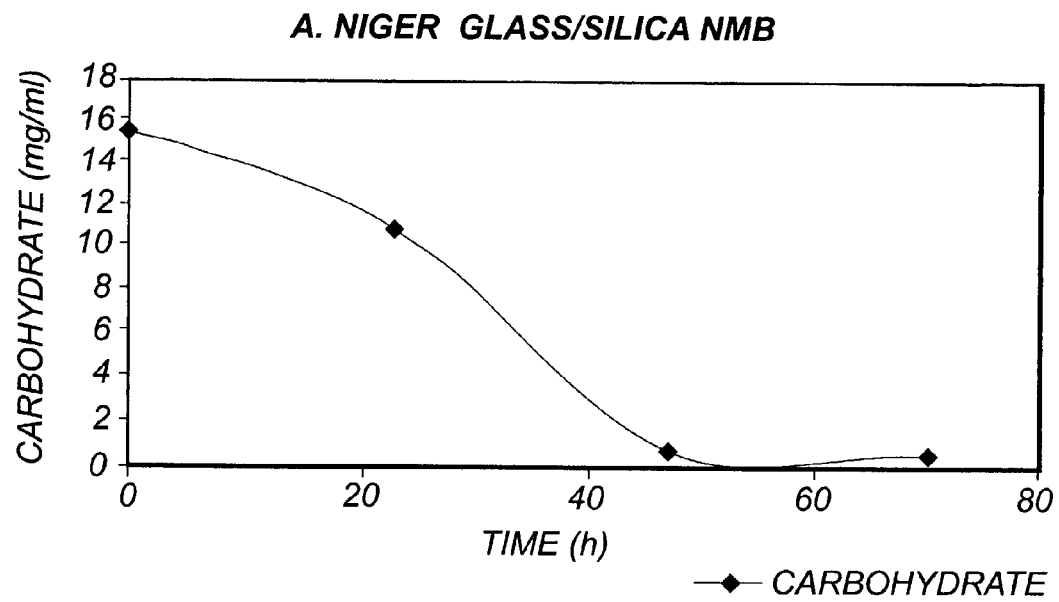
FIG. 15 shows graphs of concentration of various components of a nutrient solution against time for *A. niger* in a bioreactor of example 2 using a glass support and silica gel.
Figure 15B:
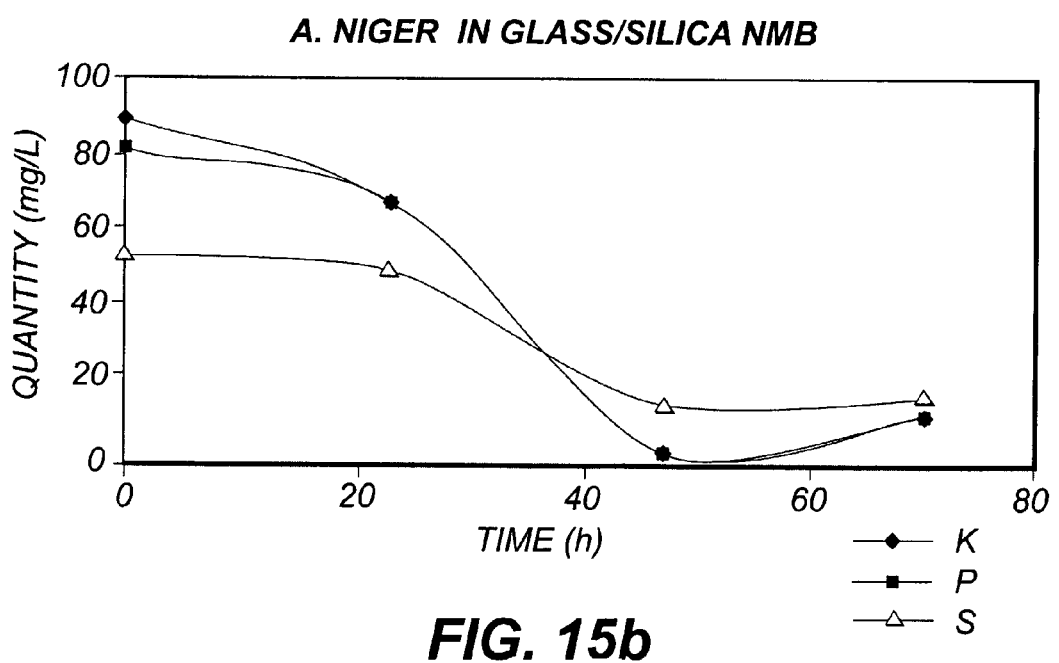
Figure 15C:
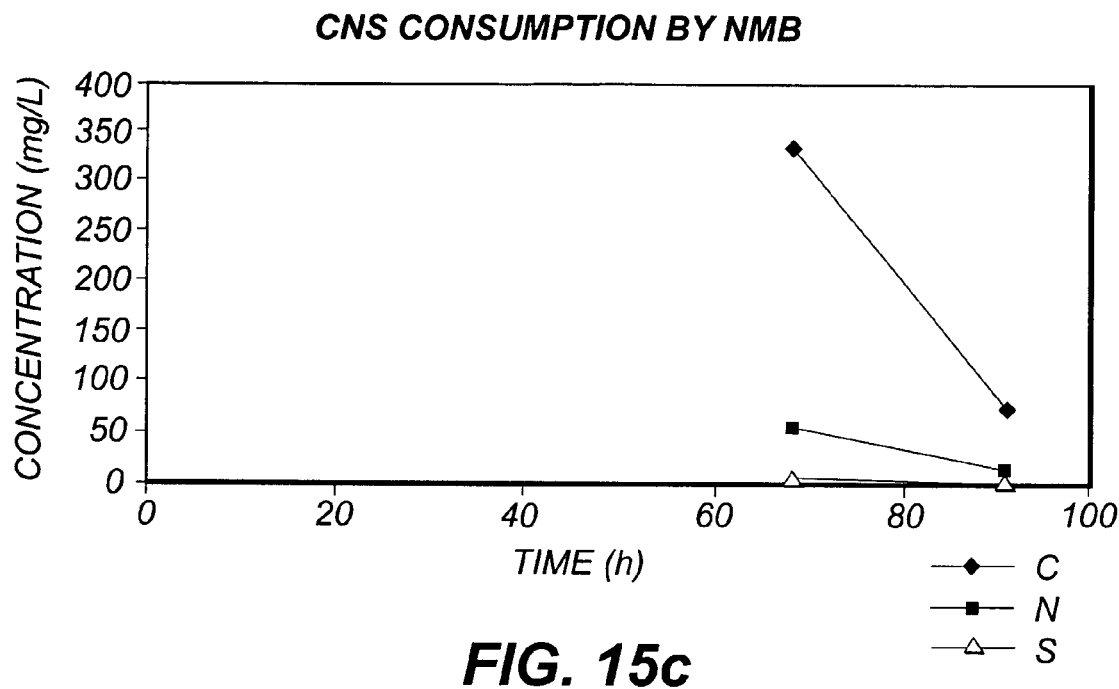
Figure 15D:
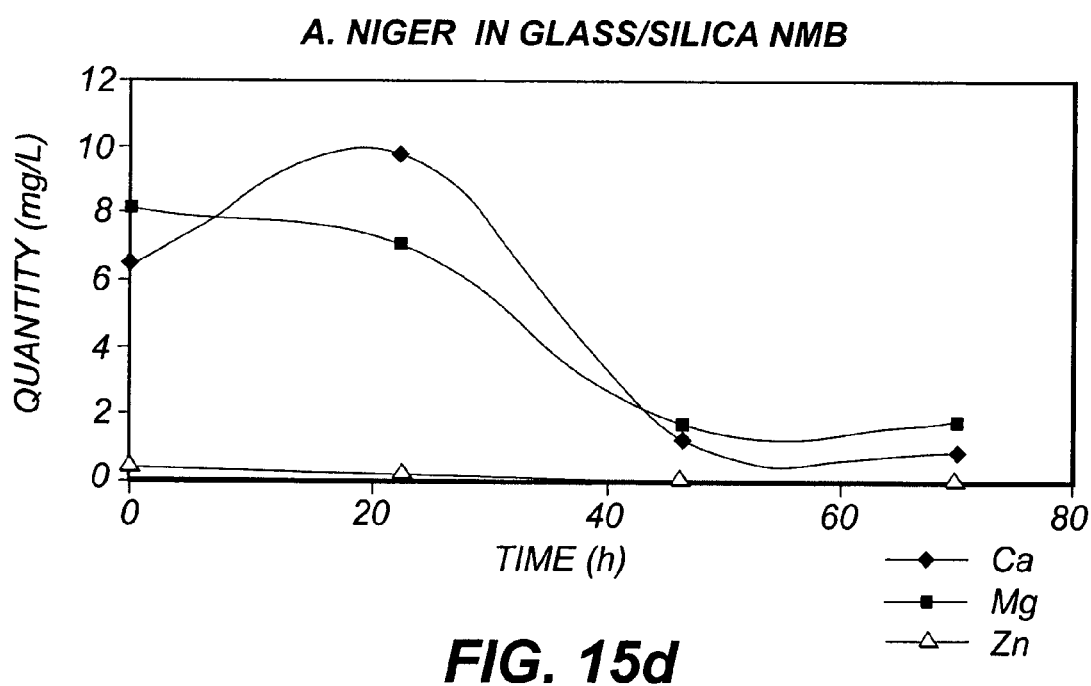

$T_D$ Decimal reduction time for the removal of carbohydrates
$R_s$ Rate of carbohydrate consumption (mg/mlh)
SB Sparged bioreactor Comparison of FIGS. 6 and 7 shows that the bioreactor of the present invention is capable of far more cycles of production before it requires regeneration, and in each cycle, the rate of carbohydrate consumption and penicillin production is greater than in the corresponding sparged bioreactor. Comparison of FIGS. 8 and 9 similarly shows that for *A. niger* in a bioreactor according to the present invention, the rate of carbohydrate consumption is far greater than in the corresponding sparged bioreactor, and the bioreactor is capable of repeated cycles with no observable deterioration of performance.

EXAMPLE 2

Materials assay

Different Materials

Four pouches (90×80 mm) were assembled from woven glass fibre (described in Example 1), cotton (calico), polyester, and polyester-cotton blend (70/30). Fibre densities of the materials were: woven glass material 20 strands/cm; cotton (calico) 20 strands/cm; polyester 26 strands/cm; and polyester-cotton (70/30) 24 strands/cm. The pouches were washed in 1.0 M KOH for 15 min at 20° C., rinsed and oven dried. 0.2 ml of universal indicator was added to 40 ml of gamma ray-sterilized colloidal silica (described in Example 1). Approximately 0.6 ml of 4 M HCl was added to adjust the pH to 6. The colloidal silica was then doped with 1.0 ml of *P. chrysogenum* spore suspension containing $7\times10^7$ cfu/ml. The suspension was soaked into each pouch to saturation. The finer weave fabrics saturated more easily and formed finer membranes. The pouches were aged over night before 80 ml of MYEB (described in Example 1) was added to each pouch. 1.0 ml sample were taken daily for carbohydrate, penicillin and pH analysis. After four days the MYEB was removed and the bioreactor was washed in sterile 0.85% saline for one hour before being replaced with fresh MYEB and incubated again.

The results for the four different pouches are shown in FIGS. 10 to 13, and show that carbohydrate consumption rates were comparable for all pouches, and that with all pouches, the penicillin production improved in a subsequent batch. This may have been due to the growth of the biolayer on the membrane. It appears from the data in FIGS. 10 to 13 that the polyester pouch produced penicillin at a lower level than the other pouches.

Different Gels

Three glass pouches and one cotton pouch (90×80 mm) were washed in KOH, rinsed and oven dried. The cotton pouch (NMB1) had no gel added, instead it was swabbed with 0.1 ml of *A. niger* spore suspension containing $7\times10^6$ cfu/ml. At $T_0$ only 5.0 ml of MYEB was added to the pouch. 10 ml of MYEB was added daily. After three days the MYEB was replaced with 80 ml of fresh MYEB and a return tube was attached and assembled in a peristaltic pump to top up the overflow. It was almost water tight immediately, demonstrating that the biomass can act as the membrane in the bioreactor without the need for a separate nanoporous gel. The glass pouches were doped with agar agar (NMB2), calcium alginate (NMB3) and colloidal silica (NMB4).

10 ml of a hot 1.5% solution of agar was soaked into a glass pouch and gelled by cooling at 20° C. The pouch was swabbed with 0.1 ml of the *A. niger* spore suspension containing $7\times10^6$ cfu/ml, was filled with 80 ml of MYEB and incubated at 28° C.

The second glass pouch was doped with calcium alginate. 5.0 ml of 4% alginic acid was adjusted to pH 6 using universal indicator and 0.2 µm filtered 1M NaOH solution. The sol was soaked into a glass pouch and was washed in 4% $CaCl2H_2O$ solution to gel the alginate. The pouch was swabbed with 0.1 ml of *A. niger* spore suspension, and 80 ml of MYEB was added.

The third glass pouch was doped with colloidal silica containing 0.1 ml of *A. niger* spore suspension, aged over night before 80 ml of MYEB was added.

All pouches were incubated at 28° C. MYEB was replaced in all pouches after four days.

The results are shown in FIG. 14. These shown that the different gels performed quite similarly. Even the pouch with no gel consumed carbohydrate at a rate comparable to those with gels after the first batch.

Elemental uptake by *A. niger* cultured in Nanoparticulate Membrane Bioreactors

From the Nanoparticulate Membrane Bioreactors in the gel assay (above) having silica gel supported in a glass support, 3.0 ml samples were taken for elemental analysis using inductively coupled plasma atomic emission spectroscopy (ICP-AES). ICP-AES was performed on 3.0 ml nitric-acid digested samples using a Varian Vista ICP-AES with an AIM autosampler. At the start and the end of batches, 50 ml samples were also taken for CNS (carbon/nitrogen/sulfur) analysis. CNS analysis was performed on 50 ml samples of broth that were oven dried and analysed in a Leco CNS-2000. After one batch (3 days) the spent broth was removed from the bioreactor. 40 ml of 1% $CuSO_4$ solution was added to NMB1, 79.2 ml of MYEB and 0.8 ml of metal solution containing: 0.1% $CuSO_4$; 0.2% $ZnSO_4.7H_2O$; 0.2% $MnSO_4.H_2O$; 0.2% $NiCl_2$ and was also saturated with $PbCl_2$, at pH4.00 were added to NMB2 and NMB3, and 80 ml of metal solution was added to NMB4.

Results are shown in FIG. 15. These results show that consumption of carbohydrate is largely paralleled by a loss of potassium, phosphorus, calcium and magnesium from solution. Zinc concentration also dropped over a comparable time, although from a very low starting level, and the drop in sulfur concentration occurred over a comparable time, although the sulfur level did not drop as far as for the other analytes. CNS analysis of a secondary batch culture of *A. niger* grown on a bioreactor having silica gel supported in a glass support, consumed 77% of the total carbon, 61% of the total nitrogen and 65% of the total sulfur in 23 hours.

EXAMPLE 3

Continuously-Flowing Nanoparticulate Membrane Bioreactor

A miniature continuously-flowing Nanoparticulate Membrane Bioreactor was made consisting of a stainless steel reservoir (80×30×25 mm) and a stainless steel scaffold assembled in the reservoir that extended up through a slit in the upper face by 100 mm. A pair of membranes composed of *A. niger*-doped colloidal silica and woven glass fibre matting, and joined at the edges, was assembled around the scaffold. Two hoses were attached to the top so that they drained into the thin lumen defined by the pair of membranes. The bottom of the pair of membranes drained into the slit in the top of the reservoir and the other ends of the two hoses were inserted into the reservoir via two holes in the upper face. The hoses were assembled in a peristaltic pump and the reservoir and scaffold were housed in a 1000 ml beaker covered with an aluminium foil lid. The NMB was filled with 60 ml of MYEB and was incubated at 28° C. 1.0 ml samples were taken daily for carbohydrate and pH analysis and the MYEB was replaced after four days. Results are shown in FIG. 16. The data show that the first batch provided slower carbohydrate consumption for the continuously flowing reactor than for the batch reactor, however a subsequent batch was comparable to the batch reactor. It appears that the biolayer is slower to establish in a continuously flowing system, however once established, it is capable of performing as well as in a static batch system.

Preparation of Glass-Fiber Matting

Woven glass pouches were primed for adhesion of silica gel in two ways, namely: water-plasma etched with hydroxyl free-radicals (see following); and 1 M potassium hydroxide (KOH) bath for 15 minutes at 20° C. Pouches were etched for 6.0 min in water plasma at $=5.0 \times 10^{-2}$ millibar in a 40 W RF-plasma generator operating at 13.56 mH RM to hydroxylate the surfaces making them wettable. This technique was used in Example 1 and the method of soaking in KOH solution was used in Examples 2 and 3. It is also envisaged that an oven could be used to burn the hydrophobic sizing off the glass matting to make the surfaces wettable. It is also envisaged that UV-irradiation in the presence of water vapour could be used to make the glass material wettable. Glass-fiber matting may also be treated with concentrated nitric acid for about one hour in order to remove the sizing.

EXAMPLE 4

Waste-Water Treatment

Figure 17:
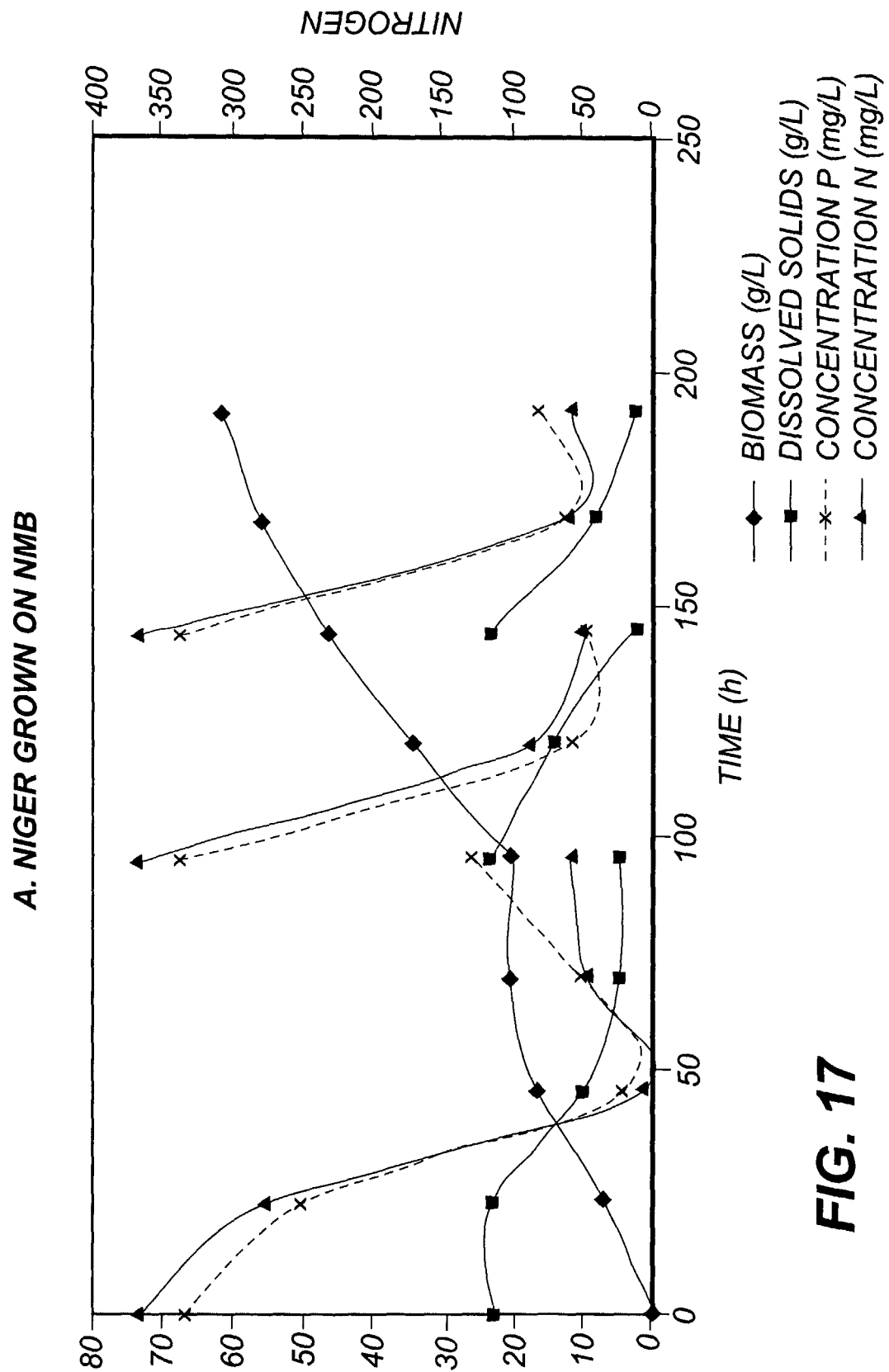
FIG. 17 shows a graph of various measured parameters over time for growth of *A. niger* in an NMB with concurrent removal of dissolved solids, P and N from malt extract broth, from example 4.

To simulate recovery of chemicals from a waste-water stream, *A. niger* was grown in eight pouch-style NMB at 30° C. with malt extract broth (30.0 g/L) as a simulated wastewater. At daily intervals, whole NMB were subjected to loss-on-ignition analysis to determine the biomass load. The liquid broth was dehydrated at 110° C. to determine the amount of dissolved solids and samples of the same solution were analyzed by ICP-AES and CNS analyses to determine the quantities of different elements in the simulated waste water. Results are shown in FIGS. 17 and 18.

EXAMPLE 5

Bioleaching and Biotransformation

Figure 19:
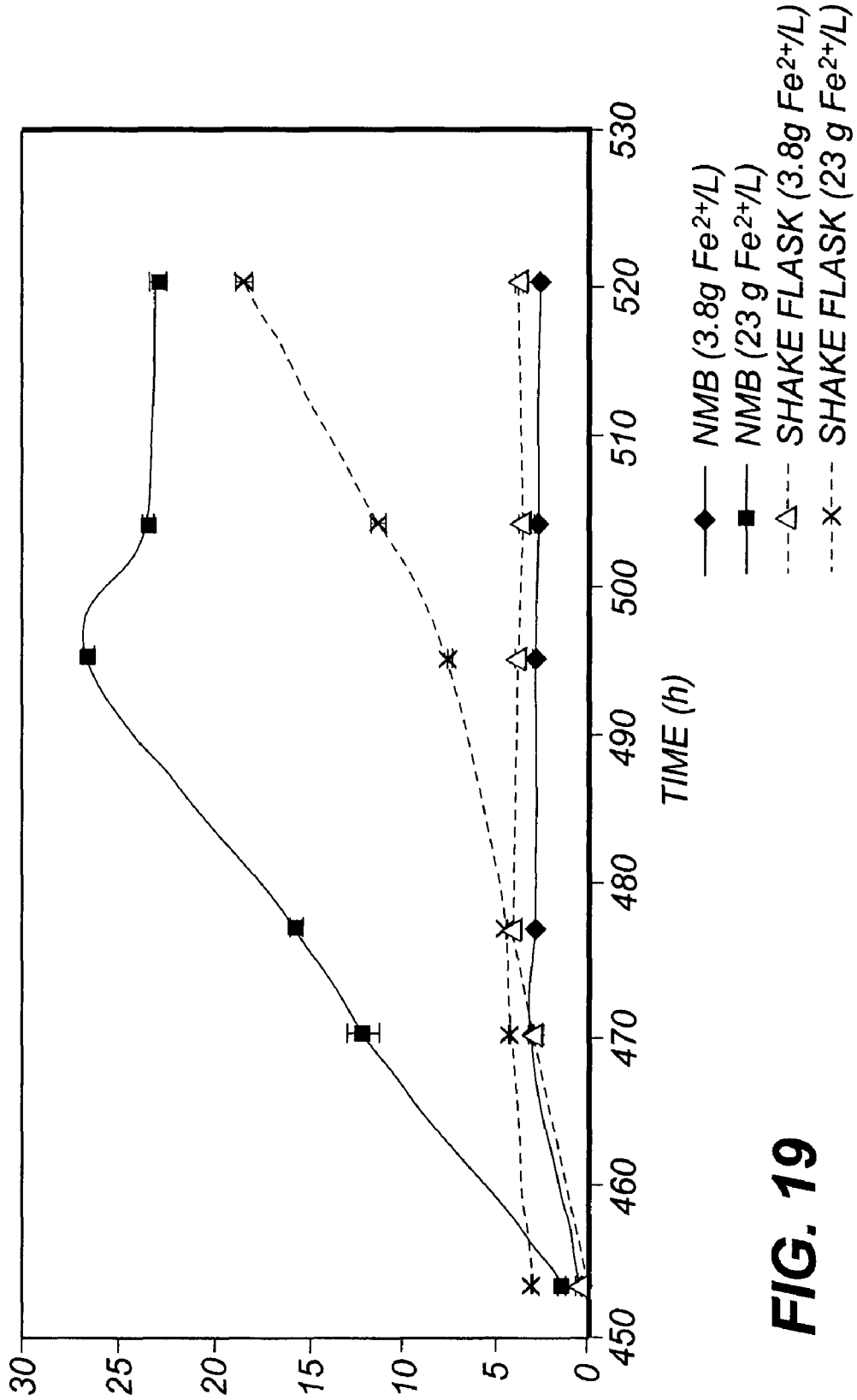
FIG. 19 shows a graph of ferric ion concentration over time in the conversion of ferrous iron to ferric iron by *A. ferrooxidans* in NMB and shake-flask cultures from example 5.

*Acidithiobacillus ferroxidans* was cultured at 30° C. in medium DSMZ #670 with 3.8 and 23.0 g/L $Fe^{2+}$ in the form of $FeSO_4.7H_2O$ in shake-flask culture (110 ml medium at 100 r.p.m.) and pouch-style NMB (126 cm² containing 100 ml broth). After each batch (3-4 days) the solution was drained from the NMB and replaced with 100 ml of fresh medium, and was drained from the shake-flask cultures and replaced with 100 ml of fresh medium and inoculated with 10 ml from the previous batch. The cultures were analysed for $Fe^{3+}$ concentration. Results are shown in FIG. 19, which shows a graph of $Fe^{3+}$ over time.

EXAMPLE 6

Mammalian Tissue Culture

Mouse breast cancer cell lines MAT and B16 and hamster fibroblast cell line V79 were cultured in RPMI 1640 medium containing per liter: 100 ml fetal bovine serum, 0.292 g L-glutamine, 63 mg penicillin and 100 mg streptomycin. The cells were incubated at 37.0° C. in a humidified atmosphere containing 5.0% $CO_2$. Cells were cultured in pouch-style NMB composed of woven glass material doped with silica gel containing 50 ml of medium with 72 cm² of membrane cultured, and in 24 cm² tissue culture flasks, containing 10 ml of medium. Cells were harvested with trypsin EDTA solution, stained with trypan blue and were enumerated in a heamocytometer. Cell growth on the outer surface of the NMB was poor for all of the cell lines tested (Table 3), which may have been due to dehydration, toxic oxygen species, or both. It may have also been due to the silica being too hydrophylic, as it has been reported that mammalian tissues will only grow on methylated (hydrophobic) silica gels.

TABLE 3

Mammalian tissue culture in and on NMB and in tissue culture flasks.

| Culture vessel | Tissue Culture | | |
| --- | --- | --- | --- |
| | MAT | B16 | V79 |
| NMB | | | |
| Gas surface (cells/cm²) | $2.2 \times 10^4$ | $8.3 \times 10^4$ | $2.8 \times 10^5$ |
| Liquid surface (cells/cm²) | $7.2 \times 10^5$ | $3.3 \times 10^5$ | |
| Lumen (cells/ml) | $9.0 \times 10^6$ | $2.9 \times 10^6$ | |
| Base of beaker* (cells/cm²) | $3.9 \times 10^6$ | $1.5 \times 10^5$ | |
| TCF | | | |
| Base of flask (cells/cm²) | $3.6 \times 10^6$ | $4.2 \times 10^7$ | $1.6 \times 10^7$ |

NMB: Nanoparticulate membrane bioreactor;
*The NMB was suspended in a beaker and liquid medium leaked into the beaker and was returned to the pouch via a peristaltic pump;
TCF: Tissue culture flask.

The invention claimed is:

1. A bioreactor comprising:
   a membrane-supporting structure; and
   a membrane supported on the membrane-supporting structure, said membrane having a nutrient face, a gas face and a thickness between said faces, said membrane having an immobilised biolayer in a location selected from on the gas face and in the membrane near the gas face, wherein the membrane comprises a gel reinforced by a support between the gas face and the nutrient face, and the gel providing communication between the nutrient face and the gas face of the membrane allowing diffusion of a nutrient solution through the membrane and the membrane allows diffusion of a nutrient solution from the nutrient face to the immobilised biolayer,
   and wherein the membrane, when supported by the supporting structure, has one configuration selected from the group consisting of:
   a pair of membranes disposed so as to define an inside region between the membranes of the pair;

the membrane disposed adjacent to a non-porous support disposed so as to define an inside region between the membrane and the non-porous support, said non-porous support comprising a material that is impervious to the nutrient solution; and the membrane supported in a configuration in which a portion of the membrane is parallel to another portion of the membrane so as to define an inside region between the two portions, and wherein the nutrient face abuts the inside region.

2. The bioreactor of claim 1 wherein the inside region between the membranes of the pair abuts the nutrient face of each of the membranes of the pair.

3. The bioreactor of claim 1, wherein the membrane is supported on the membrane-supporting structure in an orientation selected from the group consisting of vertically, non-horizontally, at a non-zero angle to the horizontal, at an angle to the horizontal between about 30° and 90°, at an angle to the horizontal between about 45° and 90°, at an angle to the horizontal between about 60° and 90° at an angle to the horizontal between about 45° and 60°, at an angle to the horizontal of about 30°, at an angle to the horizontal of about 45°, and at an angle to the horizontal of about 60°.

4. The bioreactor of claim 1 wherein the membrane is supported vertically.

5. The bioreactor of claim 1 wherein the membrane is a planar membrane, and wherein the membranes of the pair are supported in a configuration such that a portion of one membrane of the pair is parallel to a portion of the other membrane of the pair.

6. The bioreactor of claim 1 comprising one or more spacers for maintaining a distance between the membranes of the pair.

7. The bioreactor of claim 1 having an inlet for admitting the nutrient solution to the nutrient face of the membrane, an outlet for removing the nutrient solution from the nutrient face of the membrane, and a recycling system for recycling the nutrient solution from the outlet to the inlet.

8. The bioreactor of claim 7 wherein the recycling system is capable of preventing access of oxygen to the liquid.

9. The bioreactor of claim 1 also comprising an oxygen remover for removing oxygen from the nutrient solution.

10. The bioreactor of claim 1 having means for removing solid matter from the membrane.

11. The bioreactor of claim 1 wherein the biolayer is both on the gas face and in the membrane near the gas face.

12. The bioreactor of claim 1 wherein the biolayer is exposed such that cells from the immobilised biolayer may be removed once formed.

13. A method for operating a bioreactor that comprises:
a membrane-supporting structure; and
a membrane supported on the membrane-supporting structure, said membrane having a nutrient face, a gas face and a thickness between said faces, said membrane having an immobilised biolayer in a location selected from on the gas face and in the membrane near the gas face;
wherein the membrane comprises a gel reinforced by a support between the gas face and the nutrient face, and the gel providing communication between the nutrient face and the gas face of the membrane allowing diffusion of a nutrient solution through the membrane and the membrane allows diffusion of a nutrient solution from the nutrient face to the immobilised biolayer, and wherein the membrane when supported by the supporting structure has one configuration selected from the group consisting of:
a pair of membranes disposed so as to define an inside region between the membranes of the pair;
the membrane disposed adjacent to a non-porous support disposed so as to define an inside region between the membrane and the non-porous support, said non-porous support comprising a material that is impervious to the nutrient solution; and
the membrane supported in a configuration in which a portion of the membrane is parallel to another portion of the membrane so as to define an inside region between the two portions, and
wherein the nutrient face abuts the inside region, said method comprising:
exposing the nutrient face of the membrane to a nutrient solution,
exposing the biolayer to a gas, and
allowing the nutrient solution to diffuse from the nutrient face of the membrane to the biolayer.

14. The method of claim 13 wherein, in use, the nutrient solution is substantially anoxic.

15. The method of claim 13 wherein the nutrient solution is substantially anoxic.

16. The method of claim 13 wherein the step of allowing the nutrient solution to diffuse is performed with a pressure across the membrane of less than 0.05 atmosphere.

17. The method of claim 13 wherein the gas contains oxygen.

18. The method of claim 13 wherein the step of exposing the nutrient face of the membrane to a nutrient solution comprises recycling the nutrient solution past the nutrient face.

19. The method of claim 13 wherein the nutrient solution does not pass through the membrane into a gas region adjoining the gas face of the membrane.

20. The method of claim 13 wherein the biolayer and the composition of the nutrient solution are chosen for a purpose selected from the group consisting of producing pharmaceuticals, producing antibodies, producing vaccine components, producing food material, producing cells, producing enzymes and for the purpose of removing, degrading or converting components in the nutrient solution.

21. The method of claim 13 wherein the biolayer and the composition of the nutrient solution are chosen for production of an antibiotic.

22. The method of claim 13 also comprising the step of removing oxygen from the nutrient solution.

23. The method of claim 13 additionally comprising the step of isolating a product of the bioreactor.

24. The method of claim 23 wherein the step of isolating comprises separating the product from the nutrient solution.

25. The method of claim 23 wherein the step of isolating comprises harvesting solid matter from the gas face.

26. The method of claim 13 additionally comprising:
introducing a second liquid to the nutrient face of the membrane,
exposing the membrane to the second liquid for a second period of time, and
separating a product from the second liquid.

27. The method of claim 13 wherein the biolayer includes an outer surface in direct contact with the gas.

28. The method of claim 13 wherein the pressure of the gas at the gas face is between about 0.9 and 1.1 atmospheres.

* * * * *